(12) United States Patent
Dinca et al.

(10) Patent No.: US 12,030,839 B2
(45) Date of Patent: Jul. 9, 2024

(54) METHODS AND COMPOSITIONS FOR THE CATALYTIC UPGRADING OF ALCOHOLS

(71) Applicant: Massachusetts Institute of Technology, Cambridge, MA (US)

(72) Inventors: Mircea Dinca, Belmont, MA (US); Constanze Nicole Neumann, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 347 days.

(21) Appl. No.: 17/106,345

(22) Filed: Nov. 30, 2020

(65) Prior Publication Data

US 2021/0163386 A1 Jun. 3, 2021

Related U.S. Application Data

(62) Division of application No. 16/360,155, filed on Mar. 21, 2019, now Pat. No. 10,882,807.

(Continued)

(51) Int. Cl.
*C07C 29/44* (2006.01)
*B01J 23/46* (2006.01)
(Continued)

(52) U.S. Cl.
CPC ............... *C07C 29/44* (2013.01); *B01J 23/46* (2013.01); *B01J 31/1691* (2013.01);
(Continued)

(58) Field of Classification Search
None
See application file for complete search history.

(56) References Cited

U.S. PATENT DOCUMENTS

| 10,882,807 B2 | 1/2021 | Dinca et al. |
| 2014/0235901 A1 | 8/2014 | Gadewar et al. |
| 2015/0231622 A1 | 8/2015 | Kitagawa et al. |

FOREIGN PATENT DOCUMENTS

CN 107376996 A 11/2017

OTHER PUBLICATIONS

Hosny et al. (Journal of Thermal Analysis and Calorimetry, 122(1), 89-95). (Year: 2015).*

(Continued)

*Primary Examiner* — Yun Qian
(74) *Attorney, Agent, or Firm* — Wolf, Greenfield & Sacks, P.C.

(57) ABSTRACT

Compositions and methods of use related to metal organic frameworks (MOFs) and/or nanoparticles are generally described. In some embodiments, methods and compositions for the catalytic upgrading of alcohols using MOFs and/or nanoparticles associated with MOFs are generally described. In some embodiments, a catalytic MOF composition is provided, wherein the MOF composition comprises a MOF compound and a plurality of metal catalytic compounds. In some embodiments, an alcohol may be exposed to the MOF composition and/or a plurality of nanoparticles associated with the MOF composition such that the alcohol is converted to a higher order alcohol. Advantageously, in some embodiments, the alcohol conversion occurs at a relatively high turnover frequency and/or with a relatively high selectivity as compared to traditional methods for converting alcohols.

19 Claims, 25 Drawing Sheets

Related U.S. Application Data

(60) Provisional application No. 62/809,198, filed on Feb. 22, 2019, provisional application No. 62/645,827, filed on Mar. 21, 2018.

(51) Int. Cl.
| | |
|---|---|
| *B01J 31/16* | (2006.01) |
| *C07C 31/12* | (2006.01) |
| *C07C 31/125* | (2006.01) |
| *C07F 15/00* | (2006.01) |
| *C07F 15/04* | (2006.01) |
| *C07F 15/06* | (2006.01) |
| *C07C 29/16* | (2006.01) |

(52) U.S. Cl.
CPC ............ *C07C 31/12* (2013.01); *C07C 31/125* (2013.01); *C07F 15/0046* (2013.01); *C07F 15/04* (2013.01); *C07F 15/06* (2013.01); *B01J 2231/46* (2013.01); *B01J 2531/0208* (2013.01); *B01J 2531/821* (2013.01); *B01J 2531/845* (2013.01); *B01J 2531/847* (2013.01); *C07C 29/16* (2013.01)

(56) References Cited

OTHER PUBLICATIONS

Aitchison et al., Homogeneous Ethanol to Butanol Catalysis—Guerbet Renewed. ACS Catal. Sep. 2, 2016;6(10):7125-32. Doi: 10.1021/acscatal.6b01883.

\* cited by examiner

METHODS AND COMPOSITIONS FOR THE CATALYTIC UPGRADING OF ALCOHOLS

RELATED APPLICATIONS

This application is a division of U.S. patent application Ser. No. 16/360,155, entitled "METHODS AND COMPOSITIONS FOR THE CATALYTIC UPGRADING OF ALCOHOLS" filed on Mar. 21, 2019, which claims priority under 35 U.S.C. § 119(e) to U.S. Provisional Application Ser. No. 62/645,827, entitled "METHODS AND COMPOSITIONS FOR THE CATALYTIC CONVERSION OF ETHANOL TO BUTANOL" filed on Mar. 21, 2018 and U.S. Provisional Application Ser. No. 62/809,198, entitled "METHODS AND COMPOSITIONS FOR THE CATALYTIC UPGRADING OF ALCOHOLS" filed on Feb. 22, 2019, each of which is incorporated herein by reference in its entirety.

STATEMENT OF GOVERNMENT SUPPORT

This invention was made with Government support under DMR1645232 awarded by the National Science Foundation. The Government has certain rights in the invention.

TECHNICAL FIELD

Methods and compositions for the catalytic upgrading of alcohols using nanoparticles associated with MOFs are generally described.

BACKGROUND

Simple biomass-derived fuels have the potential to be implemented as sustainable and renewable energy sources. Furthermore, the upgrading of simple biofuels, such as short chain alcohols, is a desirable process that can be implemented to replace fossil fuels with sustainable fuels. Converting ethanol to butanol (e.g., 1-butanol), for example, could alleviate problems arising from using ethanol as a fuel or fuel additive due to the fact that the physical properties of 1-butanol are more applicable for use as a sustainable fuel. For example, 1-butanol has an energy density of 90%, which is closer to gasoline than ethanol, which has an energy density of 70%. Furthermore, 1-butanol does not have the same propensity as ethanol to absorb water. Unlike ethanol, which is made from corn and cellulosic materials with worldwide production exceeding 95 billion liters per year in 2015, 1-butanol is produced mainly from fossil resources.

Current alternative routes to 1-butanol include the hydration and/or hydrogenation of butadiene and the acetone-butanol-ethanol fermentation process. Due to the toxicity of butanol to the fermentation bacteria, the maximum achievable concentration of butanol in the fermentation broth is generally low, and the separation of 1-butanol from the dilute aqueous solution accounts for a significant fraction of the biofuel production cost. Less expensive and more practical heterogeneous catalysts yield 1-butanol with low selectivity and/or require harsh reaction conditions. Accordingly, improved methods and compositions are needed.

SUMMARY

Methods and compositions for the catalytic upgrading of alcohols using nanoparticles associated with MOFs are generally described.

According to certain embodiments, a method of converting ethanol to 1-butanol is described, comprising exposing a catalytic MOF composition to ethanol to produce 1-butanol, wherein the catalytic MOF composition comprises a MOF compound and a plurality of metal catalytic compounds, and wherein the MOF compound comprises a plurality of pores and the plurality of metal catalytic compounds are contained in the plurality of pores.

In certain embodiments, a method is described, wherein the method comprises exposing a MOF precursor composition to ethanol and a base, thereby activating the MOF precursor composition to form a catalytic MOF composition, wherein the MOF precursor composition comprises an MOF compound and plurality of precursor metal catalytic compounds, wherein the MOF compound comprises a plurality of pores and the plurality of precursor metal catalytic compounds are contained in the plurality of pores, and wherein the MOF precursor composition is activated when at least a portion of the precursor metal catalytic compounds are reduced to form metal catalytic compounds, and wherein at least a portion of the ethanol is converted to 1-butanol.

Some embodiments are related to a MOF composition comprising a MOF compound comprising a plurality of cobalt ions, a plurality of ligands, and a plurality of pores, wherein each cobalt ion is coordinated with at least one ligand, and a plurality of metal catalytic compounds, wherein the plurality of metal catalytic compounds are contained in the plurality of pores, and wherein each of the plurality of ligands comprises at least two pyrazolate groups.

Certain embodiments related to a method for catalytic conversion of a first alcohol are described, wherein the method comprises exposing the first alcohol to a plurality of nanoparticles comprising a metal catalytic compound, the metal catalytic compound comprising a plurality of metal atoms, and converting the first alcohol to a second alcohol, the second alcohol having a greater number of carbon atoms than the first alcohol. In some embodiments, the plurality of metal atoms comprise ruthenium (Ru) and nickel (Ni) or cobalt (Co). In certain embodiments, conversion of the first alcohol to the second alcohol has a turnover frequency of greater than or equal to 1000 $Ru^{-1}h^{-1}$ measured at 170° C., and/or the metal catalytic compound has a second alcohol selectivity of greater than or equal to 90%.

Some embodiments are related to an article, wherein the article comprises a plurality of nanoparticles comprising a metal catalytic compound, the metal catalytic compound comprising a nickel-based alloy with Ru and/or a cobalt-based alloy with Ru. In some embodiments, the metal catalytic compound has a turnover frequency for ethanol of greater than or equal to 1000 $Ru^{-1}h^{-1}$ measured at 170° C., and the metal catalytic compound has a second alcohol selectivity of greater than or equal to 90%.

Certain embodiments related to a method of upgrading an alcohol are described, wherein the method comprises exposing a catalytic MOF composition to one or more first alcohols, and converting at least a portion of the one or more first alcohols to one or more second alcohols. In certain embodiments, the catalytic MOF composition comprises a MOF compound and a plurality of metal catalytic compounds, wherein the MOF compound comprises a plurality of cobalt atoms or nickel atoms, and at least a portion of the plurality of metal catalytic compounds are bonded with at least a portion of the cobalt atoms or nickel atoms in the form of an alloy comprising $Ru_xCo_{x-1}$ and/or $Ru_xNi_{x-1}$ nanoparticles.

Some embodiments are related to a method of upgrading an alcohol, wherein the method comprises exposing a MOF precursor composition to one or more first alcohols and a base, activating the MOF precursor composition to form a catalytic MOF composition, and converting at least a portion of the one or more first alcohols to one or more second alcohols. In certain embodiments, the MOF precursor composition comprises a plurality of precursor metal catalytic compounds and a MOF compound comprising a plurality of cobalt ions and/or nickel ions. In some embodiments, the MOF precursor composition is at least partially activated when at least a portion of the precursor metal catalytic compounds are reduced to metal catalytic compounds, and at least a portion of the metal catalytic compounds bond to at least a portion of the cobalt and/or nickel ions to form an alloy comprising $Ru_xCo_{x-1}$ and/or $Ru_xNi_{x-1}$ nanoparticles.

Some embodiments related to a MOF composition are described, wherein the MOF composition comprises a MOF compound comprising a plurality of cobalt and/or nickel atoms and a plurality of metal catalytic compounds, wherein at least a portion of the plurality of metal catalytic compounds are bonded with at least a portion of the cobalt atoms or nickel atoms in the form of an alloy.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
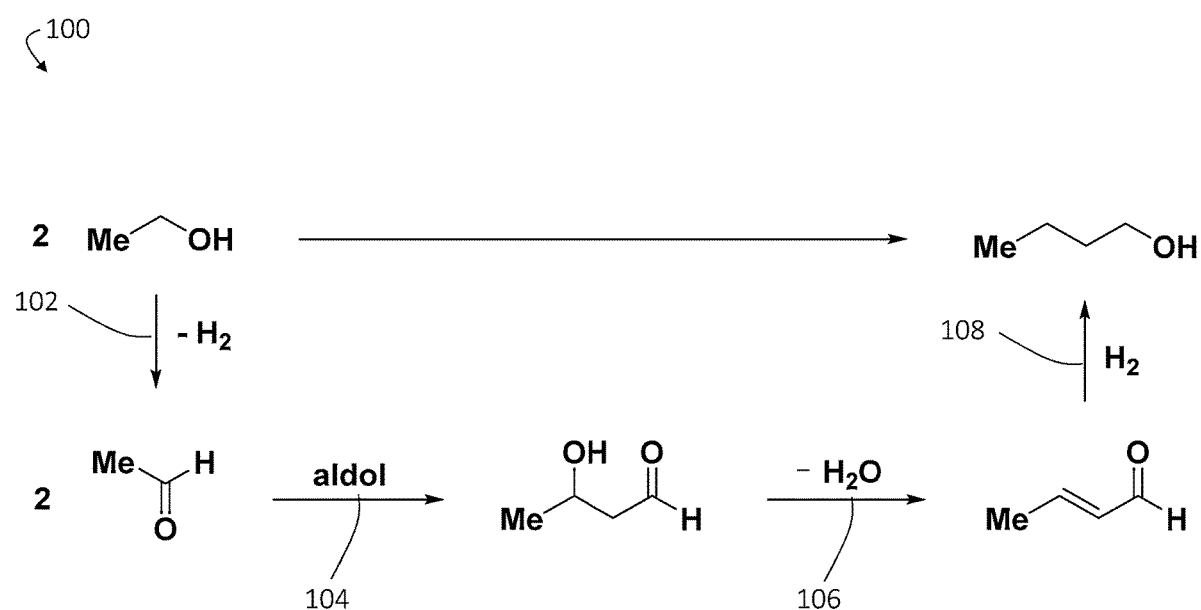
FIG. 1 shows, according to certain embodiments, the proposed mechanism of the Guerbet reaction for the conversion of ethanol to 1-butanol.

Compositions and methods of use related to metal organic frameworks (MOFs) and/or nanoparticles (e.g., nanoparticles associated with MOFs) are generally described. In some embodiments, methods and compositions for the catalytic upgrading of alcohols using MOFs and/or nanoparticles associated with MOFs are generally described. In an exemplary set of embodiments, an alcohol may be exposed to a plurality of nanoparticles (e.g., comprising a metal catalytic compound) such that the alcohol is converted to a higher order alcohol (e.g., having a greater number of carbon atoms after conversion as compared to prior to conversion). Advantageously, in some embodiments, the alcohol conversion occurs at a relatively high turnover frequency and/or with a relatively high selectivity as compared to traditional methods for converting alcohols. In some embodiments, the plurality of nanoparticles may be catalytically active. In certain embodiments, the catalytically active plurality of nanoparticles may be associated with a catalytic MOF, as described in more detail below.

In some embodiments, a catalytic MOF composition is provided, wherein the MOF composition comprises a MOF compound and a plurality of metal catalytic compounds. In certain embodiments, the MOF compound comprises a plurality of metal atoms (e.g., cobalt (Co) ions or nickel (Ni) ions). In some embodiments, the MOF compound comprises a plurality of pores, and the plurality of metal catalytic compounds are contained in the plurality of pores. In some embodiments, the metal catalytic compounds comprise ruthenium (Ru).

In certain embodiments, at least a portion of the plurality of metal catalytic compounds (e.g., comprising Ru) and at least a portion of the metal atoms (e.g., Co or Ni ions) are bonded with each other. In some embodiments, for example, at least a portion of the plurality of metal catalytic compounds bonds with at least a portion of the metal atoms to form a plurality of nanoparticles (e.g. Ru- and Co-containing nanoparticles or Ru- and Ni-containing nanoparticles). In certain embodiments, the nanoparticles are associated with the MOF composition. According to some embodiments, the nanoparticles are derived from the MOF composition. For example, in certain embodiments, the nanoparticles that have formed comprise at least a portion of the metal catalytic compound (e.g., Ru) and/or at least a portion of the metal atoms (e.g., Co or Ni). In some embodiments, for example, the metal catalytic compound comprising ruthenium (e.g., Ru$^0$) bonds with the metal atoms (e.g., Co$^0$ or Ni$^0$). In some embodiments, at least a portion of the plurality of metal catalytic compounds forms a bond with at least a portion of the metal atoms to form an alloy (e.g., Ru- and Co-based alloy, or a Ru- and Ni-based alloy). Accordingly, in some embodiments, the nanoparticles are in the form of an alloy. In certain embodiments, the nanoparticles have desirable catalytic activity towards the upgrading of alcohols. According to some embodiments, for example, the nanoparticles convert at least a portion of one or more first alcohols to one or more second alcohols. Methods of using the MOF composition and/or the plurality of nanoparticles associated with the MOF composition to upgrade alcohols are also described.

According to certain embodiments, a precursor MOF composition is provided, wherein the precursor MOF composition comprises a MOF compound and plurality of precursor metal catalytic compounds. In certain embodiments, the MOF compound comprises a plurality of pores, and the plurality of precursor metal catalytic compounds are contained in the plurality of pores. Methods for activating the precursor MOF composition are also described. In some embodiments, for example, activating the precursor MOF composition (e.g., by exposing the precursor MOF composition to a base) facilitates the formation of the MOF composition that is capable of upgrading alcohols. In certain embodiments, activating the precursor MOF composition (e.g., by exposing the precursor MOF composition to a base) facilitates the formation of the plurality of nanoparticles associated with the MOF composition that are capable of upgrading alcohols, facilitates the formation of the nanoparticles.

The catalytic MOF compositions described herein may be used in a variety of applications. For example, in some embodiments, the catalytic MOF composition is used as a catalyst. In some embodiments, the MOF composition is used as a catalyst for upgrading alcohols. For example, in certain embodiments, the MOF composition is used to convert a first alcohol to a second alcohol, wherein the second alcohol has a greater number of carbons than the first alcohol. In some embodiments, the one or more first alcohols comprises ethanol and/or 1-butanol. In certain embodiments, the one or more second alcohols comprises 1-butanol, 1-hexanol, 2-ethyl-butanol, 2-ethyl-hexanol, and/or combinations thereof. In certain embodiments, the MOF composition is used as a catalyst for converting ethanol to butanol (e.g., 1-butanol). According to certain embodiments, the catalytic MOF composition is exposed to ethanol, and ethanol is converted to 1-butanol by the catalytic MOF composition under various reaction conditions, described below in further detail. The catalytic MOF compositions described herein are particularly advantageous as catalysts for the conversion of ethanol to 1-butanol (and/or higher order alcohols).

In some embodiments, the plurality of nanoparticles described herein may be used in a variety of applications. For example, in certain embodiments, the plurality of nanoparticles is used as a catalyst. In some embodiments, the plurality of nanoparticles is used as a catalyst for upgrading alcohols. For example, in certain embodiments, the plurality of nanoparticles is used to convert a first alcohol to a second alcohol, wherein the second alcohol has a greater number of carbons than the first alcohol. In some embodiments, the one or more first alcohols comprises ethanol and/or 1-butanol. In certain embodiments, the one or more second alcohols comprises 1-butanol, 1-hexanol, 2-ethyl-butanol, 2-ethylhexanol, and/or combinations thereof. In certain embodiments, the plurality of nanoparticles is used as a catalyst for converting ethanol to butanol (e.g., 1-butanol). According to certain embodiments, the plurality of nanoparticles is exposed to ethanol, and ethanol is converted to 1-butanol by the plurality of nanoparticles under various reaction conditions, described below in further detail. The plurality of nanoparticles described herein are particularly advantageous as catalysts for the conversion of ethanol to 1-butanol (and/or higher order alcohols).

Advantageously, the MOF composition and/or the plurality of nanoparticles associated with the MOF composition, have relatively high turnover numbers (e.g., greater than 10,000 $Ru^{-1}$), high turnover frequency (e.g., greater than 1000 $Ru^{-1}h^{-1}$), high selectivity (e.g., greater than 90% for 1-butanol), and/or long catalyst lifetimes as compared to traditional catalysts for upgrading alcohols, as is described herein in greater detail. The catalytic MOF composition and/or the plurality of nanoparticles associated with the MOF composition may generally be used in any reactor suitable for upgrading alcohols (e.g., for the conversion of ethanol to 1-butanol). Additional details regarding the catalytic conversions are described herein.

The term "metal-organic framework" is given its ordinary meaning in the art and refers to a one-, two-, or three-dimensional coordination polymer including metal atoms (e.g., metal ions) and ligands which function as organic structural units, wherein a portion of the metal atoms are each chemically bonded to at least one bi-, tri- or polydentate organic structural unit. The metal atoms, in addition to being coordinated with at least one ligand, may also be bound to one or more auxiliary ligands, as described in more detail herein.

In some embodiments, a catalytic MOF composition is provided comprising a MOF compound and a plurality of metal catalytic compounds. For example, in some embodiments, the catalytic MOF composition comprises a MOF compound comprising a plurality of metal atoms (e.g., Co atoms or Ni atoms) and a plurality of ligands. According to some embodiments, in addition to the MOF compound, the catalytic MOF composition comprises a plurality of metal catalytic compounds (e.g., ruthenium catalytic compounds). According to certain embodiments, the metal catalytic compounds are contained within a plurality of pores in the MOF compound. While much of the description herein relates to metal catalytic compounds contained within a plurality of pores in the MOF compound, one of ordinary skill in the art would understand based upon the teachings of this specification that the metal catalytic compounds need not necessarily be contained within the plurality of pores. In some embodiments, the metal catalytic compound is associated with the MOF compound (e.g., via formation of a bond).

According to certain embodiments, the MOF composition is a heterogeneous catalyst. The term "heterogeneous catalyst" is given its ordinary meaning in the art and generally refers to a catalyst that is of a different phase than the reactants. In some embodiments, the heterogeneous catalyst is in the solid phase and the reactants are in the liquid phase. In some embodiments, the MOF compositions described herein are utilized in a solid state, for example, as a solid dispersed in a solution. One non-limiting advantage to heterogeneous catalysts is the catalyst may generally be easily separated from a reaction mixture.

In some embodiments, a precursor MOF composition is provided comprising a MOF compound and a plurality of precursor metal catalytic compounds. As used herein, the term "precursor" is given its ordinary meaning in the art and generally refers to a species that can participate in a chemical reaction and/or transformation that produces another compound. For example, in some embodiments, the precursor MOF composition comprises a MOF compound comprising a plurality of metal atoms (e.g., Co atoms or Ni atoms) and a plurality of ligands. According to some embodiments, in addition to the MOF compound, the MOF composition comprises a plurality of precursor metal catalytic compounds (e.g., ruthenium catalytic compounds). According to certain embodiments, the precursor metal catalytic compounds are contained within a plurality of pores in the MOF compound.

Certain embodiments are methods related to exposing a precursor MOF composition to one or more first alcohols (e.g., ethanol). According to certain embodiments, the precursor MOF composition is added to a reaction vessel (e.g., a reactor) containing one or more first alcohols. In certain embodiments, the precursor MOF composition is present in the reaction vessel prior to the one or more first alcohols, and the one or more first alcohols is added to the reaction vessel to expose the MOF composition to the one or more first alcohols in order to catalytically produce one or more second alcohols, wherein the one or more second alcohols has a greater number or carbons that the one or more first alcohols. For example, in certain embodiments, the first alcohol is ethanol and the second alcohol is 1-butanol.

Upon exposure to the one or more first alcohols, the precursor MOF composition may be activated to form a catalytic MOF composition and/or a plurality of nanoparticles associated with the MOF composition. For example, according to certain embodiments, the precursor MOF composition is at least partially activated upon exposure to the one or more first alcohols and a base, and/or optionally elevated temperatures. In some embodiments, more than one base (e.g., two bases, three bases, four bases, etc. are utilized). As used herein, the term "base" is given its ordinary meaning in the art and generally refers to a compound that in solution has a pH greater than 7, is capable of accepting protons, is capable of reacting with an acid to form a salt, and/or any chemical compound that is capable of giving up an unshared pair of electrons to an acid, in aqueous solution. Any of a variety of suitable bases can be utilized. For example, in some embodiments, the base is any suitable ethoxide, hydroxide, or bis(treimethyl)silyl amide. According to some embodiments, the base can be sodium ethoxide, potassium ethoxide, magnesium ethoxide, copper ethoxide, calcium hydroxide, sodium hydroxide, magnesium hydroxide, cesium hydroxide, potassium bis(trimethylsilyl)amide, and/or sodium bis(trimethylsilyl)amide. Other bases may also be utilized. In some embodiments, Mg metal is added as a precursor to the form the base, such as magnesium hydroxide and/or magnesium ethoxide. In certain embodiments, the base is sodium ethoxide and/or cesium hydroxide. In certain embodiments, elevated temperatures are provided by raising the temperature of the reaction vessel. The temperature of the reaction vessel can be any suitable temperature (e.g., 150° C.). Other reaction temperatures are described herein in greater detail.

In some embodiments, the precursor MOF composition is at least partially activated when at least a portion of the precursor metal catalytic compounds are reduced to form metal catalytic compounds. In some cases, at least a portion of the precursor metal catalytic compounds (e.g., ruthenium compounds) are reduced (e.g., to ruthenium metal) by a base and/or reducing agent. In some embodiments, at least a portion of the metal atoms (e.g., $Co^{2+}$ ions or $Ni^{2+}$ ions) are reduced by a base and/or reducing agent. In certain embodiments, the $Co^{2+}$ ions or $Ni^{2+}$ ions are reduced to $Co^0$ atoms or $Ni^0$ atoms. In some other embodiments, however, the cobalt or nickel ions may not be fully reduced to $Co^0$ atoms or $Ni^0$ atoms. For example, in some embodiments the cobalt or nickel atoms may have an oxidation state greater than 0 after being reduced (e.g., by a base and/or a reducing agent). Resultantly, in certain embodiments, activating the precursor MOF composition (e.g., by exposing the precursor MOF composition to a base) facilitates the formation of the MOF composition and/or the plurality of nanoparticles associated with the MOF composition that is capable of upgrading alcohols. Those of ordinary skill in the art will be aware of methods for determining whether reduction of the precursor metal catalytic compounds has occurred. For example, the coordination signature and/or oxidation state of the metal catalytic compound may be determined by UV-vis spectroscopy and/or X-ray photoelectron spectroscopy.

Figure 7A:
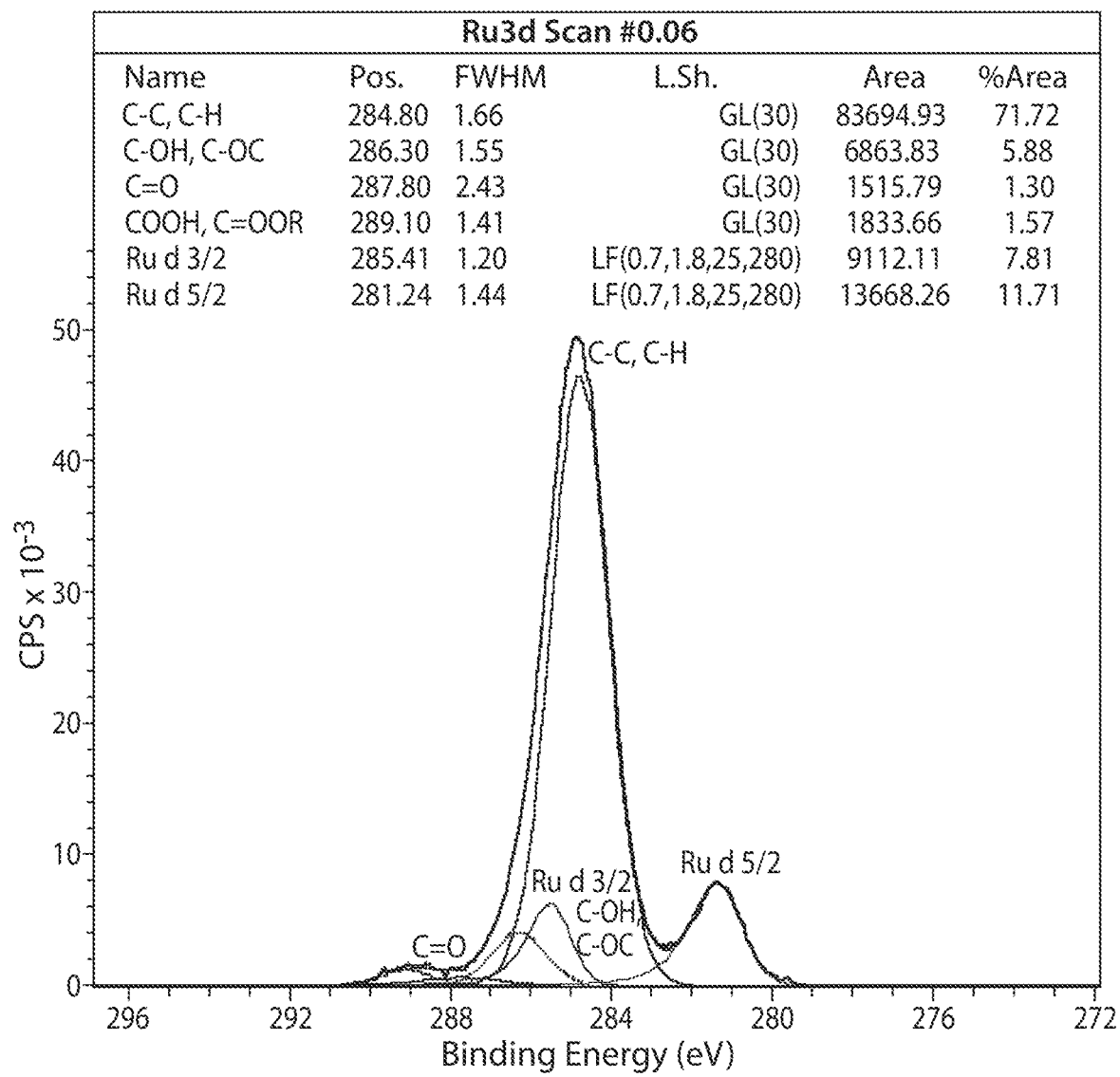
FIG. 7A shows, according to certain embodiments, X-ray photoelectron spectroscopy (XPS) data for an exemplary precursor MOF composition.
Figure 7B:
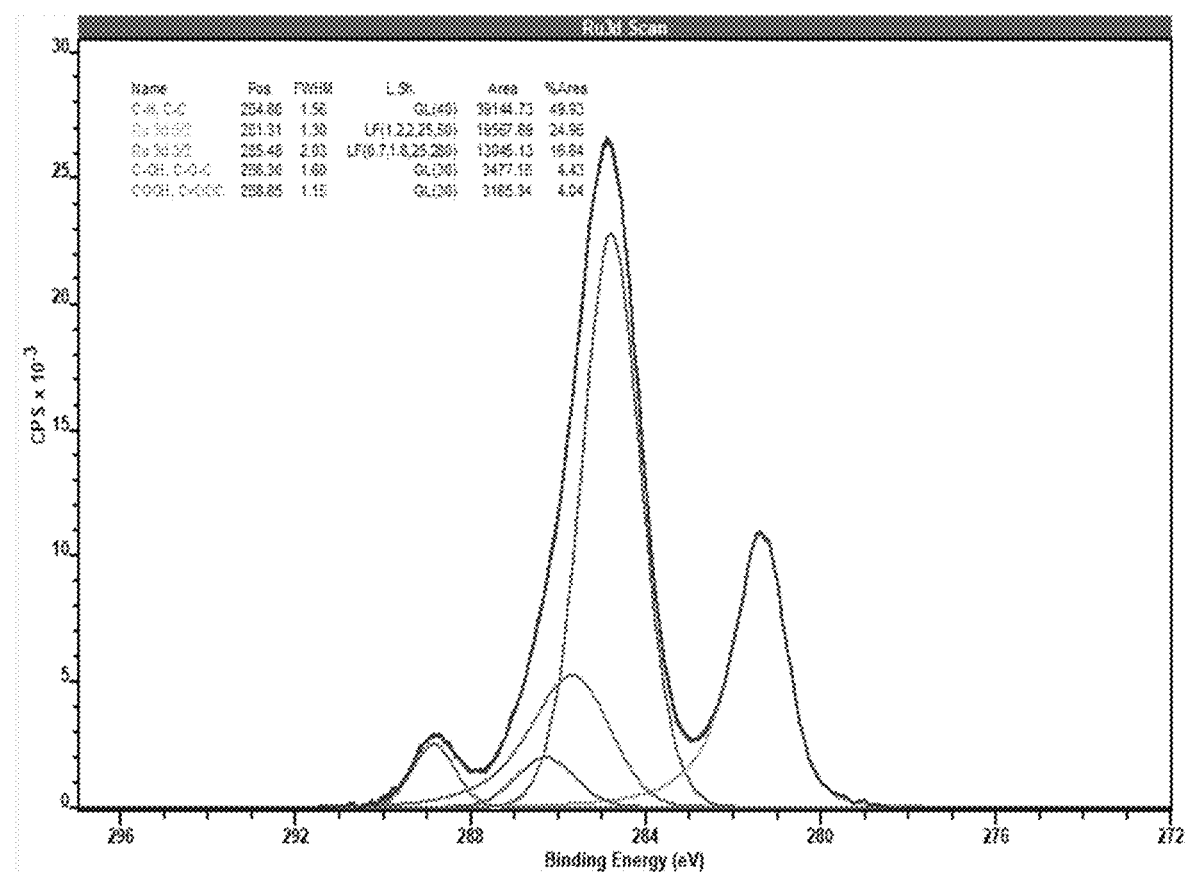
FIG. 7B shows, according to certain embodiments, XPS data for $[RuCl_2(nbd)]_2$.
Figure 7C:
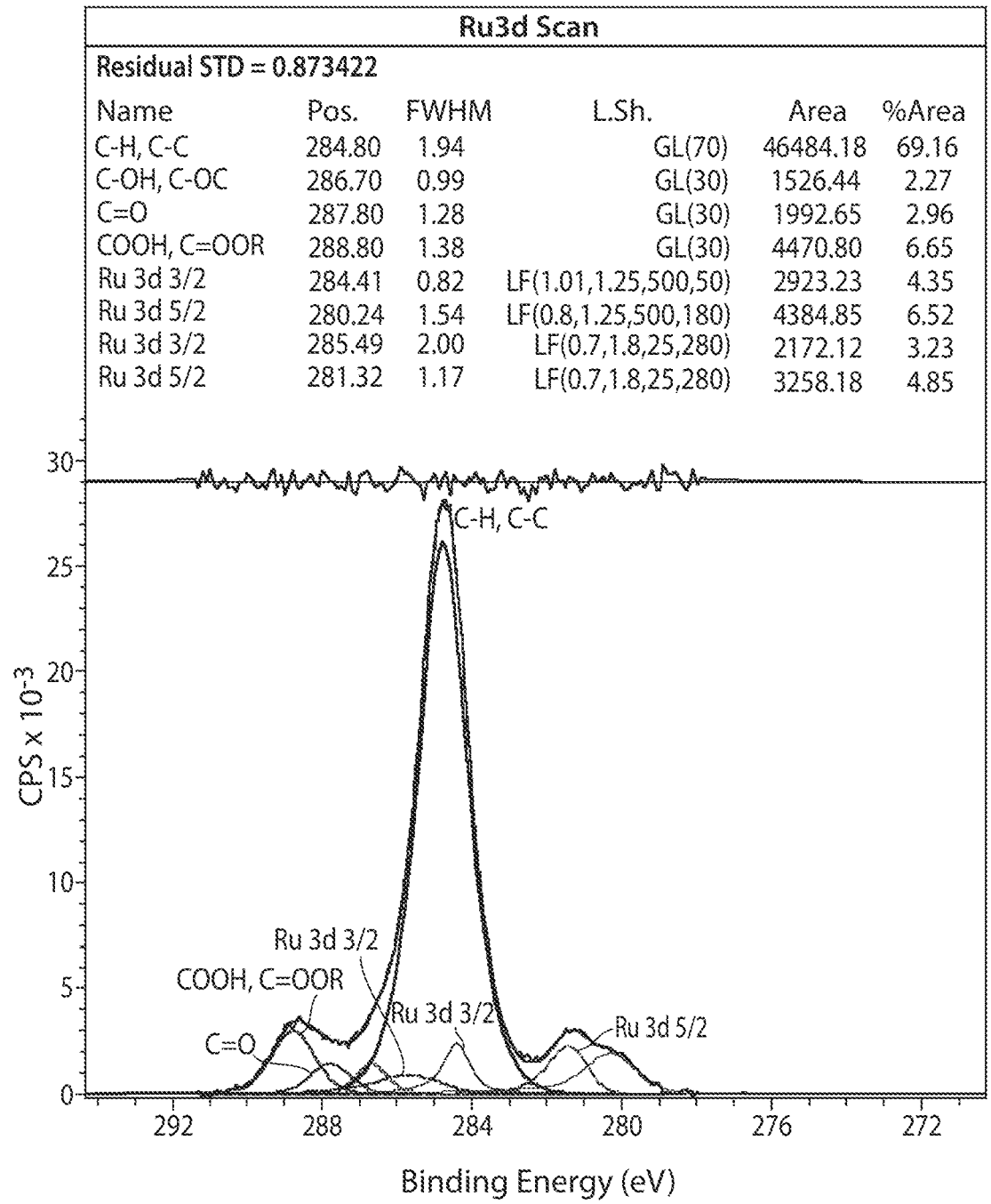
FIG. 7C shows, according to certain embodiments, XPS data for an exemplary recovered catalytic MOF composition.

A non-limiting example of an activation process and metal reduction is described in more detail in connection with FIG. 7A-7C. FIG. 7A-7C show, according to exemplary embodiments, X-ray photoelectron spectra for a precursor MOF composition, a precursor metal catalytic compound (as a control), and a recovered catalytic MOF composition after the conversion of ethanol to 1-butanol, respectively. According to certain embodiments, analysis of the recovered catalytic MOF composition after the catalytic conversion of ethanol to 1-butanol reveals the formation of a low valent metal catalytic compound (e.g., indicative of ruthenium metal) with a loss of MOF compound crystallinity, as shown in FIG. 7C. Additional details regarding these figures are described in more detail herein.

According to certain embodiments, upon activation of the MOF composition, at least a portion of the one or more first alcohols (e.g., ethanol) is converted to one or more second alcohols (e.g., butanol). In some cases, the conversion of ethanol to 1-butanol follows mechanism 100 of the Guerbet reaction (as shown in FIG. 1), wherein in first step 102, ethanol is dehydrogenated to form a carbonyl-containing intermediate and gaseous $H_2$. Second step 104 includes the aldolization of the carbonyl-containing intermediate forming an intermediate with a new C—C bond. This is followed by dehydration step 106, and hydrogenation step 108 to form 1-butanol. According to certain embodiments, the gaseous $H_2$ produced in the dehydrogenation step 102 is contained in the plurality of pores of the MOF compound, and the gaseous $H_2$ is later available for the final hydrogenation step 108 to produce 1-butanol.

As described herein, in certain embodiments, the MOF composition comprises a MOF compound. According to certain embodiments, the MOF compound comprises a plurality of metal atoms (e.g., Co atoms or Ni atoms), a plurality of ligands, and a plurality of pores.

In certain embodiments, the MOF compound comprises a plurality of metal atoms. According to some embodiments, the plurality of metal atoms comprise any of a variety of suitable metal atoms. In certain embodiments, the metal atoms are metal ions. Each metal ion, for example, may be monovalent, divalent, trivalent, or tetravalent. In some embodiments, each metal ion is a monovalent metal ion. Non-limiting examples of monovalent metal ions are $Ag^+$, $Cu^+$, and $Au^+$. In some embodiments, the metal ion is a divalent metal ion. Non-limiting examples of monovalent metal ions are $Mg^{2+}$, $Mn^{2+}$, $Fe^{2+}$, $Co^{2+}$, $Ni^{2+}$, $Cu^{2+}$, $Pd^{2+}$, $Pt^{2+}$, $Ru^{2+}$, $Cd^{2+}$, $Zn^{2+}$, $Pb^{2+}$, $Hg^{2+}$, $V^{2+}$, and $Cr^{2+}$. In some embodiments, the metal ion is a trivalent metal ion. Non-limiting examples of trivalent metal ions are $Fe^{3+}$, $V^{3+}$, $Ti^{3+}$, $Sc^{3+}$, $Al^{3+}$, $In^{3+}$, $Ga^{3+}$, $Mn^{3+}$, $Co^{3+}$, and $Cr^{3+}$. In some embodiments, the metal ion is a tetravalent metal ion. A non-limiting example of a tetravalent metal ion is $Ti^{4+}$.

In an exemplary embodiment, the plurality of metal atoms are a plurality of cobalt atoms (e.g., $Co^{2+}$ atoms). In another exemplary embodiment, the plurality of metal atoms are a plurality of nickel atoms (e.g., $Ni^{2+}$ atoms).

In some embodiments, the MOF compound comprises a plurality of a first type of metal atoms and a plurality of a second type of metal atoms. For example, in certain embodiments, the MOF compound comprises both Co atoms and Ni atoms. Other combinations of metal atoms are also possible, and one of ordinary skill in the art would be capable of selecting suitable metal atoms and combinations thereof based on the teachings of this specification. According to certain embodiments, the first metal atoms (e.g., Co atoms) and the second metal atoms (e.g., Ni atoms) are each coordinated with at least one ligand.

According to certain embodiments, the MOF compound comprises a plurality of ligands associated with the MOF compound. In certain embodiments, the ligand is associated with the MOF compound by covalent interactions (e.g., sigma bonding, pi bonding). In some embodiments, the ligand is associated with the MOF compound by non-covalent interactions (e.g., electrostatic interactions such as ionic interactions and or hydrogen bonding, pi stacking interactions, van der Waals forces, and/or hydrophobic interactions). In certain embodiments, each ligand comprises at least one N-substituted aromatic group. In some embodiments, each ligand comprises unsaturated N-heterocyclic aromatic groups. The unsaturated N-heterocyclic aromatic group may be selected from any of a variety of suitable groups. For example, according to certain embodiments, the unsaturated N-heterocyclic aromatic groups are pyrazoles.

In some embodiments, the ligand comprises at least two N-substituted aromatic groups arranged about an organic core. The organic core of the ligand comprising at least two N-substituted aromatic groups may be any suitable core. In some embodiments, the core is aromatic. In certain embodiments, the core is optionally substituted. Generally, the core comprises a rigid structure formed from fused aryl and/or heteroaryl rings. In some embodiments, the organic core comprises a plurality of fused aryl and/or heteroaryl rings. In some cases, the organic core comprises a plurality of fused aryl rings. In some cases, the organic core comprises one or more of benzyl, thiophenyl, carbazolyl, pyrrolyl, indolyl, and furanyl. In some embodiments, the ligand comprises two or more pyrazole groups (e.g., two pyrazole groups).

In some embodiments, the ligand comprises two pyrazole groups and has the general structure:

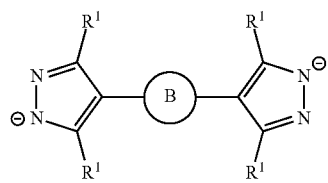

wherein Ring B is an optionally substituted aromatic or heterocyclic core (e.g., comprising one or more aromatic rings.

In some embodiments, each $R^1$ is the same or different and is selected from the group consisting of hydrogen (—H), optionally substituted alkyl (e.g., —CH$_3$), —NO$_2$, —R', —F, —Cl, —Br, —I, —CN, —NC, —SO$_3$R', —SO$_3$H, —OR', —OH, —SR', —SH, —PO$_3$R', —PO$_3$H, —CF$_3$, —NR'$_2$, —NHR', and —NH$_2$. In some embodiments, each $R^1$ is the same and is hydrogen. In some embodiments, each $R^1$ is the same and is optionally substituted alkyl (e.g., optionally substituted $C_{1-6}$ alkyl). In some embodiments, each $R^1$ is unsubstituted alkyl (e.g., unsubstituted $C_{1-6}$ alkyl). In certain embodiments, each $R^1$ is the same and is methyl (—CH$_3$).

In some embodiments, Ring B is optionally substituted arylene or optionally substituted heterarylene. In some embodiments, Ring B is optionally substituted phenylene. In some embodiments, Ring B is unsubstituted phenylene, for example, having the structure:

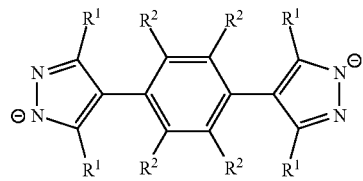

wherein each $R^1$ is the same or different and is selected from the group consisting of hydrogen (—H), optionally substituted alkyl (e.g., —CH$_3$), —NO$_2$, —R', —F, —Cl, —Br, —I, —CN, —NC, —SO$_3$R', —SO$_3$H, —OR', —OH, —SR', —SH, —PO$_3$R', —PO$_3$H, —CF$_3$, —NR'$_2$, —NHR', and —NH$_2$, and wherein each $R^2$ is the same or different and is selected from the group consisting of hydrogen (—H), optionally substituted alkyl (e.g., —CH$_3$), —NO$_2$, —R', —F, —Cl, —Br, —I, —CN, —NC, —SO$_3$R', —SO$_3$H, —OR', —OH, —SR', —SH, —PO$_3$R', —PO$_3$H, —CF$_3$, —NR'$_2$, —NHR', and —NH$_2$.

A non-limiting example of a ligand includes 1,4-bis[(3, 5-dimethyl)-pyrazol-4-yl]benzene, as shown below:

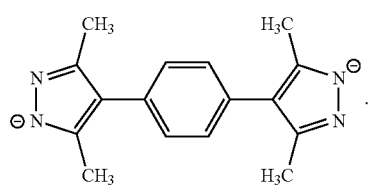 [SMILES: Cc1n[n-]c(C)c1-c1ccc(-c2c(C)n[n-]c2C)cc1]

In some embodiments, Ring B comprises phenyl. In certain embodiments, Ring B comprises biphenyl. In some embodiments, Ring B (e.g., phenyl, biphenyl, etc.) is optionally substituted. In certain embodiments, the optionally substituted Ring B is optionally substituted with fluorine. For example, in some embodiments, Ring B comprises phenyl substituted with fluorine (e.g., phenyl substituted with one, two, three, or four fluorine substituents). In certain embodiments, Ring B comprises biphenyl substituted with fluorine (e.g., biphenyl substituted with one, two, three, four, five, six, seven, or eight fluorine substituents).

In some embodiments, more than one type of ligand are employed. For example, in some embodiments, a first type of ligand and a second type of ligand are employed, wherein the second type of ligand is different than the first type of ligand. The two or more types of ligands may be provided in any suitable ratio. As described herein, a ligand may comprise any combination of unsaturated N-heterocyclic aromatic groups (e.g., at least one pyrazole, at least two pyrazoles, etc.).

According to certain embodiments, the plurality of metal atoms are coordinated with at least one ligand (e.g., each metal ion is coordinated with at least one ligand). In some embodiments, each of the metal atoms are coordinated with at least one ligand comprising N-substituted aromatic groups (e.g., pyrazoles). In some embodiments, at least some of the metal atoms are associated with two, three, or four ligands, and each of those ligands are individually associated with one, two, three, or four metal atoms. In certain embodiments, at least some of the metal atoms are associated with two ligands, and each of those ligand is individually associated with two metal atoms. In some embodiments, at least some of the metal atoms are associated with three ligands, and each of those ligand is individually associated with three metal atoms. In some embodiments, at least some of the metal atoms are associated with four ligands, and each of those ligand is individually associated with two metal atoms. In some embodiments, a ligand is charged.

Figure 3:
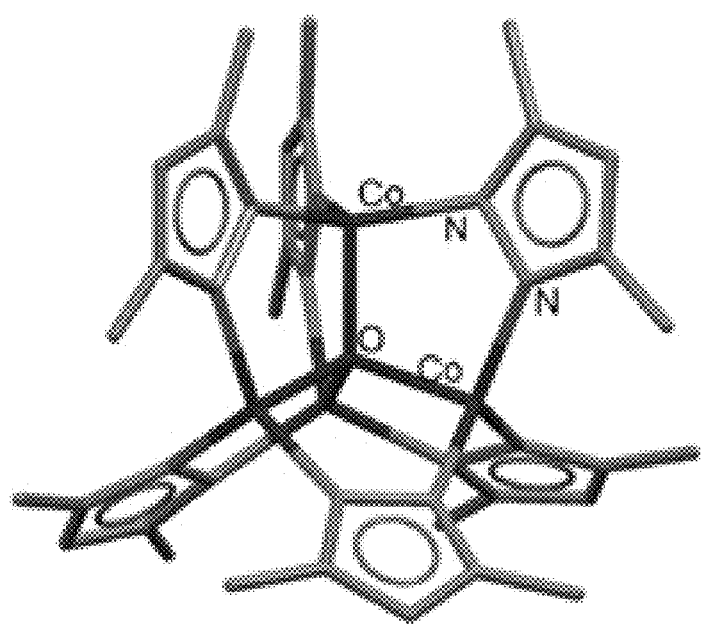
FIG. 3 shows the core of an exemplary embodiment of a secondary building unit of a MOF compound.

In an exemplary embodiment, the core coordination environment of a MOF compound (abbreviated MFU-1 in FIG. 3) is shown in FIG. 3, wherein the MOF compound core comprises four cobalt atoms are bound to six 1,4-bis[(3,5-dimethyl)-pyrazol-4-yl]benzene ligands.

According to some embodiments, the MOF compound comprises a plurality of pores. In certain embodiments, the plurality of pores are between repeating coordination entities of the MOF compound extending in one, two, or three dimensions. In certain embodiments, the plurality of pores are between repeating coordination entities of a plurality of ligands and/or a plurality of metal atoms. In certain embodiments, the coordination environment of the plurality of metals and/or plurality of ligands can influence and/or dictate the size of shape of the plurality of pores. Resultantly, according to certain embodiments, the internal environment (e.g., size, shape) of the plurality of pores can be controlled through the selection of the plurality of metal atoms and/or plurality of ligands.

According to certain embodiments, the plurality of pores can be used to store guest molecules (e.g., solvents, gases). For example, in certain embodiments, the MOF compound comprising a plurality of pores can be used to store $H_2$ gas from dehydrogenation reactions (e.g., step 102 in FIG. 1). In some embodiments, the stored $H_2$ gas can later be used for hydrogenation reactions (e.g., step 108 in FIG. 1). According to certain embodiments, the plurality of pores can be used to store the metal catalytic compounds, as described in more detail herein.

The MOF compounds may be synthesized using methods known in the art. Methods of synthesizing MOF compounds are described in, for example, *Angew. Chem. Int. Ed.*, 2009, 48, 7546. For example, in certain embodiments, a method of synthesizing a MOF compound comprises exposing a plurality of metal atoms to a plurality of precursor ligands to form a MOF comprising a portion of the plurality of metal atoms each coordinated with at least one ligand. Methods of synthesizing the MOF compound may comprise a microwave synthesis.

The plurality of metal atoms and the plurality of ligands may be provided in any suitable amounts. In some embodiments, the mole ratio of the metal ion to the ligand is based upon the coordination of the metal ion to the ligand. For example, in embodiments where the ligand is coordinated with three metal atoms, and each metal ion is associated with two ligands, the mole ratio of the metal ion to the ligand is at least 3:2. As another example, in embodiments where the ligand is coordinated with two metal atoms, and each metal ion is associated with one ligand, the mole ratio of the metal ion to the precursor ligand is about 2:1. In some embodiments, the ligand is providing in slight molar excess.

Any suitable solvent may be utilized in the synthetic methods of forming the MOF compounds described herein. Non-limiting examples of solvents include water, methanol, ethanol, propanol, benzene, p-cresol, toluene, xylene, diethyl ether, glycol, diethyl ether, petroleum ether, hexane, cyclohexane, pentane, methylene chloride, chloroform, carbon tetrachloride, dioxane, tetrahydrofuran (THF), dimethyl sulfoxide (DMSO), dimethylformamide, hexamethyl-phosphoric triamide, ethyl acetate, pyridine, triethylamine, picoline, mixtures thereof, or the like.

The MOF compounds may be synthesized at any suitable temperature. In some cases, the synthesis of the MOF compounds is carried out at about room temperature (e.g., about 25° C., about 20° C., between about 20° C. and about 25° C., or the like). In some cases, however, the synthesis of MOF compounds is carried out at temperatures below or above room temperature. In certain embodiments, the synthesis of the MOF compounds is carried out at greater than or equal to about 20° C., greater than or equal to about 25° C., greater than or equal to about 50° C., greater than or equal to about 75° C., greater than or equal to about 100° C., greater than or equal to about 125° C., greater than or equal to about 150° C., or greater than or equal to about 175° C. In some embodiments, the synthesis of the MOF compounds is carried out at less than or equal to 200° C., less than or equal to 175° C., less than or equal to 150° C., less than or equal to 125° C., less than or equal to 100° C., less than or equal to 75° C., less than or equal to 50° C., or less than or equal to 25° C. Combinations of the above-recited ranges are also possible. For example, in some embodiments, the synthesis of MOF compounds is carried at a temperature between about 25° C. and about 200° C., or between about 25° C. and about 150° C., or between about 50° C. and about 200° C., or between about 50° C. and about 150° C., or between about 100° C. and about 150° C.

In some embodiments, the MOF compounds is synthesized in an inert atmosphere. For example, the reactions may be carried out in or under an inert nitrogen or argon atmosphere (e.g., using standard Schlenk techniques and/or in an inert-atmosphere glovebox).

The MOF compounds synthesized using the methods described herein may be purified using techniques known to those of ordinary skill in the art. In some embodiments, a synthesized MOF is washed, sometimes involving a Soxhlet extractor, boiled, and/or sonicated (e.g., to remove excess starting materials).

In some embodiments, a precursor MOF composition comprises a plurality of precursor metal catalytic compounds. In certain embodiments, the plurality of precursor metal catalytic compounds comprises any suitable metal. For example, according to some embodiments, the plurality of precursor metal catalytic compounds comprise ruthenium, iridium, and/or manganese. In some embodiments, the precursor metal catalytic compounds are $Ru^{2+}$ compounds. In certain embodiments, the precursor metal catalytic compound is $RuCl_2X$, wherein X is a neutral bidentate ligand. Non-limiting examples of neutral bidentate ligands include norbornadiene (nbd) and 1,5-cyclooctadiene (COD). In some embodiments, the precursor metal catalytic compound is $[RuCl_2(nbd)]_2$, $[RuCl_2(COD)]_2$, $Ru_2Cl_4(CO)_6$, $RuCl_3$, or $RuCl_2(DMSO)_4$, though other related ruthenium compounds may be suitable. In certain embodiments, the precursor metal catalytic compound (e.g., $[RuCl_2(nbd)]_2$) is incorporated into the MOF compound in a different form than the starting material. For example, in certain embodiments, the precursor metal catalytic compound is incorporated into the MOF compound as metal-containing nanoparticles (e.g., ruthenium nanoparticles).

In some embodiments, a catalytic MOF composition comprises a plurality of metal catalytic compounds. In certain embodiments, the plurality of metal catalytic compounds comprise any suitable metal. For example, according to some embodiments, the plurality of metal catalytic compounds comprise ruthenium, iridium, and/or manganese. In some embodiments, the metal catalytic compounds are $Ru^0$ compounds. As noted above, in some embodiments, the metal catalytic compounds are formed via reduction of precursor metal catalytic compounds following incorporation of the precursor metal catalytic compound into the MOF compound. For example, the precursor metal catalytic compound may comprises $Ru^{2+}$, and the resulting metal catalytic compound may comprise $Ru^0$ (e.g., ruthenium metal nanoparticles) that have been formed via reduction of the precursor metal catalytic compounds. According to certain embodiments, as the precursor metal catalytic compounds (e.g., $Ru^{2+}$) are reduced to metal catalytic compounds (e.g., $Ru^0$, the metal catalytic compounds agglomerate into nanoparticles (e.g., $Ru^0$) nanoparticles. Metal catalytic nanoparticles are explained in greater detail below.

In certain embodiments, the precursor metal catalytic compounds are reduced to metal catalytic compounds by the addition of a base (e.g., ethoxide, hydroxide, etc.). In some embodiments, the precursor metal catalytic compounds are reduced to metal catalytic compounds by a reducing agent. For example, in certain embodiments, the precursor metal catalytic compounds are reduced to metal catalytic compounds by the addition of $H_2$, $BH_3$, $NH_3$, or $NaBH_4$.

Figure 2:
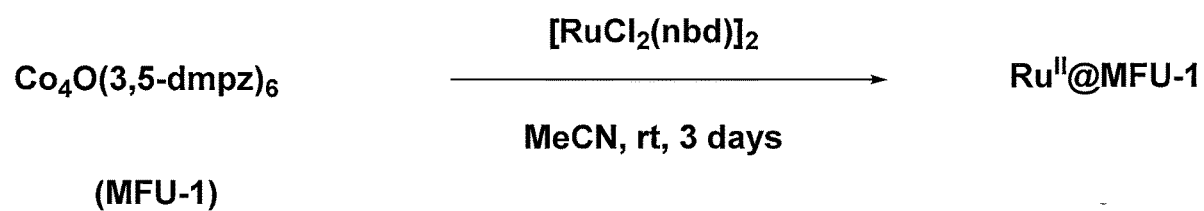
FIG. 2 shows an exemplary embodiment of a precursor metal catalytic compound being added to an MOF compound to form a precursor MOF composition.

According to certain embodiments, the plurality of metal catalytic compounds are mixed with a MOF compound to form the catalytic MOF composition, or, a plurality of precursor metal catalytic compounds are mixed with a MOF compound to form a precursor MOF composition. For example, in some embodiments, a metal catalytic compound or a precursor metal catalytic compound is added to a solution containing the MOF compound (e.g., a suspension) with stirring to incorporate the metal catalytic compound into the MOF compound (e.g., thereby forming a catalytic MOF composition or a precursor MOF composition). In certain embodiments, the metal catalytic compound or precursor metal catalytic composition is mixed in any suitable solvent (e.g., acetonitrile) at any suitable temperature (e.g., room temperature) to incorporate the metal catalytic compound or precursor metal catalytic compound into the MOF compound, thereby forming the catalytic MOF composition or the precursor MOF composition, respectively. FIG. 2 shows an exemplary embodiment of a precursor metal catalytic compound being added to an MOF compound to form a precursor MOF composition. For example, as shown in FIG. 2, the precursor metal catalytic compound [RuCl$_2$(nbd)]$_2$ is added to MFU-1 in acetonitrile at room temperature for three days to generate the MOF composition Ru@MFU-1. According to certain embodiments, Ru@MFU-1 is a precursor MOF composition and can be activated to a catalytic MOF composition by the methods described herein.

Figure 5A:
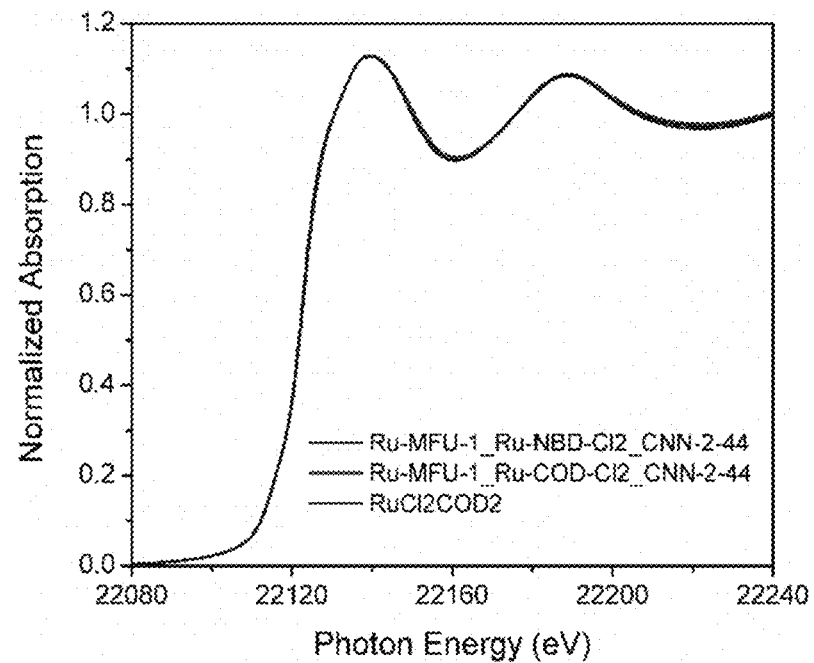
FIG. 5A shows, according to certain embodiments, X-ray absorption near edge structure spectra of an exemplary MOF composition compared to $Ru^{2+}$ standards and Ru foil (absorption versus photon energy)
Figure 5B:
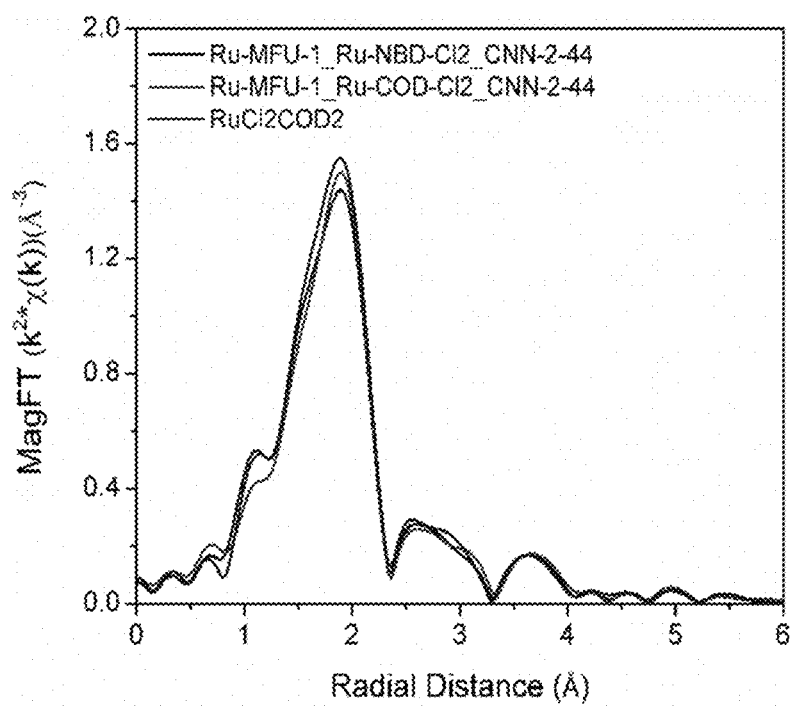
FIG. 5B shows, according to certain embodiments, X-ray absorption near edge structure spectra of an exemplary MOF composition compared to $Ru^{2+}$ standards and Ru foil (radial distance versus MagFT)
Figure 6A:
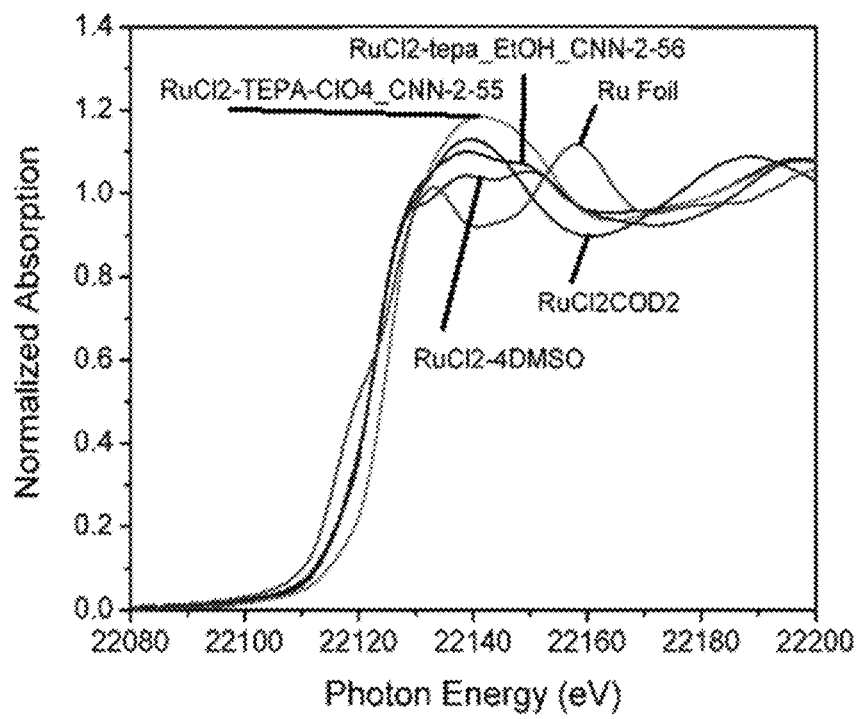
FIG. 6A shows, according to some embodiments, extended X-ray absorption fine structure spectra of an exemplary MOF composition compared to $Ru^{2+}$ standards and Ru foil (absorption versus photon energy)
Figure 6B:
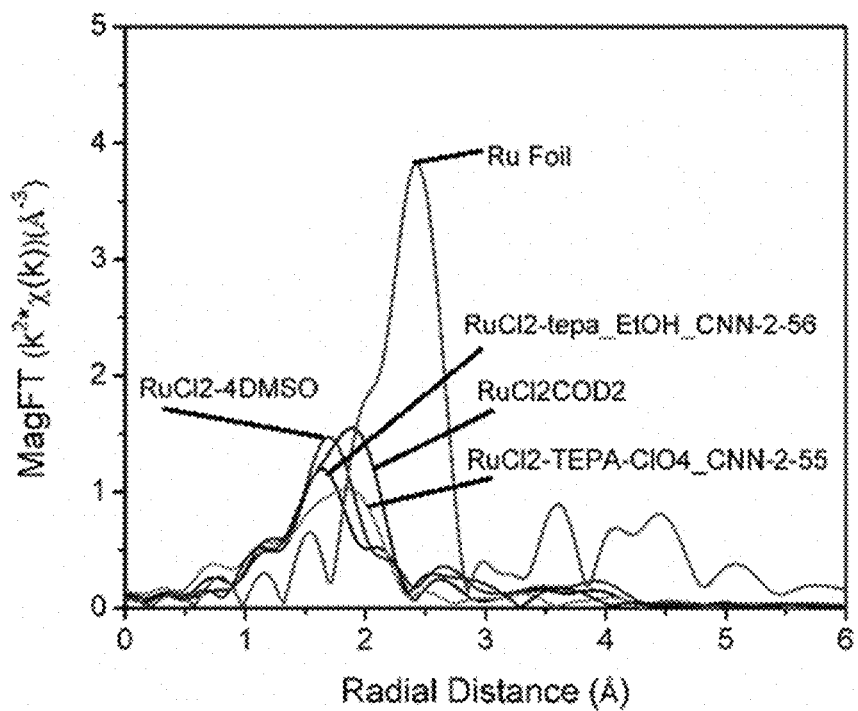
FIG. 6B shows, according to certain embodiments, extended X-ray absorption fine structure spectra of an exemplary MOF composition compared to $Ru^{2+}$ standards and Ru foil (radial distance versus MagFT)

In certain embodiments, the incorporation of a metal catalytic compound or a catalytic metal catalytic compound into the MOF compound to form a catalytic MOF composition or a precursor MOF composition can be confirmed by mass spectrometry techniques (e.g., inductively coupled plasma mass spectrometry), or by X-ray photoelectron spectroscopy and/or X-ray absorption spectroscopy. For example, FIG. 5A and FIG. 5B show X-ray absorption near edge structure (XANES) spectra of Ru@MFU-1 compared to Ru$^{II}$ standards and Ru foil. FIG. 6A and FIG. 6B show extended X-ray absorption fine structure (EXAFS) of Ru@MFU-1 compared to Rd$^{II}$ standards and Ru foil.

According to certain embodiments, the crystallinity of the MOF compound is preserved during incorporation of the plurality of precursor metal catalytic compounds or metal catalytic compounds (e.g., ruthenium-containing compounds). For example, in some embodiments, no metal exchange is observed (e.g., the metal atoms of the MOF compound, such as Co or Ni, are not exchanged with a metal ion from the metal catalytic compound or precursor thereof, such as Ru). Those of ordinary skill in the art would be aware of methods and systems for determining whether crystallinity of a compound is preserved, for example, by comparing the crystallinity of the MOF compound before and after incorporation. A non-limiting method for determining is via powder X-ray diffraction. For example, see FIG. 4, which shows, according to certain embodiments, a powder X-ray diffraction pattern of a precursor MOF composition.

In certain embodiments, the plurality of precursor metal catalytic compounds or metal catalytic compounds (e.g., ruthenium-containing compounds) are contained in the plurality of pores of the MOF compound. According to certain embodiments, the plurality of metal catalytic compounds are contained in the plurality of pores of the MOF compound that are between repeating coordination entities of the MOF compound extending in one, two, or three dimensions. In certain embodiments, the plurality of metal catalytic compounds are contained in the plurality of pores of the MOF compound that are between repeating coordination entities of a plurality of ligands and/or a plurality of metal atoms. In certain embodiments, the precursor metal catalytic compounds or metal catalytic compounds are contained in the plurality of pores in the form of polymeric chains of the precursor metal catalytic compound or metal catalytic compounds, respectively.

The amount of precursor metal catalytic compounds incorporated into the MOF compound may be any suitable amount (e.g., 1 wt. %, or 2 wt. %, or 3 wt. %, or 4 wt. %, or 5 wt. %. relative to the plurality of metal atoms in the MOF compound). In certain embodiments, a high porosity (e.g., 400 cm$^3$/g, 500 cm$^3$/g, 600 cm$^3$/g) is maintained after incorporation of the precursor metal catalytic compound into the plurality of pores.

As described above, in certain embodiments the precursor MOF composition comprises a MOF compound and a plurality of precursor metal catalytic compounds contained in the plurality of pores of the MOF compound. In some embodiments, the MOF compound comprises a plurality of metal atoms (e.g., Co atoms or Ni atoms), and at least a portion of the plurality of metal catalytic compounds and at least a portion of the metal atoms bond with each other upon activation of the precursor MOF composition. For example, in certain embodiments, the MOF precursor composition is at least partially activated when at least a portion of the precursor metal catalytic compounds are reduced to metal catalytic compounds, and at least a portion of the metal catalytic compounds bond to at least a portion of the metal atoms (e.g., Co atoms or Ni atoms). In certain embodiments, the metal catalytic compound comprises at least a portion of the metal atoms. In certain non-limiting embodiments, the plurality of precursor metal catalytic compounds comprises Ru$^{2+}$. In some such embodiments, the precursor metal catalytic compounds is reduced to form metal catalytic compounds comprising Ru$^0$, as described herein. In certain embodiments, in addition to the reduction of the metal catalytic compounds, the metal atoms of the MOF compound (e.g., Co ions or Ni ions) are also be reduced (e.g., by a base and/or reducing agent). For example, in some embodiments, the MOF precursor composition is at least partially activated when at least a portion of the cobalt or nickel ions are reduced to Co$^0$ or Ni$^0$ atoms. In certain other embodiments, the MOF precursor composition is at least partially activated when at least a portion of the cobalt or nickel ions are reduced to cobalt or nickel atoms with an oxidation state greater than 0. In certain embodiments, the metal catalytic compounds comprise Ru$^0$ nanoparticles that bond to at least a portion of the reduced metal atoms of the MOF compound (e.g., Co$^0$ or Ni$^0$ atoms). In some embodiments, at least a portion of the plurality of metal catalytic compounds forms a bond with at least a portion of the metal atoms (e.g., to form a plurality of nanoparticles). In certain embodiments, the nanoparticles are in the form of an alloy. In some embodiments, the alloy is a Ni-based alloy or a Co-based alloy. In some embodiments, the alloy is a Ru-based alloy. In certain non-limiting embodiments, the alloy comprises Ru$_x$Co$_{x-1}$ or Ru$_x$Ni$_{x-1}$ nanoparticles. Resultantly, in certain embodiments, the metal catalytic compound comprises Ru$_x$Co$_{x-1}$ or Ru$_x$Ni$_{x-1}$ nanoparticles. According to some embodiments, the metal catalytic compound (e.g., Ru$_x$Co$_{x-1}$ or Ru$_x$Ni$_{x-1}$ nanoparticles) converts at least a portion of the one or more first alcohols to one or more second alcohols. In certain embodiments, the catalytic activity of the metal catalytic nanoparticles is due at least in part to surface ligands on the nanoparticles, the crystal packing of the nanoparticles, or a particular nanoparticle size.

According to certain embodiments, the bond between at least a portion of the plurality of metal catalytic compounds and at least a portion of the metal atoms (e.g., Co atoms or Ni atoms) is any of a variety of suitable bonds. For example, in certain embodiments, at least a portion of the plurality of metal catalytic compounds and at least a portion of the metal atoms are bound by non-covalent interactions, including electrostatic interactions (e.g., ionic interactions, hydrogen bonding), pi stacking interactions, van der Waals forces, and/or hydrophobic interactions. In some embodiments, at least a portion of the plurality of metal catalytic compounds and at least a portion of the metal atoms are bound by covalent interactions (e.g., sigma bonding, pi bonding). Other bonding interactions and/or associations are also possible.

The plurality of nanoparticles may be any of a variety of suitable sizes. For example, in certain embodiments, the plurality of nanoparticles have an average characteristic dimension, such as an average maximum diameter. In some embodiments, the plurality of nanoparticles have an average maximum diameter that is greater than or equal to 1.0 nm, greater than or equal to 2.0 nm, greater than or equal to 3.0 nm, greater than or equal to 4.0 nm, greater than or equal to 5.0 nm, greater than or equal to 10 nm, greater than or equal to 15 nm, greater than or equal to 20 nm, greater than or equal to 25 nm, greater than or equal to 50 nm, greater than or equal to 75 nm, greater than or equal to 100 nm, greater than or equal to 125 nm, greater than or equal to 150 nm, greater than or equal to 175 nm, or greater than or equal to 200 nm. In some embodiments, the plurality of nanoparticles have an average maximum diameter of less than or equal to 250 nm, less than or equal to 200 nm, less than or equal to 175 nm, less than or equal to 150 nm, less than or equal to 125 nm, less than or equal to 100 nm, less than or equal to 75 nm, less than or equal to 50 nm, less than or equal to 25 nm, less than or equal to 20 nm, less than or equal to 15.0 nm, less than or equal to 10.0 nm, less than or equal to 5.0 nm, less than or equal to 4.0 nm, less than or equal to 3.0 nm, or less than or equal to 2.0 nm. Combinations of the above listed ranges are also possible (e.g., the plurality of nanoparticles have an average maximum diameter of greater than or equal to 1.0 nm and less than or equal to 250 nm, the plurality of nanoparticles have an average maximum diameter of greater than or equal to 25 nm and less than or equal to 100 nm). Other ranges are also possible. The size (e.g., average characteristic dimension) of the nanoparticles may be determined by scanning electron microscopy (SEM).

In certain embodiments, the size (e.g., average characteristic dimension) of the nanoparticles is dependent on multiple factors, including certain reaction conditions. For example, in certain embodiments, the size of the nanoparticles is dependent on the temperature of the upgrading reaction where the MOF composition is used to upgrade alcohols. In some embodiments, the size of the nanoparticles is dependent on the substrate (e.g., the one or more first alcohols). In some embodiments, the size of the nanoparticles is dependent on the amount of base (e.g., sodium ethoxide) used during the upgrading reaction. Other factors may affect the size of the nanoparticles.

Without wishing to be bound by theory, in certain embodiments the MOF composition comprises a plurality of particles comprising a metal catalytic compound, the metal catalytic compound comprising a nickel-based alloy with Ru or a cobalt-based alloy with Ru. In certain embodiments, the plurality of particles comprise microparticles (e.g., particles with a maximum characteristic dimension of greater than or equal to 1 micrometer) and/or nanoparticles (e.g., particles with a maximum characteristic dimension of less than 1 micrometer).

According to certain embodiments, at least a portion of the plurality of nanoparticles are released from the MOF compound. For example, in some embodiments, the metal catalytic compound comprises $Ru_xCo_{x-1}$ or $Ru_xNi_{x-1}$ nanoparticles that are released from the MOF compound. In some embodiments, the $Ru_xCo_{x-1}$ or $Ru_xNi_{x-1}$ nanoparticles are in the form of an alloy. In some embodiments wherein at least a portion of the plurality of nanoparticles are released from the MOF compound, the plurality of nanoparticles substantially retains its reactivity to convert at least a portion of the one or more first alcohols to one or more second alcohols. For example, in some embodiments, the reactivity of the plurality of nanoparticles to convert at least a portion of the one or more first alcohols to one or more second alcohols does not decrease by more than 50%, more than 40%, more than 30%, more than 20%, more than 10%, more than 5%, more than 2%, or more than 1%.

According to certain embodiments, a method of catalytically converting one or more first alcohols is described. In certain embodiments, the method of catalytically converting one or more first alcohols comprises upgrading one or more first alcohols. In certain embodiments, the method comprises exposing one or more first alcohols to the MOF composition and/or the plurality of nanoparticles associated with the MOF composition. For example, in some embodiments, the method comprises exposing one or more first alcohols to the plurality of nanoparticles comprising at least a portion of the metal catalytic compound, the metal catalytic compound comprising a plurality of metal atoms (e.g., Co atoms or Ni atoms). In some embodiments, the method further comprises converting the one or more first alcohols to one or more second alcohols, wherein the one or more second alcohols has a greater number of carbon atoms than the one or more first alcohols.

In certain non-limiting embodiments, a method comprises exposing the MOF composition and/or the plurality of nanoparticles associated with the MOF composition to ethanol and converting ethanol to 1-butanol.

The one or more first alcohols may be any of a variety of suitable alcohols. In certain embodiments, the one or more first alcohols comprises methanol, ethanol, propanol (e.g., 1-propanol), butanol (e.g., 1-butanol), pentanol (e.g., 1-pentanol), and/or combinations thereof. Other alcohols are also possible.

The one or more second alcohols may be any of a variety of suitable alcohols. In some embodiments, the one or more second alcohols comprises propanol (e.g., 1-propanol, 2-methyl-1-propanol, butanol (e.g., 1-butanol), 2-methyl-1-butanol, 2-ethyl-butanol, pentanol (e.g., 1-pentanol), 2-methyl-1-petanol, hexanol (e.g., 1-hexanol), 2-ethyl-1-hexanol, heptanol (e.g., 1-heptanol), 3-propyl-1-heptanol, and/or combinations thereof. Other alcohols are also possible.

Any combination of one or more first alcohols and one or more second alcohols may be employed, provided that the one or more second alcohols have a greater number of carbon atoms than the one or more first alcohols. In certain embodiments, the one or more first alcohols comprises ethanol and the one or more second alcohols comprises butanol (e.g., 1-butanol). In some embodiments, the one or more first alcohols comprises 1-butanol and the one or more second alcohols comprises 2-ethyl-hexanol. In certain embodiments, the one or more first alcohols comprises ethanol and 1-butanol and the one or more second alcohols comprises 1-hexanol, 2-ethyl-butanol, and 2-ethyl-hexanol.

In certain embodiments, the catalytic MOF composition catalyzes the conversion of the one or more first alcohols (e.g., ethanol and/or 1-butanol) to one or more second alcohols (e.g., 1-butanol, 1-hexanol, 2-ethyl-butanol, 2-ethyl-hexanol, and/or combinations thereof).

In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with high selectivity. For example, in some embodiments, one or more second alcohols (e.g., 1-butanol) is formed in the presence of a catalytic MOF composition with a selectivity of at least about 80%, at least about 85%, at least about 90%, at least about 91%, at least about 92%, at least about 93%, at least about 94%, at least about 95%, at least about 96%, at least about 97%, at least about 98%, at least about 99%, at least about 99.5%, at least about 99.8%, or at least about 99.9%. In certain embodiments, one or more second alcohols (e.g., 1-butanol) is formed in the presence of a catalytic MOF composition with a selectivity of 100%. In certain embodiments, one or more second alcohols (e.g., 1-butanol) is formed in the presence of a catalytic MOF composition with a selectively of less than or equal to 100%, less than or equal to 99.9%, less than or equal to 99.8%, less than or equal to 99.5%, less than or equal to 99%, less than or equal to 98%, less than or equal to 97%, less than or equal to 96%, less than or equal to 95%, less than or equal to 94%, less than or equal to 93%, less than or equal to 92%, less than or equal to 91%, less than or equal to 90%, or less than or equal to 85%. Combinations of the above-recited ranges are also possible (e.g., one or more second alcohols is formed in the presence of a catalytic MOF composition with a selectively at least 80% and less than or equal to 100%, one or more second alcohols is formed in the presence of a catalytic MOF composition with a selectively at least 95% and less than or equal to 99.5%).

Those of ordinary skill in the art will be aware of methods and techniques for determining selectivity. In some embodiments, the selectivity of a reaction for 1-butanol may be determined by determining the percent by weight of 1-butanol based on the total amount of products (e.g., other butanols, longer chain alcohols, and/or other side products) produced. In certain embodiments, the selectivity of a reaction for 1-butanol may be determined by determining the mole percent of 1-butanol based on the total amount of products (e.g., other butanols, longer chain alcohols, and/or other side products) produced. For example, gas chromatography may be used to determine the weight percentage and/or mole percentage of 1-butanol versus the total amount of product produced (e.g., as compared to an internal standard). In some embodiments, gas chromatography is used to determine the weight percentage and/or mole percentage of 1-butanol versus the total amount of butanol produced (e.g., as compared to an internal standard).

According to certain embodiments, the catalytic MOF composition and/or the plurality of nanoparticles associated with the MOF composition catalyzes the conversion of one or more first alcohols to one or more second alcohols (e.g., ethanol to 1-butanol) with high selectivity such that only minor side products are observed. For example, in certain embodiments, minor side products observed during the catalytic conversion of ethanol to butanol include 2-ethyl-1-butanol and/or isomers of 1-hexanol. According to some embodiments, the minor side products are formed in low percentages compared to the one or more second alcohols. For example, the minor side products may be formed in less than or equal to 5 mole percent (mol. %), less than or equal to 4 mol. %, less than or equal to 3 mol. %, less than or equal to 2 mol. %, or less than or equal to 1 mol. % compared to the one or more second alcohols. In some embodiments, the minor side products are formed in greater than or equal to 0.1 mol. %, greater than or equal to 1 mol. %, greater than or equal to 2 mol. %, greater than or equal to 3 mol. %, or greater than or equal to 4 mol. % compared to the one or more second alcohols. Combinations of the above recited ranges are also possible (e.g., the minor side products are formed in less than or equal to 5 mol. % and greater than or equal to 0.1 mol. %, the minor side products are formed in less than or equal to 3 mol. % and greater than or equal to 2 mol. %).

According to certain embodiments, the MOF composition and/or the plurality of nanoparticles associated with the MOF composition catalyzes the conversion of the one or more first alcohols (e.g., ethanol) to the one or more second alcohols (e.g. 1-butanol) with a particular turnover number (TON). Turnover number, as used herein, refers to the number of moles of first alcohol (e.g., ethanol) consumed per moles of active metal centers (e.g., the moles of the metal with respect to the metal catalytic compound) in the catalytic MOF composition and/or catalytic plurality of nanoparticles. For example, in some embodiments, wherein the active metal center is a ruthenium ion, the TON refers to the number of moles of the first alcohol consumed per moles of active metal center (e.g., ruthenium). In some embodiments, the one or more second alcohols is formed in the presence of the catalytic MOF composition at a turnover number of at least about 1,000, at least about 2,000, at least about 4,000, at least about 5,000, at least about 6,000, at least about 8,000, at least about 10,000, at least about 15,000, at least about 20,000, at least about 50,000, at least about 100,000, at least about 200,000, at least about 400,000, at least about 500,000, at least about 600,000, at least about 700,000, or at least about 800,000 per moles of active metal centers (e.g., $Ru^{-1}$) measured at 170° C. In certain embodiments, the one or more second alcohols is formed in the presence of the catalytic MOF composition at a turnover number of less than or equal to about 900,000, less than about equal to about 800,000, less than about equal to about 700,000, less than or equal to about 600,000, less than or equal to about 500,000, less than or equal to about 400,000, less than or equal to about 200,000, less than or equal to about 100,000, less than or equal to about 50,000, less than or equal to about 20,000, less than or equal to about 10,000, less than or equal to about 8,000, less than or equal to about 6,000, less than or equal to about 5,000, less than or equal to about 4,000, or less than or equal to about 2,000 per moles of active metal centers (e.g., $Ru^{-1}$) measured at 170° C. Combinations of the above referenced ranges are also possible (e.g., the one or more second alcohols is formed in the presence of the catalytic MOF composition at a turnover number of between about 5,000 and about 100,000 per moles of active metal centers (e.g., $Ru^{-1}$) measured at 170° C., the one or more second alcohols is formed in the presence of the catalytic MOF composition at a turnover number of between about 1,000 and about 900,000 per moles of active metal centers (e.g., $Ru^{-1}$) measured at 170° C.).

According to certain embodiments, the MOF composition and/or the plurality of nanoparticles associated with the MOF composition catalyzes the conversion of the first alcohol (e.g., ethanol) to the second alcohol (e.g. 1-butanol) with a particular turnover frequency (TOF). As used herein, the turnover frequency refers to the number of moles of the first alcohol consumed per moles of active metal centers in the catalytic MOF composition and/or catalytic plurality of nanoparticles per time. Catalytic reaction times are explained further herein. In some embodiments, the second alcohol is formed in the presence of the catalytic MOF composition at a turnover frequency of at least about 100, at least about 500, at least about 1,000, at least about 2,000, at least about 3,000, at least about 4,000, at least about 5,000, at least about 10,000, or at least about 11,000 per moles of active metal center per hour (e.g., $Ru^{-1}h^{-1}$) measured at 170° C. According to certain embodiments, the second alcohol is formed in the presence of the catalytic MOF composition at a turnover frequency of less than about 12,000, less than about 11,000, less than about 10,000, less than about 5,000, less than about 4,000, less than about 3,000, less than about 2,000, less than about 1,000, or less than about 500 per moles of active metal center per hour (e.g., $Ru^{-1}h^{-1}$) measured at 170° C. Combinations of the above referenced ranges are also possible (e.g., the second alcohol is formed in the presence of the catalytic MOF composition at a turnover frequency of between about 500 and about 5,000 per moles of active metal center per hour (e.g., $Ru^{-1}h^{-1}$) measured at 170° C., the second alcohol is formed in the presence of the catalytic MOF composition at a turnover frequency of between about 100 and about 12,000 per moles of active metal center per hour (e.g., $Ru^{-1}h^{-1}$) measured at 170° C.).

In some embodiments, the number of moles of one or more first alcohols (e.g., ethanol) that have been converted to one or more second alcohols (e.g., butanol) can be determined, for example, using gas chromatography after reacting the one or more first alcohols with the catalytic MOF composition. Those of ordinary skill in the art will be aware of methods and systems for determining the number of moles of active metal centers. For example, in embodiments wherein the active metal center is ruthenium and the MOF also comprises cobalt, the number of moles of ruthenium may be determined based at least in part on the ratio of ruthenium to cobalt (e.g., based on the structure of the MOF compound) and the weight of the MOF compound used. Other methods of determining the number of moles of active metal centers include, for example, using X-ray photoelectron spectroscopy, X-ray absorption spectroscopy, and/or inductively coupled plasma mass spectrometers.

In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50%, at least about 60%, at least about 70%, at least about 75%, at least about 80%, at least about 85%, at least about 90%, at least about 95%, at least about 99% and a turnover number of at least about 1,000 per moles of active metal centers (e.g., $Ru^{-1}$) measured at 170° C. In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of less than or equal to about 100%, less than or equal to about 99%, less than or equal to about 95%, less than or equal to about 90%, less than or equal to about 85%, less than or equal to about 80%, less than or equal to about 75%, less than or equal to about 70%, or less than or equal to about 60% and a turnover number of at least about 1,000 per moles of active metal centers (e.g., $Ru^{-1}$) measured at 170° C. Combinations of the above recited ranges are also possible. For example, in certain embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50% and less than or equal to about 100% and a turnover number of at least about 1,000 per moles of active metal centers (e.g., $Ru^{-1}$) measured at 170° C., the catalytic MOF composition and/or the plurality of nanoparticles associated with the MOF composition n catalyzes the conversion of one or more first alcohols (e.g., ethanol) to one or more second alcohols (e.g., 1-butanol) with a selectivity of at least about 85% and less than or equal to about 99% and a turnover number of at least about 1,000 per moles of active metal centers (e.g., $Ru^{-1}$) measured at 170° C.

In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50%, at least about 60%, at least about 70%, at least about 75%, at least about 80%, at least about 85%, at least about 90%, at least about 95%, at least about 99% and a turnover number of at least about 5,000 per moles of active metal centers (e.g., $Ru^{-1}$) measured at 170° C. In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of less than or equal to about 100%, less than or equal to about 99%, less than or equal to about 95%, less than or equal to about 90%, less than or equal to about 85%, less than or equal to about 80%, less than or equal to about 75%, less than or equal to about 70%, or less than or equal to about 60% and a turnover number of at least about 5,000 per moles of active metal centers (e.g., $Ru^{-1}$) measured at 170° C. Combinations of the above recited ranges are also possible. For example, in certain embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50% and less than or equal to about 100% and a turnover number of at least about 5,000 per moles of active metal centers (e.g., $Ru^{-1}$) measured at 170° C., the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 85% and less than or equal to about 99% and a turnover number of at least about 5,000 per moles of active metal centers (e.g., $Ru^{-1}$) measured at 170° C.

In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50%, at least about 60%, at least about 70%, at least about 75%, at least about 80%, at least about 85%, at least about 90%, at least about 95%, at least about 99% and a turnover number of at least about 10,000 per moles of active metal centers (e.g., $Ru^{-1}$) measured at 170° C. In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of less than or equal to about 100%, less than or equal to about 99%, less than or equal to about 95%, less than or equal to about 90%, less than or equal to about 85%, less than or equal to about 80%, less than or equal to about 75%, less than or equal to about 70%, or less than or equal to about 60% and a turnover number of at least about 10,000 per moles of active metal centers (e.g., $Ru^{-1}$) measured at 170° C. Combinations of the above recited ranges are also possible. For example, in certain embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50% and less than or equal to about 100% and a turnover number of at least about 10,000 per moles of active metal centers (e.g., $Ru^{-1}$) measured at 170° C., the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 85% and less than or equal to about 99% and a turnover number of at least about 10,000 per moles of active metal centers (e.g., $Ru^{-1}$) measured at 170° C.

In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50%, at least about 60%, at least about 70%, at least about 75%, at least about 80%, at least about 85%, at least about 90%, at least about 95%, at least about 99% and a turnover number of at least about 20,000 per moles of active metal centers (e.g., $Ru^{-1}$) measured at 170° C. In some embodiments, the catalytic MOF composition and/or the plurality of nanoparticles associated with the MOF composition n catalyzes the conversion of one or more first alcohols (e.g., ethanol) to one or more second alcohols (e.g., 1-butanol) with a selectivity of less than or equal to about 100%, less than or equal to about 99%, less than or equal to about 95%, less than or equal to about 90%, less than or equal to about 85%, less than or equal to about 80%, less than or equal to about 75%, less than or equal to about 70%, or less than or equal to about 60% and a turnover number of at least about 20,000 per moles of active metal centers (e.g., $Ru^{-1}$) measured at 170° C. Combinations of the above recited ranges are also possible. For example, in certain embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50% and less than or equal to about 100% and a turnover number of at least about 20,000 per moles of active metal centers (e.g., $Ru^{-1}$) measured at 170° C., the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 85% and less than or equal to about 99% and a turnover number of at least about 20,000 per moles of active metal centers (e.g., $Ru^{-1}$) measured at 170° C.

In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50%, at least about 60%, at least about 70%, at least about 75%, at least about 80%, at least about 85%, at least about 90%, at least about 95%, at least about 99% and a turnover number of at least about 50,000 per moles of active metal centers (e.g., $Ru^{-1}$) measured at 170° C. In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of less than or equal to about 100%, less than or equal to about 99%, less than or equal to about 95%, less than or equal to about 90%, less than or equal to about 85%, less than or equal to about 80%, less than or equal to about 75%, less than or equal to about 70%, or less than or equal to about 60% and a turnover number of at least about 50,000 per moles of active metal centers (e.g., $Ru^{-1}$) measured at 170° C. Combinations of the above recited ranges are also possible. For example, in certain embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50% and less than or equal to about 100% and a turnover number of at least about 50,000 per moles of active metal centers (e.g., $Ru^{-1}$) measured at 170° C., the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 85% and less than or equal to about 99% and a turnover number of at least about 50,000 per moles of active metal centers (e.g., $Ru^{-1}$) measured at 170° C.

In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50%, at least about 60%, at least about 70%, at least about 75%, at least about 80%, at least about 85%, at least about 90%, at least about 95%, at least about 99% and a turnover number of at least about 100,000 per moles of active metal centers (e.g., $Ru^{-1}$) measured at 170° C. In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of less than or equal to about 100%, less than or equal to about 99%, less than or equal to about 95%, less than or equal to about 90%, less than or equal to about 85%, less than or equal to about 80%, less than or equal to about 75%, less than or equal to about 70%, or less than or equal to about 60% and a turnover number of at least about 100,000 per moles of active metal centers (e.g., $Ru^{-1}$) measured at 170° C. Combinations of the above recited ranges are also possible. For example, in certain embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50% and less than or equal to about 100% and a turnover number of at least about 100,000 per moles of active metal centers (e.g., $Ru^{-1}$) measured at 170° C., the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 85% and less than or equal to about 99% and a turnover number of at least about 100,000 per moles of active metal centers (e.g., $Ru^{-1}$) measured at 170° C.

In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50%, at least about 60%, at least about 70%, at least about 75%, at least about 80%, at least about 85%, at least about 90%, at least about 95%, at least about 99% and a turnover number of at least about 200,000 per moles of active metal centers (e.g., $Ru^{-1}$) measured at 170° C. In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of less than or equal to about 100%, less than or equal to about 99%, less than or equal to about 95%, less than or equal to about 90%, less than or equal to about 85%, less than or equal to about 80%, less than or equal to about 75%, less than or equal to about 70%, or less than or equal to about 60% and a turnover number of at least about 200,000 per moles of active metal centers (e.g., $Ru^{-1}$) measured at 170° C. Combinations of the above recited ranges are also possible. For example, in certain embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50% and less than or equal to about 100% and a turnover number of at least about 200,000 per moles of active metal centers (e.g., $Ru^{-1}$) measured at 170° C., the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 85% and less than or equal to about 99% and a turnover number of at least about 200,000 per moles of active metal centers (e.g., $Ru^{-1}$) measured at 170° C.

In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50%, at least about 60%, at least about 70%, at least about 75%, at least about 80%, at least about 85%, at least about 90%, at least about 95%, at least about 99% and a turnover number of at least about 300,000 per moles of active metal centers (e.g., $Ru^{-1}$) measured at 170° C. In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of less than or equal to about 100%, less than or equal to about 99%, less than or equal to about 95%, less than or equal to about 90%, less than or equal to about 85%, less than or equal to about 80%, less than or equal to about 75%, less than or equal to about 70%, or less than or equal to about 60% and a turnover number of at least about 300,000 per moles of active metal centers (e.g., $Ru^{-1}$) measured at 170° C. Combinations of the above recited ranges are also possible. For example, in certain embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50% and less than or equal to about 100% and a turnover number of at least about 300,000 per moles of active metal centers (e.g., $Ru^{-1}$) measured at 170° C., the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 85% and less than or equal to about 99% and a turnover number of at least about 300,000 per moles of active metal centers (e.g., $Ru^{-1}$) measured at 170° C.

In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50%, at least about 60%, at least about 70%, at least about 75%, at least about 80%, at least about 85%, at least about 90%, at least about 95%, at least about 99% and a turnover number of at least about 400,000 per moles of active metal centers (e.g., $Ru^{-1}$) measured at 170° C. In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of less than or equal to about 100%, less than or equal to about 99%, less than or equal to about 95%, less than or equal to about 90%, less than or equal to about 85%, less than or equal to about 80%, less than or equal to about 75%, less than or equal to about 70%, or less than or equal to about 60% and a turnover number of at least about 400,000 per moles of active metal centers (e.g., $Ru^{-1}$) measured at 170° C. Combinations of the above recited ranges are also possible. For example, in certain embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50% and less than or equal to about 100% and a turnover number of at least about 400,000 per moles of active metal centers (e.g., $Ru^{-1}$) measured at 170° C., the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 85% and less than or equal to about 99% and a turnover number of at least about 400,000 per moles of active metal centers (e.g., $Ru^{-1}$) measured at 170° C.

In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50%, at least about 60%, at least about 70%, at least about 75%, at least about 80%, at least about 85%, at least about 90%, at least about 95%, at least about 99% and a turnover number of at least about 500,000 per moles of active metal centers (e.g., $Ru^{-1}$) measured at 170° C. In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of less than or equal to about 100%, less than or equal to about 99%, less than or equal to about 95%, less than or equal to about 90%, less than or equal to about 85%, less than or equal to about 80%, less than or equal to about 75%, less than or equal to about 70%, or less than or equal to about 60% and a turnover number of at least about 500,000 per moles of active metal centers (e.g., $Ru^{-1}$) measured at 170° C. Combinations of the above recited ranges are also possible. For example, in certain embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50% and less than or equal to about 100% and a turnover number of at least about 500,000 per moles of active metal centers (e.g., $Ru^{-1}$) measured at 170° C., the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 85% and less than or equal to about 99% and a turnover number of at least about 500,000 per moles of active metal centers (e.g., $Ru^{-1}$) measured at 170° C.

In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50%, at least about 60%, at least about 70%, at least about 75%, at least about 80%, at least about 85%, at least about 90%, at least about 95%, at least about 99% and a turnover number of at least about 600,000 per moles of active metal centers (e.g., $Ru^{-1}$) measured at 170° C. In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of less than or equal to about 100%, less than or equal to about 99%, less than or equal to about 95%, less than or equal to about 90%, less than or equal to about 85%, less than or equal to about 80%, less than or equal to about 75%, less than or equal to about 70%, or less than or equal to about 60% and a turnover number of at least about 600,000 per moles of active metal centers (e.g., $Ru^{-1}$) measured at 170° C. Combinations of the above recited ranges are also possible. For example, in certain embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50% and less than or equal to about 100% and a turnover number of at least about 600,000 per moles of active metal centers (e.g., $Ru^{-1}$) measured at 170° C., the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 85% and less than or equal to about 99% and a turnover number of at least about 600,000 per moles of active metal centers (e.g., $Ru^{-1}$) measured at 170° C.

In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50%, at least about 60%, at least about 70%, at least about 75%, at least about 80%, at least about 85%, at least about 90%, at least about 95%, at least about 99% and a turnover number of at least about 700,000 per moles of active metal centers (e.g., $Ru^{-1}$) measured at 170° C. In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of less than or equal to about 100%, less than or equal to about 99%, less than or equal to about 95%, less than or equal to about 90%, less than or equal to about 85%, less than or equal to about 80%, less than or equal to about 75%, less than or equal to about 70%, or less than or equal to about 60% and a turnover number of at least about 700,000 per moles of active metal centers (e.g., $Ru^{-1}$) measured at 170° C. Combinations of the above recited ranges are also possible. For example, in certain embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50% and less than or equal to about 100% and a turnover number of at least about 700,000 per moles of active metal centers (e.g., $Ru^{-1}$) measured at 170° C., the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 85% and less than or equal to about 99% and a turnover number of at least about 700,000 per moles of active metal centers (e.g., $Ru^{-1}$) measured at 170° C.

In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50%, at least about 60%, at least about 70%, at least about 75%, at least about 80%, at least about 85%, at least about 90%, at least about 95%, at least about 99% and a turnover number of at least about 800,000 per moles of active metal centers (e.g., $Ru^{-1}$) measured at 170° C. In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of less than or equal to about 100%, less than or equal to about 99%, less than or equal to about 95%, less than or equal to about 90%, less than or equal to about 85%, less than or equal to about 80%, less than or equal to about 75%, less than or equal to about 70%, or less than or equal to about 60% and a turnover number of at least about 800,000 per moles of active metal centers (e.g., $Ru^{-1}$) measured at 170° C. Combinations of the above recited ranges are also possible. For example, in certain embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50% and less than or equal to about 100% and a turnover number of at least about 800,000 per moles of active metal centers (e.g., $Ru^{-1}$) measured at 170° C., the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 85% and less than or equal to about 99% and a turnover number of at least about 800,000 per moles of active metal centers (e.g., $Ru^{-1}$) measured at 170° C.

In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50%, at least about 60%, at least about 70%, at least about 75%, at least about 80%, at least about 85%, at least about 90%, at least about 95%, at least about 99% and a turnover frequency of at least about 100 per moles of active metal centers per hour (e.g., $Ru^{-1}h^{-1}$) measured at 170° C. In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of less than or equal to about 100%, less than or equal to about 99%, less than or equal to about 95%, less than or equal to about 90%, less than or equal to about 85%, less than or equal to about 80%, less than or equal to about 75%, less than or equal to about 70%, or less than or equal to about 60% and a turnover frequency of at least about 100 per moles of active metal centers per hour (e.g., $Ru^{-1}h^{-1}$) measured at 170° C. Combinations of the above recited ranges are also possible. For example, in certain embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50% and less than or equal to about 100% and a turnover frequency of at least about 100 per moles of active metal centers per hour (e.g., $Ru^{-1}h^{-1}$) measured at 170° C., the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 85% and less than or equal to about 99% and a turnover frequency of at least about 100 per moles of active metal centers per hour (e.g., $Ru^{-1}h^{-1}$) measured at 170° C.

In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50%, at least about 60%, at least about 70%, at least about 75%, at least about 80%, at least about 85%, at least about 90%, at least about 95%, at least about 99% and a turnover frequency of at least about 500 per moles of active metal centers per hour (e.g., $Ru^{-1}h^{-1}$) measured at 170° C. In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of less than or equal to about 100%, less than or equal to about 99%, less than or equal to about 95%, less than or equal to about 90%, less than or equal to about 85%, less than or equal to about 80%, less than or equal to about 75%, less than or equal to about 70%, or less than or equal to about 60% and a turnover frequency of at least about 500 per moles of active metal centers per hour (e.g., $Ru^{-1}h^{-1}$) measured at 170° C. Combinations of the above recited ranges are also possible. For example, in certain embodiments, the catalytic MOF composition and/or the plurality of nanoparticles associated with the MOF composition catalyzes catalyze the conversion of one or more first alcohols (e.g., ethanol) to one or more second alcohols (e.g., 1-butanol) with a selectivity of at least about 50% and less than or equal to about 100% and a turnover frequency of at least about 500 per moles of active metal centers per hour (e.g., $Ru^{-1}h^{-1}$) measured at 170° C., the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 85% and less than or equal to about 99% and a turnover frequency of at least about 500 per moles of active metal centers per hour (e.g., $Ru^{-1}h^{-1}$) measured at 170° C.

In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50%, at least about 60%, at least about 70%, at least about 75%, at least about 80%, at least about 85%, at least about 90%, at least about 95%, at least about 99% and a turnover frequency of at least about 1,000 per moles of active metal centers per hour (e.g., $Ru^{-1}h^{-1}$) measured at 170° C. In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of less than or equal to about 100%, less than or equal to about 99%, less than or equal to about 95%, less than or equal to about 90%, less than or equal to about 85%, less than or equal to about 80%, less than or equal to about 75%, less than or equal to about 70%, or less than or equal to about 60% and a turnover frequency of at least about 1,000 per moles of active metal centers per hour (e.g., $Ru^{-1}h^{-1}$) measured at 170° C. Combinations of the above recited ranges are also possible. For example, in certain embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50% and less than or equal to about 100% and a turnover frequency of at least about 1,000 per moles of active metal centers per hour (e.g., $Ru^{-1}h^{-1}$) measured at 170° C., the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 85% and less than or equal to about 99% and a turnover frequency of at least about 1,000 per moles of active metal centers per hour (e.g., $Ru^{-1}h^{-1}$) measured at 170° C.

In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50%, at least about 60%, at least about 70%, at least about 75%, at least about 80%, at least about 85%, at least about 90%, at least about 95%, at least about 99% and a turnover frequency of at least about 2,000 per moles of active metal centers per hour (e.g., $Ru^{-1}h^{-1}$) measured at 170° C. In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of less than or equal to about 100%, less than or equal to about 99%, less than or equal to about 95%, less than or equal to about 90%, less than or equal to about 85%, less than or equal to about 80%, less than or equal to about 75%, less than or equal to about 70%, or less than or equal to about 60% and a turnover frequency of at least about 2,000 per moles of active metal centers per hour (e.g., $Ru^{-1}h^{-1}$) measured at 170° C. Combinations of the above recited ranges are also possible. For example, in certain embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50% and less than or equal to about 100% and a turnover frequency of at least about 2,000 per moles of active metal centers per hour (e.g., $Ru^{-1}h^{-1}$) measured at 170° C., the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 85% and less than or equal to about 99% and a turnover frequency of at least about 2,000 per moles of active metal centers per hour (e.g., $Ru^{-1}h^{-1}$) measured at 170° C.

In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50%, at least about 60%, at least about 70%, at least about 75%, at least about 80%, at least about 85%, at least about 90%, at least about 95%, at least about 99% and a turnover frequency of at least about 3,000 per moles of active metal centers per hour (e.g., $Ru^{-1}h^{-1}$) measured at 170° C. In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of less than or equal to about 100%, less than or equal to about 99%, less than or equal to about 95%, less than or equal to about 90%, less than or equal to about 85%, less than or equal to about 80%, less than or equal to about 75%, less than or equal to about 70%, or less than or equal to about 60% and a turnover frequency of at least about 3,000 per moles of active metal centers per hour (e.g., $Ru^{-1}h^{-1}$) measured at 170° C. Combinations of the above recited ranges are also possible. For example, in certain embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50% and less than or equal to about 100% and a turnover frequency of at least about 3,000 per moles of active metal centers per hour (e.g., $Ru^{-1}h^{-1}$) measured at 170° C., the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 85% and less than or equal to about 99% and a turnover frequency of at least about 3,000 per moles of active metal centers per hour (e.g., $Ru^{-1}h^{-1}$) measured at 170° C.

In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50%, at least about 60%, at least about 70%, at least about 75%, at least about 80%, at least about 85%, at least about 90%, at least about 95%, at least about 99% and a turnover frequency of at least about 4,000 per moles of active metal centers per hour (e.g., $Ru^{-1}h^{-1}$) measured at 170° C. In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of less than or equal to about 100%, less than or equal to about 99%, less than or equal to about 95%, less than or equal to about 90%, less than or equal to about 85%, less than or equal to about 80%, less than or equal to about 75%, less than or equal to about 70%, or less than or equal to about 60% and a turnover frequency of at least about 4,000 per moles of active metal centers per hour (e.g., $Ru^{-1}h^{-1}$) measured at 170° C. Combinations of the above recited ranges are also possible. For example, in certain embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50% and less than or equal to about 100% and a turnover frequency of at least about 4,000 per moles of active metal centers per hour (e.g., $Ru^{-1}h^{-1}$) measured at 170° C., the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 85% and less than or equal to about 99% and a turnover frequency of at least about 4,000 per moles of active metal centers per hour (e.g., $Ru^{-1}h^{-1}$) measured at 170° C.

In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50%, at least about 60%, at least about 70%, at least about 75%, at least about 80%, at least about 85%, at least about 90%, at least about 95%, at least about 99% and a turnover frequency of at least about 5,000 per moles of active metal centers per hour (e.g., $Ru^{-1}h^{-1}$) measured at 170° C. In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of less than or equal to about 100%, less than or equal to about 99%, less than or equal to about 95%, less than or equal to about 90%, less than or equal to about 85%, less than or equal to about 80%, less than or equal to about 75%, less than or equal to about 70%, or less than or equal to about 60% and a turnover frequency of at least about 5,000 per moles of active metal centers per hour (e.g., $Ru^{-1}h^{-1}$) measured at 170° C. Combinations of the above recited ranges are also possible. For example, in certain embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50% and less than or equal to about 100% and a turnover frequency of at least about 5,000 per moles of active metal centers per hour (e.g., $Ru^{-1}h^{-1}$) measured at 170° C., the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 85% and less than or equal to about 99% and a turnover frequency of at least about 5,000 per moles of active metal centers per hour (e.g., $Ru^{-1}h^{-1}$) measured at 170° C.

In some embodiments, the catalytic MOF composition and/or the plurality of nanoparticles associated with the MOF composition may catalyze the conversion of one or more first alcohols (e.g., ethanol) to one or more second alcohols (e.g., 1-butanol) with a selectivity of at least about 50%, at least about 60%, at least about 70%, at least about 75%, at least about 80%, at least about 85%, at least about 90%, at least about 95%, at least about 99% and a turnover frequency of at least about 10,000 per moles of active metal centers per hour (e.g., $Ru^{-1}h^{-1}$) measured at 170° C. In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of less than or equal to about 10,000%, less than or equal to about 99%, less than or equal to about 95%, less than or equal to about 90%, less than or equal to about 85%, less than or equal to about 80%, less than or equal to about 75%, less than or equal to about 70%, or less than or equal to about 60% and a turnover frequency of at least about 5,000 per moles of active metal centers per hour (e.g., $Ru^{-1}h^{-1}$) measured at 170° C. Combinations of the above recited ranges are also possible. For example, in certain embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50% and less than or equal to about 100% and a turnover frequency of at least about 10,000 per moles of active metal centers per hour (e.g., $Ru^{-1}h^{-1}$) measured at 170° C., the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 85% and less than or equal to about 99% and a turnover frequency of at least about 10,000 per moles of active metal centers per hour (e.g., $Ru^{-1}h^{-1}$) measured at 170° C.

In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50%, at least about 60%, at least about 70%, at least about 75%, at least about 80%, at least about 85%, at least about 90%, at least about 95%, at least about 99% and a turnover frequency of at least about 11,000 per moles of active metal centers per hour (e.g., $Ru^{-1}h^{-1}$) measured at 170° C. In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of less than or equal to about 100%, less than or equal to about 99%, less than or equal to about 95%, less than or equal to about 90%, less than or equal to about 85%, less than or equal to about 80%, less than or equal to about 75%, less than or equal to about 70%, or less than or equal to about 60% and a turnover frequency of at least about 11,000 per moles of active metal centers per hour (e.g., $Ru^{-1}h^{-1}$) measured at 170° C. Combinations of the above recited ranges are also possible. For example, in certain embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50% and less than or equal to about 100% and a turnover frequency of at least about 11,000 per moles of active metal centers per hour (e.g., $Ru^{-1}h^{-1}$) measured at 170° C., the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 85% and less than or equal to about 99% and a turnover frequency of at least about 11,000 per moles of active metal centers per hour (e.g., $Ru^{-1}h^{-1}$) measured at 170° C.

In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50%, at least about 60%, at least about 70%, at least about 75%, at least about 80%, at least about 85%, at least about 90%, at least about 95%, at least about 99% and a turnover frequency of at least about 12,000 per moles of active metal centers per hour (e.g., $Ru^{-1}h^{-1}$) measured at 170° C. In some embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of less than or equal to about 100%, less than or equal to about 99%, less than or equal to about 95%, less than or equal to about 90%, less than or equal to about 85%, less than or equal to about 80%, less than or equal to about 75%, less than or equal to about 70%, or less than or equal to about 60% and a turnover frequency of at least about 12,000 per moles of active metal centers per hour (e.g., $Ru^{-1}h^{-1}$) measured at 170° C. Combinations of the above recited ranges are also possible. For example, in certain embodiments, the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 50% and less than or equal to about 100% and a turnover frequency of at least about 12,000 per moles of active metal centers per hour (e.g., $Ru^{-1}h^{-1}$) measured at 170° C., the catalytic MOF composition and/or the plurality of nanoparticles associated with the MOF composition catalyzes the conversion of one or more first alcohols (e.g., ethanol) to one or more second alcohols (e.g., 1-butanol) with a selectivity of at least about 85% and less than or equal to about 99% and a turnover frequency of at least about 12,000 per moles of active metal centers per hour (e.g., $Ru^{-1}h^{-1}$) measured at 170° C.

Those of ordinary skill in the art will be aware of suitable systems and methods for utilizing a MOF composition described herein for catalysis. In some embodiments, the reaction is carried out in a suitable apparatus capable of withstanding high pressures. In some embodiments, the precursor MOF composition and reactants described herein are loaded into a reactor in any sequential order, and the precursor MOF composition is activated by the methods described herein. For example, the precursor MOF composition may be loaded into a reactor for use as a catalyst for converting ethanol to 1-butanol and subsequently activated. In certain embodiments, the conversion of ethanol to 1-butanol using a catalytic MOF composition is conducted in a stainless steel reactor. According to certain embodiments, the conversion of ethanol to 1-butanol using a catalytic MOF composition is conducted in a steel Paar reactor with a glass insert. The reaction may be carried out in the presence of one or more additives. For example, in some embodiments, the reaction is carried out in the presence of a base (e.g., sodium ethoxide). In certain embodiments, an acetate (e.g., sodium acetate) is formed by a side reaction of the base (e.g., sodium ethoxide). In certain embodiments, an additive is added to convert the acetate back to the base. In some embodiments, the additive is a co-catalyst (e.g., $Ru^0$ powder, Ru/C, $Ru^0$ supported on carbon nanotubes, $Cu^0$, or other reduction catalysts).

In some embodiments, the reaction is carried out in a sealed reaction vessel. Use of a sealed reaction vessel can allow for reaction intermediates (e.g., $H_2$) to be contained and used in later reaction steps. For example, a precursor MOF composition, one or more additives (e.g., a base), and reactants (e.g., ethanol) described herein may be loaded into a reactor in any sequential order. For example, according to certain embodiments and as shown in FIG. 1, $H_2$ is formed in step 102 from the dehydrogenation of ethanol and is subsequently stored inside the sealed reaction vessel (e.g., in the plurality of pores of the MOF compound), and consumed in step 108 during the hydrogenation to form 1-butanol.

In some embodiments, a catalytic MOF composition described herein for use in catalysis is formed in situ via activation of a precursor MOF composition. For example, the catalytic MOF composition may be formed by loading the precursor MOF composition, one or additives (e.g., a base), and reactants (e.g., ethanol) into a reaction vessel, and increasing the temperature to an elevated temperature. In some embodiments, the elevated temperature is greater than or equal to about 100° C., greater than or equal to about 110°

C., greater than or equal to about 120° C., greater than or equal to about 130° C., greater than or equal to about 140° C., greater than or equal to about 150° C., greater than or equal to about 160° C., greater than or equal to about 170° C., greater than or equal to about 180° C., or greater than or equal to about 190° C. In certain embodiments, the elevated temperature is less than or equal to about 200° C., less than or equal to about 190° C., less than or equal to about 180° C., less than or equal to about 170° C., less than or equal to about 160° C., less than or equal to about 150° C., less than or equal to about 140° C., less than or equal to about 130° C., less than or equal to about 120° C., or less than or equal to about 110° C. Combinations of the above recited ranges are also possible. For example, in some embodiments, the elevated temperature is between greater than or equal to 100° C. and less than or equal to 200° C., or the elevated temperature is between greater than 140° C. and less than or equal to 180° C. In certain embodiments, the elevated temperature is 150° C. In some embodiments, the elevated temperature is 170° C.

A catalytic MOF composition may be provided in any suitable amount for the conversion of ethanol to 1-butanol. In some embodiments, the ratio of the moles of substrate (e.g., ethanol) to the moles of active metal centers (e.g., ruthenium) in the catalytic MOF composition is greater than or equal to about 10:1, greater than or equal to about 20:1, greater than or equal to about 50:1, greater than or equal to about 100:1, greater than or equal to about 200:1, greater than or equal to about 300:1, greater than or equal to about 400:1, greater than or equal to about 500:1, greater than or equal to about 1,000:1, greater than or equal to about 10,000:1, greater than or equal to about 100,000:1, greater than or equal to about 500,000:1. In certain embodiments, the ratio of the moles of substrate (e.g., ethanol to the moles of active metal centers (e.g., ruthenium) in the catalytic MOF composition is less than or equal to about 1,000,000:1, less than or equal to about 500,000:1, less than or equal to about 100,000:1, less than or equal to about 10,000:1, less than or equal to about 1,000:1. less than or equal to about 500:1, less than or equal to about 400:1, less than or equal to about 300:1, less than or equal to about 200:1, less than or equal to about 100:1, less than or equal to about 50:1, or less than or equal to about 20:1. Combinations of the above recited ranges are also possible. For example, in some embodiments, the ratio of the moles of substrate (e.g., ethanol) to the moles of active metal centers (e.g., ruthenium) in the catalytic MOF composition is between about 10:1 and about 1,000,000:1, or between about 10:1 and about 500,000:1, or between about 10:1 and 100,000:1, or between about 10:1 and 10,000:1, or between about 10:1 and 1,000:1, or between about 10:1 and about 500:1, or between about 10:1 and about 400:1, or between about 10:1 and about 300:1, or between about 20:1 and about 300:1, or between about 20:1 and 200:1, or greater than about 10:1, or greater than about 20:1, or greater than about 50:1, or greater than about 100:1, or greater than about 200:1, or greater than about 300:1, or greater than about 400:1, or greater than about 500:1, or greater than about 1,000:1, or greater than about 10,000:1, or greater than about 100,000:1, or greater than about 500,000:1.

The conversion of the one or more first alcohols (e.g., ethanol) to one or more second alcohols (e.g., 1-butanol) may be conducted at any suitable reaction temperatures. For example, in some embodiments, the conversion of one or more first alcohols to one or more second alcohols in the presence of the catalytic MOF composition is conducted at a temperature of at least about 75° C., at least about 100° C., at least about 125° C., at least about 150° C., at least about 170° C., at least about 175° C., or at least about 200° C. In certain embodiments, the conversion of the one or more first alcohols (e.g., ethanol) to one or more second alcohols (e.g., 1-butanol) in the presence of the catalytic MOF composition is conducted at a temperature of less than or equal to about 225° C., less than or equal to about 200° C., less than or equal to about 175° C., less than or equal to about 170° C., less than or equal to about 150° C., or less than or equal to about 125° C. Combinations of the above-referenced ranges are also possible (e.g., between about 100° C. and about 200° C.). Other ranges are also possible.

In some embodiments, the conversion of the one or more first alcohols (e.g., ethanol to one or more second alcohols (e.g., 1-butanol) in the presence of a catalytic MOF composition may be conducted at any suitable pressure. According to certain embodiments, the conversion of the one or more first alcohols to one or more second alcohols in the presence of a catalytic MOF composition is conducted at standard conditions for pressure (e.g., about 1 bar). In certain cases, the conversion of the one or more first alcohols to one or more second alcohols in the presence of the catalytic MOF composition is conducted at about 1 bar, however the pressure inside the reactor may increase (e.g., at least in part due to the generation of $H_2$ and/or gaseous alcohol). In some embodiments, for example, the conversion of the one or more first alcohols to one or more second alcohols in the presence of a catalytic MOF composition is conducted at a pressure of at least about 15 bar, at least about 30 bar, or at least about 50 bar. In certain embodiments, the conversion of ethanol to 1-butanol in the presence of a catalytic MOF composition is conducted at a pressure of less than or equal to about 75 bar, less than or equal to about 50 bar, or less than or equal to about 30 bar. Combinations of the above-referenced ranges are also possible (e.g., between about 15 bar and about 75 bar). Other ranges are also possible.

According to certain embodiments, the conversion of the one or more first alcohols (e.g., ethanol) to one or more second alcohols (e.g., 1-butanol) in the presence of a catalytic MOF composition is conducted for any suitable duration of time. For example, the conversion of the one or more first alcohols to one or more second alcohols in the presence of a catalytic MOF composition is conducted for at least about 5 hours, at least about 10 hours, at least about 15 hours, at least about 20 hours, at least about 25 hours, at least about 50 hours, at least about 75 hours, at least about 100 hours, or at least about 150 hours. In certain embodiments, the conversion of the one or more first alcohols to one or more second alcohols is conducted for less than about 200 hours, less than about 150 hours, less than about 100 hours, less than about 50 hours, less than about 5 hours, less than about 20 hours, less than about 15 hours, or less than about 10 hours. Combinations of these ranges are also possible (e.g., at least about 10 hours and less than about 25 hours). Other ranges are also possible.

Those skilled in the art would be capable of selecting suitable combinations of temperatures, pressures, and duration of time for the conversion of ethanol to 1-butanol based upon the teachings of the specification.

For convenience, certain terms employed in the specification, examples, and appended claims are listed here.

As used herein, the term "reacting" refers to the forming of a bond between two or more components to produce a stable, isolable compound. For example, a first component and a second component may react to form one reaction product comprising the first component and the second component joined by a covalent bond. That is, the term "reacting" does not refer to the interaction of solvents, catalysts, bases, ligands, or other materials which may serve to promote the occurrence of the reaction with the component(s).

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito: 1999, the entire contents of which are incorporated herein by reference.

As used herein, the term "alcohol" is given its ordinary meaning in the art and generally refers to an organic compound with at least one hydroxyl functional group (—OH) (e.g., bound to a carbon atom of an alkyl group (e.g., a hydrocarbon chain)). Non-limiting examples of alcohols include methanol, ethanol, (iso)propanol, and butanol. Alcohols may be saturated or unsaturated (at one or more locations) and may have a linear, branched, monocyclic, or polycyclic structure. Alcohols may be aliphatic or aromatic, and may contain one or more alkyl, alkene, and/or alkyne functional groups. In certain but not necessarily all embodiments, alcohols may comprise more than one —OH functional group. In some embodiments, the alcohol is a $C_1$-$C_{10}$ alcohol, such as a $C_1$-$C_8$ alcohol, a $C_1$-$C_6$ alcohol, or a $C_1$-$C_4$ alcohol.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

As used herein, the term "alkyl" is given its ordinary meaning in the art and refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some cases, the alkyl group may be a lower alkyl group, i.e., an alkyl group having 1 to 10 carbon atoms (e.g., methyl, ethyl, propyl, butyl, pentyl, hexyl, heptyl, octyl, nonyl, or decyl). In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., C1-C12 for straight chain, C3-C12 for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, t-butyl, cyclobutyl, hexyl, and cyclochexyl.

The term "alkylene" as used herein refers to a bivalent alkyl group. An "alkylene" group is a polymethylene group, i.e., —$(CH_2)z$-, wherein z is a positive integer, e.g., from 1 to 20, from 1 to 10, from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described herein for a substituted aliphatic group.

Generally, the suffix "-ene" is used to describe a bivalent group. Thus, any of the terms defined herein can be modified with the suffix "-ene" to describe a bivalent version of that moiety. For example, a bivalent carbocycle is "carbocyclylene", a bivalent aryl ring is "arylene", a bivalent benzene ring is "phenylene", a bivalent heterocycle is "heterocyclylene", a bivalent heteroaryl ring is "heteroarylene", a bivalent alkyl chain is "alkylene", a bivalent alkenyl chain is "alkenylene", a bivalent alkynyl chain is "alkynylene", a bivalent heteroalkyl chain is "heteroalkylene", a bivalent heteroalkenyl chain is "heteroalkenylene", a bivalent heteroalkynyl chain is "heteroalkynylene", and so forth.

The terms "alkenyl" and "alkynyl" are given their ordinary meaning in the art and refer to unsaturated aliphatic groups analogous in length and possible substitution to the alkyls described above, but that contain at least one double or triple bond respectively.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, t-butyl, n-pentyl, sec-pentyl, isopentyl, t-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "cycloalkyl," as used herein, refers specifically to groups having three to ten, preferably three to seven carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic, or hetercyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the examples that are described herein.

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl", "heteroalkynyl", and the like. Furthermore, as used herein, the terms "heteroalkyl", "heteroalkenyl", "heteroalkynyl", and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkyl" is given its ordinary meaning in the art and refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, alkoxyalkyl, amino, thioester, poly(ethylene glycol), and alkyl-substituted amino.

The terms "heteroalkenyl" and "heteroalkynyl" are given their ordinary meaning in the art and refer to unsaturated aliphatic groups analogous in length and possible substitution to the heteroalkyls described above, but that contain at least one double or triple bond respectively.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CHF$_2$; —CH$_2$F; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alycyclic, heteroaliphatic, heterocyclic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the examples that are described herein.

The term "aryl" is given its ordinary meaning in the art and refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. Substituents include, but are not limited to, any of the previously mentioned substituents, i.e., the substituents recited for aliphatic moieties, or for other moieties as disclosed herein, resulting in the formation of a stable compound. In some cases, an aryl group is a stable mono- or polycyclic unsaturated moiety having preferably 3-14 carbon atoms, each of which may be substituted or unsubstituted. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups.

The terms "heteroaryl" is given its ordinary meaning in the art and refers to aryl groups comprising at least one heteroatom as a ring atom. A "heteroaryl" is a stable heterocyclic or polyheterocyclic unsaturated moiety having preferably 3-14 carbon atoms, each of which may be substituted or unsubstituted. Substituents include, but are not limited to, any of the previously mentioned substituents, i.e., the substitutes recited for aliphatic moieties, or for other moieties as disclosed herein, resulting in the formation of a stable compound. In some cases, a heteroaryl is a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will also be appreciated that aryl and heteroaryl moieties, as defined herein may be attached via an alkyl or heteroalkyl moiety and thus also include -(alkyl)aryl, -(heteroalkyl)aryl, -(heteroalkyl)heteroaryl, and -(heteroalkyl)heteroaryl moieties. Thus, as used herein, the phrases "aryl or heteroaryl moieties" and "aryl, heteroaryl, -(alkyl)aryl, -(heteroalkyl)aryl, -(heteroalkyl)heteroaryl, and -(heteroalkyl)heteroaryl" are interchangeable. Substituents include, but are not limited to, any of the previously mentioned substituents (e.g., the substituents recited for aliphatic moieties, or for other moieties as disclosed herein, resulting in the formation of a stable compound).

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2F$; —$CHF_2$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)R_x$; —$S(O)_2R_x$; —$NR_x(CO)R_x$ wherein each occurrence of $R_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments described herein.

It will be appreciated that the above groups and/or compounds, as described herein, may be optionally substituted with any number of substituents or functional moieties. That is, any of the above groups may be optionally substituted. As used herein, the term "substituted" is contemplated to include all permissible substituents of organic compounds, "permissible" being in the context of the chemical rules of valence known to those of ordinary skill in the art. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. The term "stable," as used herein, preferably refers to compounds which possess stability sufficient to allow manufacture and which maintain the integrity of the compound for a sufficient period of time to be detected and preferably for a sufficient period of time to be useful for the purposes detailed herein.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, carboxamido, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, cyano, alkoxyalkyl, perhaloalkyl, arylalkyloxyalkyl, and the like.

The following examples are intended to illustrate certain embodiments of the present invention, but do not exemplify the full scope of the invention.

Example 1

This example describes the conversion of ethanol to 1-butanol using a catalytic MOF composition.

Figure 4:
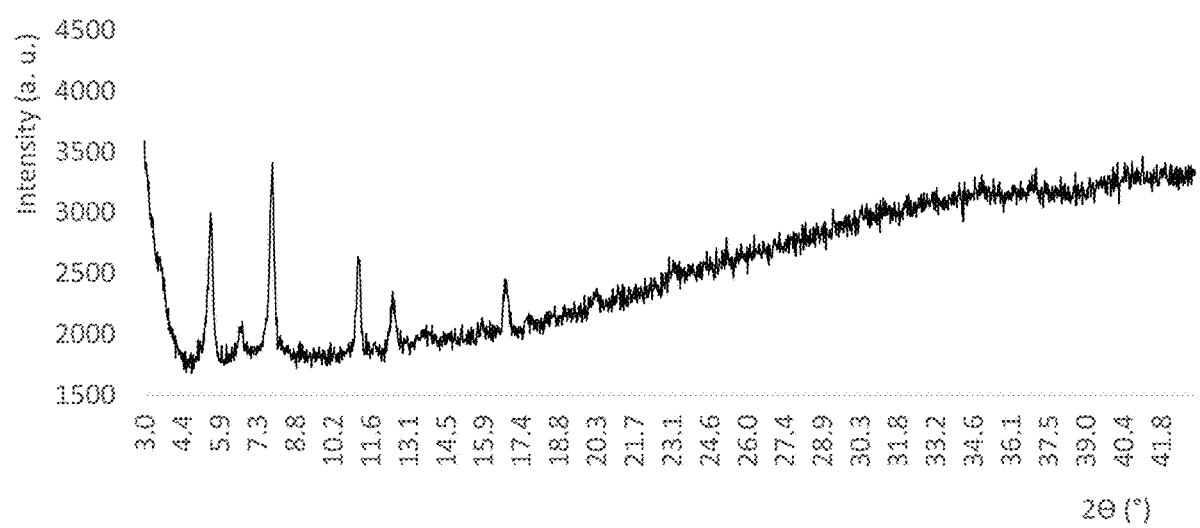
FIG. 4 shows, according to certain embodiments, a powder X-ray diffraction pattern of an exemplary precursor MOF composition.

A precursor MOF composition (Ru@MFU-1) was synthesized by addition of 1.7% $RuCl_2$(nbd) (where nbd is norbonadiene) to 25 mg of the MOF compound MFU-1 comprising cobalt ions and 1,4-bis[(3,5-dimethyl)-pyrazol-4-yl]benzene ligands. The addition of the precursor metal catalytic compound was added to the MOF compound in acetonitrile at room temperature for three days, as shown in FIG. 2. The coordination environment of cobalt in the MOF compound is shown in FIG. 3. Crystallinity of the MOF compound was preserved during the incorporation of the precursor metal catalytic compound, as established by powder X-ray diffraction, as shown in FIG. 4. Incorporation of ruthenium into the MOF compound was conducted under reaction conditions that might be expected to lead to the exchange of cobalt in the MOF compound for ruthenium. Cation exchange was excluded, however, as evidenced by X-ray photoelectron spectroscopy and X-ray absorption spectroscopy shown in FIG. 5A-6B revealed that the incorporated ruthenium species is $Ru^{2+}$ and that the primary coordination environment of ruthenium is indistinguishable by X-ray absorption spectroscopy from that of RuCl$_2$(nbd). A cobalt to ruthenium ratio of 1:0.017 was observed for the MOF composition.

To the precursor MOF composition comprising the precursor metal catalytic compound, 20 mL of sodium ethoxide (NaOEt), and ethanol (EtOH, 21% solution from Alfa Aesar) were loaded into the glass insert of a steel Paar reactor and a stir bar was added. To activate the precursor MOF composition to the catalytic MOF composition, the reactor (regulated for <200 bar pressure and fitted with a pressure gauge regulated for <70 bar) was closed and heated to 150° C. for 20 hours. After cooling the reactor to room temperature, the pressure was released and the reactor opened. Meta-xylene (20 microliters) was added as an internal standard for analysis using a microliter syringe. The reaction mixture was filtered to remove the MOF composition as well as sodium acetate, which was obtained as a by-product. Analysis of the recovered MOF composition by X-ray photoelectron spectroscopy revealed diffraction peaks indicative of metallic ruthenium, as shown in FIG. 7A-7C wherein FIG. 7A is X-ray photoelectron spectroscopy data for the precursor MOF composition Ru@MFU-1, FIG. 7B is X-ray photoelectron spectroscopy data for [RuCl$_2$(nbd)], and FIG. 7C is X-ray photoelectron spectroscopy data for the recovered catalytic MOF composition.

The filtrate was analyzed by GC-MS and the yield of products were determined by reference to calibration curves generated using an internal standard and authentic standards of the reaction products. 1-butanol was formed in an amount of 506 microliters, corresponding to 6073 turnovers per ruthenium center and a turnover frequency of 303 h$^{-1}$ per ruthenium center. 1-butanol was obtained in greater than 92% selectivity, with 2-ethyl-1-butanol (4% compared to 1-butanol) and 1-hexanol (2% compared to 1-butanol) obtained as minor side products.

Figure 8:
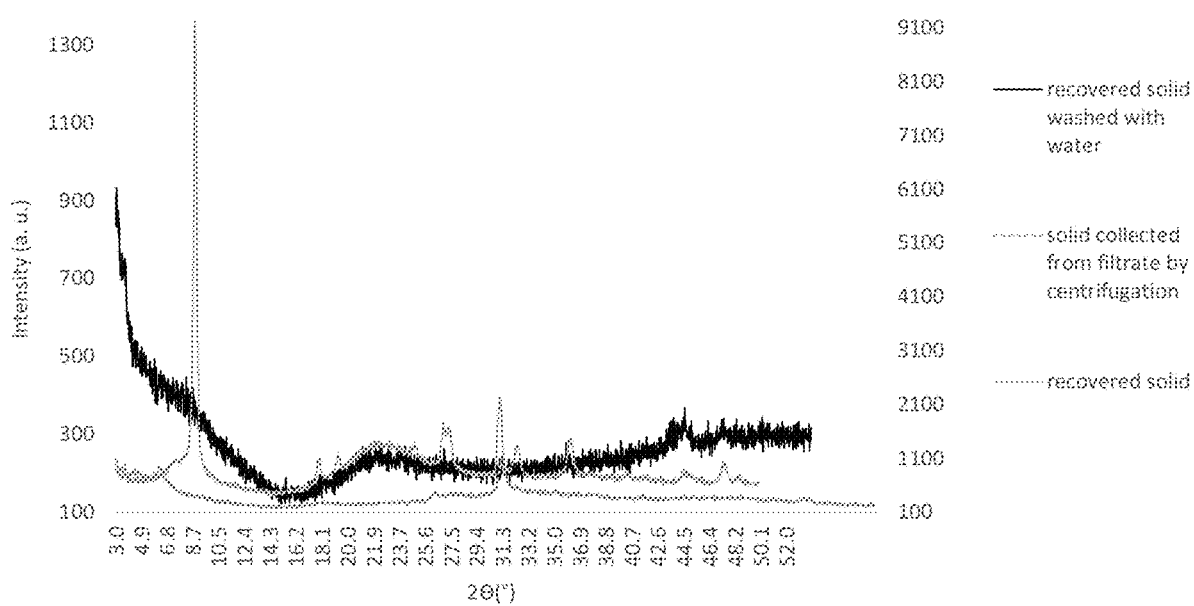
FIG. 8 shows, according to certain embodiments, a powder X-ray diffraction (PXRD) pattern of an exemplary recovered catalytic MOF composition.

A powder X-ray diffraction pattern of the solid removed from the reaction mixture by filtration was obtained (FIG. 8). The recovered solid (see light gray trace, FIG. 8) was washed with water, dissolving sodium acetate. The remaining black solid (see black trace, FIG. 8) reveals the presence of Ru$^0$ nanoparticles. The MOF compound loses its crystallinity over the course of the reaction and can thus not be detected by powder X-ray diffraction. The filtrate of the reaction mixture was subjected to centrifugation (20 minutes at 3000 rpm), and the recovered solid was analyzed by powder X-ray diffraction to check for a Ru$^0$ signature, which would indicate leaching of Ru$^0$ from the MOF composition comprising ruthenium during the reaction (see light gray dotted trace, FIG. 8).

Figure 9:
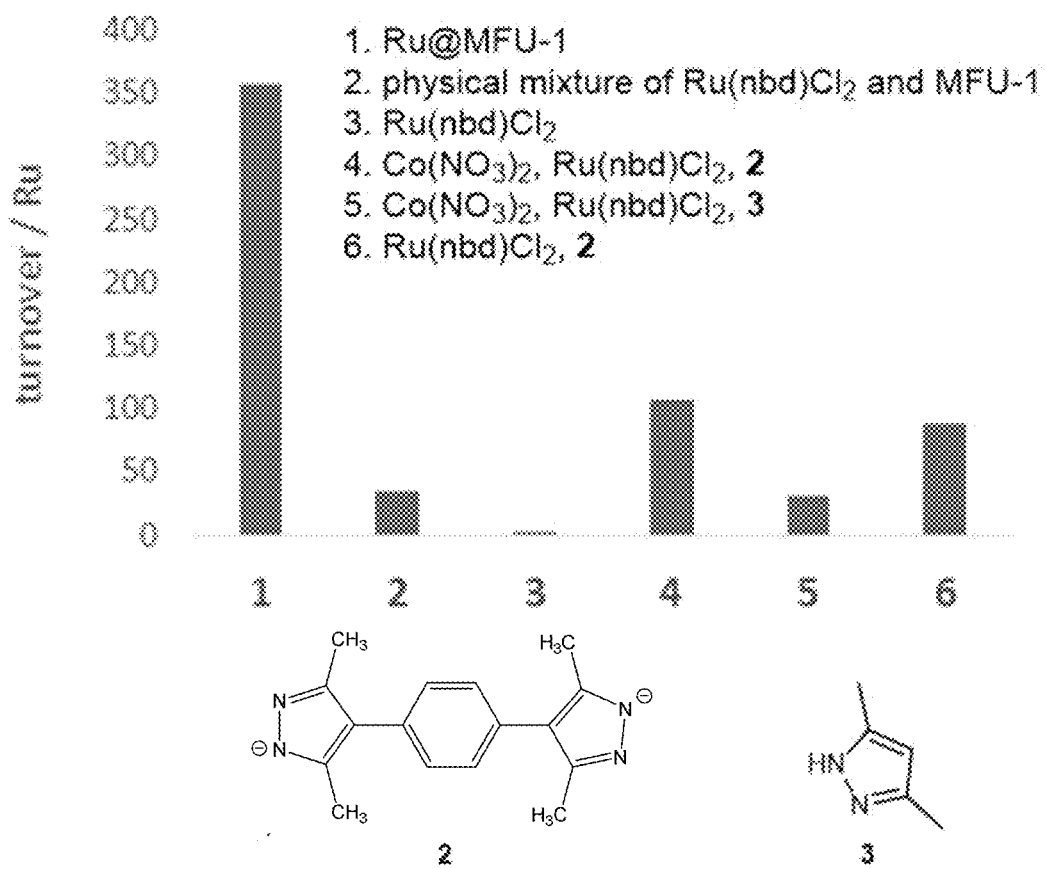
FIG. 9 shows, according to certain embodiments, the catalytic activity of an exemplary MOF composition compared to various starting materials.

Catalytic experiments were performed to compare the turnover number (TON) for ethanol to butanol upgrading per ruthenium center for the MOF composition with different combinations of the reaction components used to prepare the MOF composition (FIG. 9). The MOF composition was found to be a far more active catalyst than a mixture of Ru(nbd)Cl$_2$ and the MOF compound without Ru(nbd)Cl$_2$ incorporated. Interestingly, the physical mixture of the MOF compound and Ru(nbd)Cl$_2$ led to higher TON than Ru(nbd)Cl$_2$ itself, while a mixture of the metal salt and ligand precursors of the MOF compound, along with Ru(nbd)Cl$_2$, led to the highest TON after the MOF composition, suggesting, in some cases, that some degree of self-assembly of the MOF composition active catalyst may occur under the reaction conditions. As shown in FIG. 9, comparison of entries (4) and (5) shows that the beneficial effect of the ligand 1,4-bis[(3,5-dimethyl)-pyrazol-4-yl]benzene was not simply due to the presence of a nitrogenous ligand. Addition of dimethylpyrazole improved the ethanol upgrading activity of Ru(nbd)Cl$_2$, but despite the higher solubility of the simplified ligand system, addition of dimethylpyrazole showed a less pronounced beneficial effect than 1,4-bis[(3,5-dimethyl)-pyrazol-4-yl]benzene.

Optimization of the reaction conditions for ethanol upgrading revealed that sodium ethoxide was the optimal base for the transformation, and an increase in the reaction temperature from 120° C. to 150° C. significantly increased the TOF. The MOF compound in the MOF composition loses crystallinity under the reaction conditions, but the loss in crystallinity is not accompanied by any decrease in the activity of the MOF composition.

Example 2

Different MOF compounds were evaluated to probe the influence of the MOF compound on the activity and selectivity of the MOF composition for ethanol upgrading. Addition of Ru(nbd)Cl$_2$ to the synthesis of Ni-tet comprising nickel ions and 1,4-bis[(3,5-dimethyl)-pyrazol-4-yl]benzene ligands, or soaking of Ni-tet with a suspension of Ru(nbd)Cl$_2$ in polar solvent yielded the MOF composition (Ru@Ni-tet), which showed superior activity and selectivity for ethanol upgrading as compared to Ru@MFU-1. The optimal reaction temperature was determined to be 170° C. and ruthenium/nickel catalytic loadings between 1% and 3% ruthenium led to the highest turnover numbers. Entries (5)-(7) in Table 1 show a comparison of the MOF composition Ru@Ni-tet with different ruthenium loadings with a constant concentration of ruthenium present in the reaction mixture.

TABLE 1

Ethanol upgrading results with MOF compositions in neat ethanol containing sodium ethoxide (21%).

| | Ethanol Upgrading | MOF catalyst | Ru loading | T (° C.) | Time (hour) | TON | TOF |
|---|---|---|---|---|---|---|---|
| (1) | Comparison of | Ru@Ni-tet | 0.033 | 150 | 14.5 | 26,965 | 1,860 |
| (2) | reaction | Ru@Ni-tet | 0.016 | 160 | 19.75 | 122,342 | 6,194 |
| (3) | temperatures | Ru@Ni-tet | 0.016 | 170 | 14.5 | 152,699 | 10,531 |
| (4) | for Ru@Ni-tet | Ru@Ni-tet | 0.016 | 180 | 16 | 162,077 | 10,130 |
| (5) | Comparison of | Ru@Ni-tet | 0.016 | 170 | 14.5 | 152,699 | 10,531 |
| (6) | Ru loadings for | Ru@Ni-tet | 0.028 | 170 | 14.5 | 107,751 | 7,183 |
| (7) | Ru@Ni-tet | Ru@Ni-tet | 0.078 | 170 | 14.5 | 105,398 | 7,269 |
| (8) | Comparison | Ru@MFU-1 | 0.063 | 150 | 16.5 | 13,328 | 808 |
| (9) | of reaction | Ru@MFU-1 | 0.056 | 150 | 16 | 16,003 | 1,000 |

TABLE 1-continued

Ethanol upgrading results with MOF compositions in neat ethanol containing sodium ethoxide (21%).

| | Ethanol Upgrading | MOF catalyst | Ru loading | T (° C.) | Time (hour) | TON | TOF |
|---|---|---|---|---|---|---|---|
| (10) | temperatures | Ru@MFU-1 | 0.056 | 170 | 15 | 48,487 | 3,233 |
| (11) | for MFU-1 | Ru@MFU-1 | 0.018 | 170 | 14.5 | 153,471 | 10,584 |
| (12) | Maximizing | Ru@Ni-tet | 0.016 | 170 | 68 | 414,320 | 6,093 |
| (13) | TON | Ru@Ni-tet | 0.016 | 170 | 89 | 729,526 | 8,197 |
| (14) | Control | Ru(0) | | 170 | 14 | 0.3 | 8 | 1 |
| (15) | reactions | Ru(nbd)Cl$_2$ | | 170 | 14.5 | 15.8 | 16,623 | 1,164 |
| (16) | | Ru(nbd)Cl$_2$, Ni(OAc)$_2$ | | 170 | 14 | 22.0 | 23,172 | 1,598 |
| (17) | | Ru(nbd)Cl$_2$, Co(NO$_3$)$_2$ | | 170 | 14.5 | 19.0 | 20,133 | 1,388 |
| (18) | | Ni-tet | | 170 | 16.5 | 4.2 | 902 | 55 |
| (19) | | MFU-1 | | 170 | 14.5 | 2.1 | 521 | 36 |

Figure 10A:
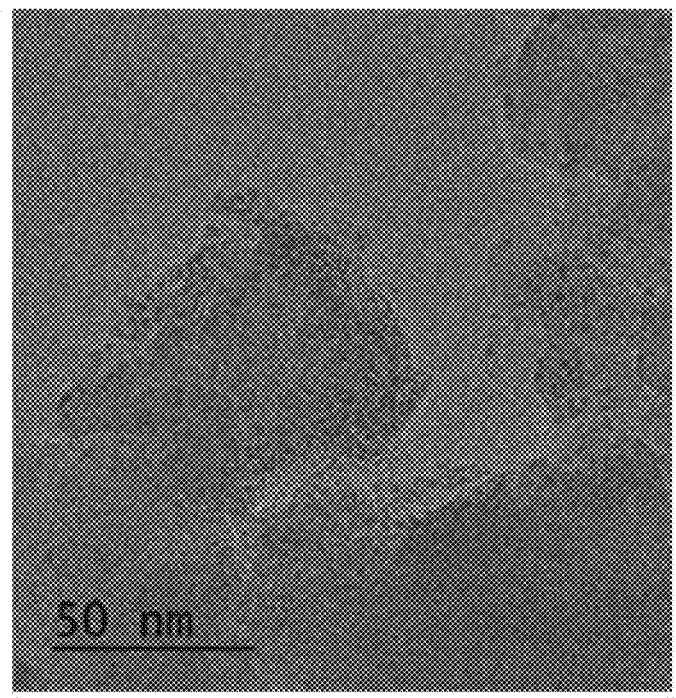
FIG. 10A shows, according to certain embodiments, a transmission electron microscopy (TEM) image of an exemplary recovered MOF composition
Figure 10B:
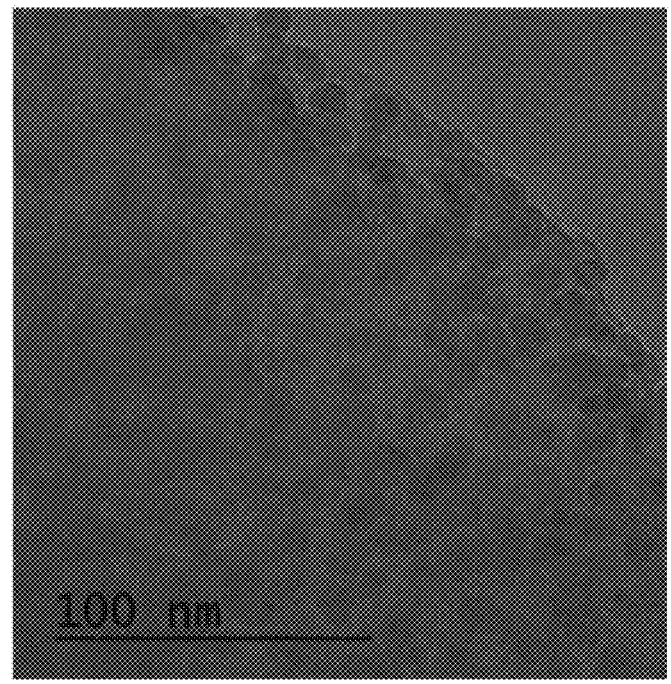
FIG. 10B shows, according to certain embodiments, a TEM image of an exemplary recovered MOF composition that is different from the MOF composition in FIG. 10A.
Figure 10C:
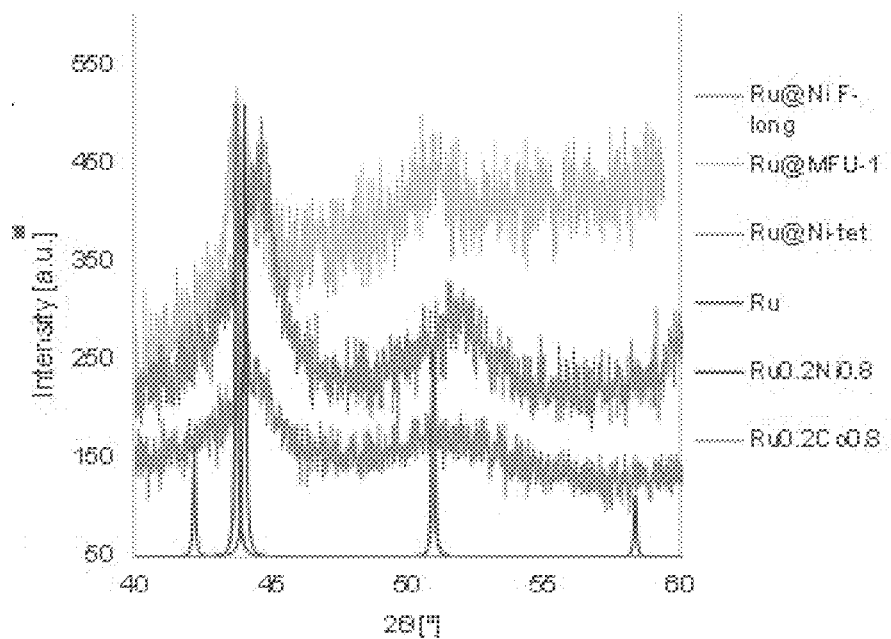
FIG. 10C shows, according to certain embodiments, PXRD chromatograms of various recovered exemplary MOF compositions.
Figure 10D:
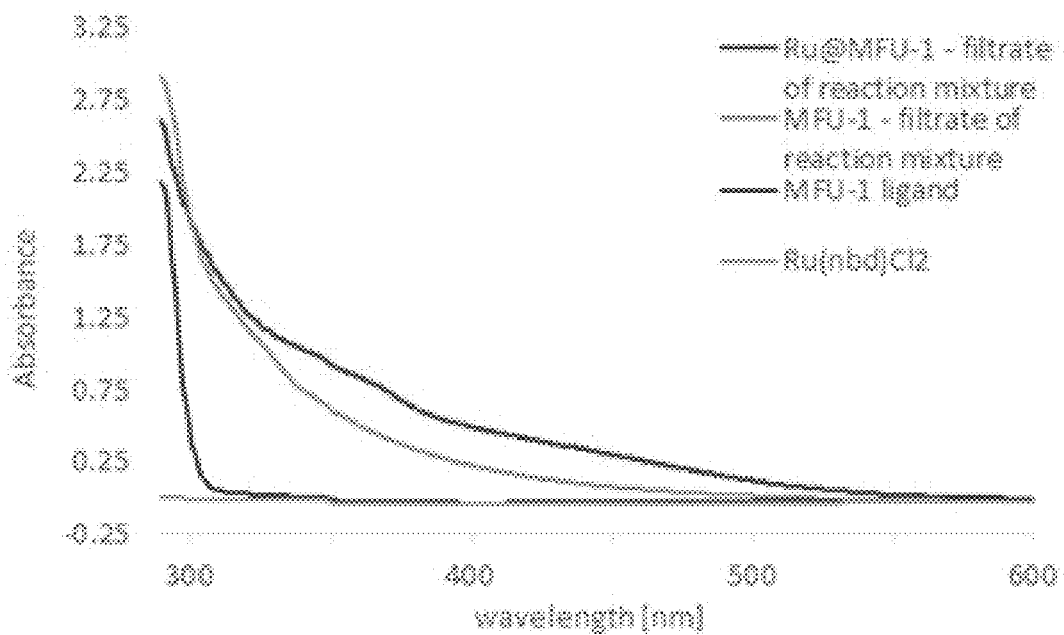
FIG. 10D shows, according to certain embodiments, UV-vis spectrograms of an exemplary recovered MOF composition compared to various starting materials.
Figure 10E:
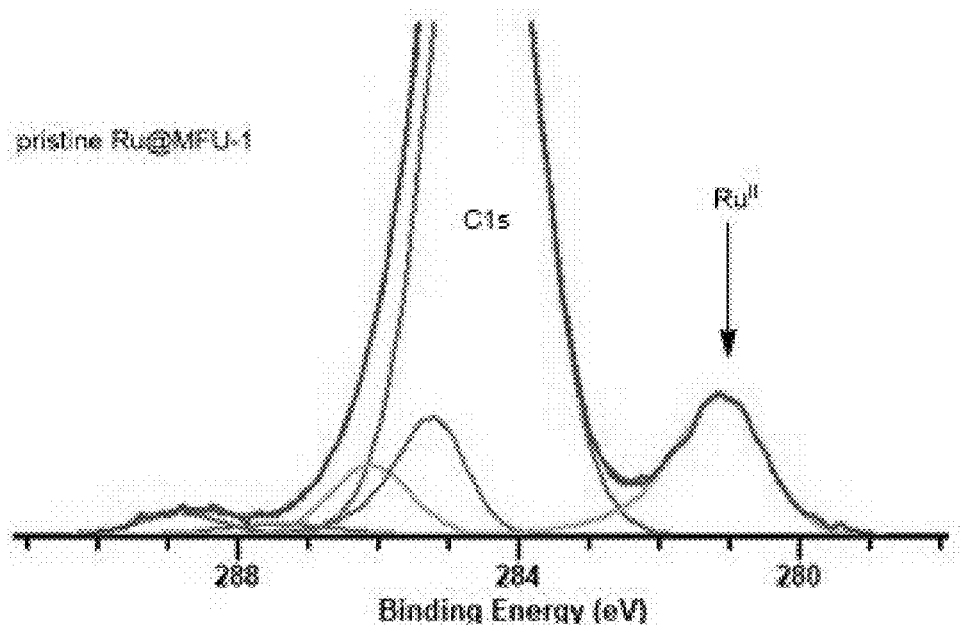
FIG. 10E shows, according to certain embodiments, XPS data for an exemplary MOF composition prior to upgrading alcohols.
Figure 10F:
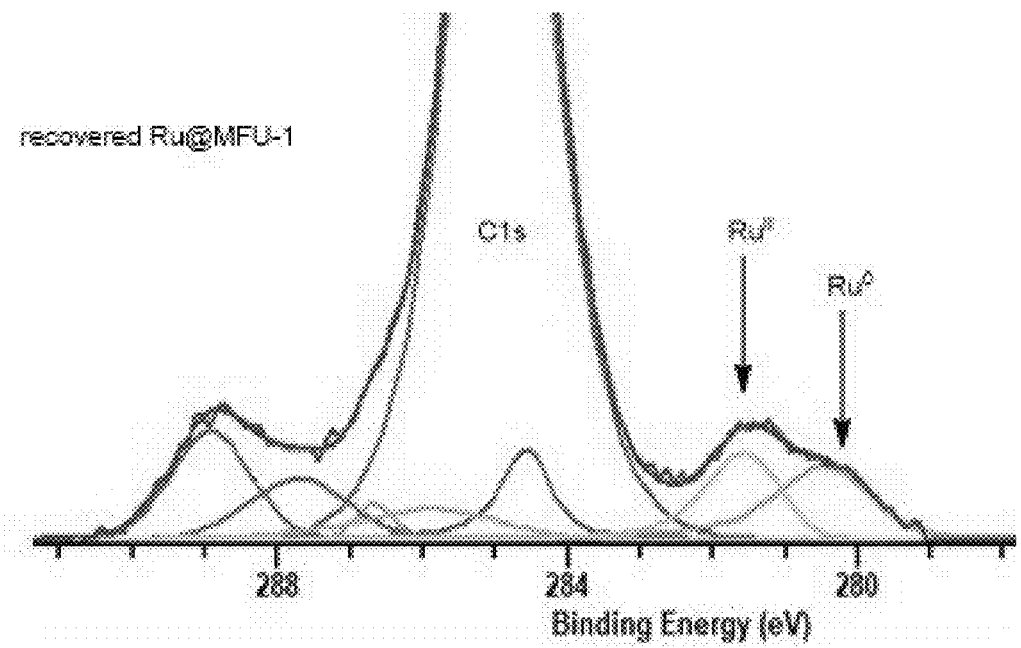
FIG. 10F shows, according to certain embodiments, XPS data for an exemplary recovered MOF composition.

High catalytic activity is maintained over extended reaction times (e.g. Table 1), despite the fact that the MOF compositions were rendered amorphous under the reaction conditions in under 30 minutes. Because MOF compositions recovered from ethanol upgrading reactions can be re-used without appreciable loss of activity, we concluded that the recovered catalyst is a more accurate representation of the active catalyst for ethanol upgrading than the pristine MOF composition system. Characterization of the recovered catalyst by PXRD, XPS, UV-vis and TEM suggests that catalytically active RuNi- or RuCo-containing nanoparticles are formed under the reaction conditions. TEM images of recovered catalyst batches of Ru@MFU-1 (FIG. 10B) confirmed the presence of metallic nanoparticles. Because the MOF compund loses crystallinity in the early stages of the catalytic reaction, the PXRD spectra of recovered catalyst batches do not contain peaks attributable to the MOF compound, but instead reveals broad peaks indicative of the formation of metal nanoparticles. Based on the presence of diffraction peaks around 2Θ values of 52°, the formation of nanoparticles with the composition Ru$_x$Ni$_{1-x}$ (derived from Ru@Ni-tet) and Ru$_x$Co$_{1-x}$ (derived from Ru@MFU-1) is proposed (FIG. 10C). Alloy formation accounts for the notable dependence of activity and selectivity on the MOF compound used despite the loss of the crystalline structure of the MOF compound. A comparison of the UV-vis spectra of Ru@MFU-1 and MFU-1 after they had been subjected to the reaction conditions for ethanol upgrading showed broad absorption features extending past 500 nm, which is consistent with the formation of metallic nanoparticles (FIG. 10D). XPS analysis confirmed that partial reduction of Ru$^{2+}$ present in the pristine catalyst batches (FIG. 10E) to Ru$^0$ (FIG. 10F) occurred under the reaction conditions.

Based on the TEM imaging, nanoparticles in the size range between 7.7 nm and 12.6 nm were obtained for Ru@MFU-1. Crystallite size analysis of the PXRD peaks using the Scherrer equation indicated that the metal nanoparticles formed are around 6.6 nm in size for Ru@MFU-1 and 6.6 nm for Ru@Ni-tet.

Partial release of nanoparticles from Ru@MFU-1 was observed at a reaction temperature of 120° C., while no remaining activity was detected in filtered solutions of ethanol upgrading reactions catalyzed by Ru@Ni-tet conducted at 160° C. for 14.5 hours. Prolonged heating at 170° C. led to partial nanoparticle release even with the optimized Ni-tet MOF compound. The catalytic activity of nanoparticles released from the MOF support remains intact, however, even though no ligands were added to stabilize the nanoparticles and minimize sintering. When the reaction mixture was filtered to remove all solids, and the filtered solution heated to 170° C. for an additional 17 hours, the TON increased. An increase in the TOF after liberation of the nanoparticles from the MOF support was calculated assuming complete release of the nanoparticles into solution. The increased activity of nanoparticles released into solution might be due to improved access of the reagents to the catalyst. It has been shown that the activity of the supported catalyst remains intact over the course of prolonged reaction times, whereas the increased activity of nanoparticles released from the MOF compound may come at the expense of reduced catalyst longevity due to disintegration or sintering of the nanoparticles. At a reaction temperature of 160° C., no activity was detected when the filtered reaction mixtures were subjected to further heating, which indicates that the nanoparticles remained attached to the MOF compound. The solid catalyst was collected via filtration, washed with water and air-dried before being subjected to a subsequent round of ethanol upgrading at 170° C. for 38 hours.

Figure 11:
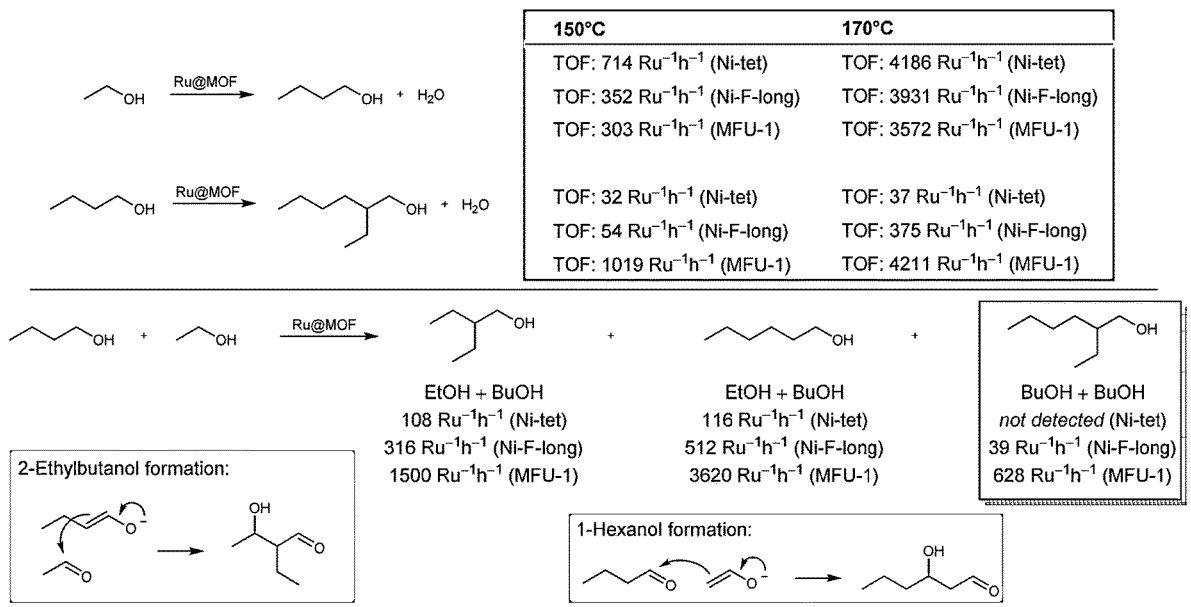
FIG. 11 shows, according to certain embodiments, various reaction schemes and mechanisms for the catalytic upgrading of alcohols with various exemplary MOF compositions at different reaction temperatures.

In addition to higher turnover frequencies, Ru@Ni-tet also displayed exceptional aldol condensation selectivity for the formation of 1-butanol (e.g. Table 1, (15): >99.8% selective 1-butanol formation). The acetaldehyde intermediate formed during ethanol upgrading is notoriously reactive towards aldol condensation, which may render it hard to selectively form 1-butanol via a Guerbet reaction. Without wishing to be bound by theory, butanol can undergo further reaction with acetaldehyde instead of reduction to butanol. Butanol itself is a good substrate for the Guerbet reaction and can undergo homo-coupling to form 2-ethyl-hexanol. The unexpected lack of aldol-derived side product formation led to the examination of the reactivity of Ru@MOF towards neat 1-butanol to eliminate concentration differences from the analysis (FIG. 11). While Ru@MFU-1 showed comparable activity for ethanol and butanol upgrading, the TOF for butanol upgrading was two orders of magnitude lower than the TOF for ethanol upgrading at 170° C. with Ru@Ni-tet. The low activity of the nickel-based catalyst towards butanol paired with the high activity of these systems towards ethanol explains why 1-butanol could be formed with an unprecedented combination of activity and selectivity. Without wishing to be bound by theory the unanticipated increase in selectivity for 1-butanol formation as the temperature of ethanol upgrading was increased from 150° C. to 170° C. can also be rationalized by observing that the TOF for ethanol upgrading increases more rapidly than the TOF for butanol upgrading for all catalysts.

On average, RuNi-containing nanoparticles recovered from butanol upgrading reactions have a diameter of 15.6 nm, whereas the diameter of nanoparticles recovered from ethanol upgrading reactions was 6.6 nm. To elucidate whether the reduced activity of the MOF composition for butanol upgrading was caused by inefficient formation of the active catalyst, alcohol upgrading experiments were conducted with 1:1 volumetric ratios of ethanol and butanol (FIG. 11). Nanoparticles recovered from mixed alcohol experiments were comparable in size to ethanol rather than butanol upgrading reactions, but the presence of small nanoparticles did not increase the amount of the 2-ethylhexanol formed. Without wishing to be bound by theory, the larger size of RuNi-containing nanoparticles formed in butanol upgrading reactions therefore may not be the cause but a consequence of the lower activity of the MOF composition towards butanol: slower dehydrogenation of butanol leads to a lower partial pressure of $H_2$, which reduces the rate of reduction of $Ru^{2+}$, and may, in turn, cause larger RuNi-containing nanoparticles to form. 1-hexanol and 2-ethylbutanol were formed in preference to 2-ethylhexanol in mixed alcohol upgrading experiments, indicating a higher concentration of acetaldehyde compared to butanol. Formation of comparable amounts of 1-hexanol and 2-ethylbutanol was consistent with dehydrogenation rather than enolization occurring less efficiently for ethanol than butanol. Therefore, the lower activity towards 1-butanol may be due to higher kinetic barriers for butanol dehydrogenation compared to ethanol dehydrogenation with nickel-based MOF compositions. Selective ethanol upgrading originating from a lower dehydrogenation barrier is surprising because ethanol dehydrogenation was calculated to be 5.2 kcal·mol$^{-1}$ more endergonic than butanol dehydrogenation at 170° C.

In addition to 1-butanol, sodium acetate is also formed under the reaction conditions. Given the absence of ethyl acetate in the final reaction product, the side product may be formed via a Cannizzaro reaction mechanism. Cannizzaro or Tishchenko reactions competing with the Guerbet reaction may lead to the consumption of starting material, but unlike the formation of other aldol-derived reaction products, does not lead to challenges in the isolation and purification of the 1-butanol product. Sodium acetate and 1-butanol were formed in a molar ratio of 1:8.1 (entry (3) of Table 1). Despite the low amounts of side products formed, solid sodium acetate leads to an increase in viscosity of the reaction mixture, which interferes with efficient access of the substrate to the heterogeneous catalyst and limits the conversion to butanol that can currently be achieved. Given that no sodium acetate formation could be detected during ethanol upgrading reactions with nanoparticles released from the MOF support into solution, it was speculated that the Cannizzaro side reaction is not an inherent issue of the catalytic system, but one that can be addressed through tuning of the MOF compound.

Example 3

Ru@MFU-1 compositions were synthesized with various reaction components and conditions, as shown in Table 2.

TABLE 2

Various reaction components and conditions for the synthesis of Ru@MFU-1.

| | Ruthenium source | Solvent | Reaction time | Ru loading |
|---|---|---|---|---|
| (1) | Ru(dmso)$_4$Cl$_2$ (0.04 equiv per Co) | Co-synthesis | | Co:Ru = 1:0.024 |
| (2) | [Ru(norbornene)Cl$_2$]$_n$ (0.29 equiv per Co) | DMF | 4 days | Co:Ru = 1:0.021 |

TABLE 2-continued

Various reaction components and conditions for the synthesis of Ru@MFU-1.

| | Ruthenium source | Solvent | Reaction time | Ru loading |
|---|---|---|---|---|
| (3) | [Ru(COD)Cl$_2$]$_n$ (0.25 equiv per Co) | DMF | 3 days | Co:Ru = 1:0.018 |
| (4) | [Ru(norbornene)Cl$_2$]$_n$ (0.16 equiv per Co) | MeCN | 3 days | Co:Ru = 1:0.020 |
| (5) | [Ru(norbornene)Cl$_2$]$_n$ (0.16 equiv per Co) | DMF, 80° C. | 3 h | Co:Ru = 1:0.045 |
| (6) | [Ru(norbornene)Cl$_2$]$_n$ (0.16 equiv per Co) | DMF, 80° C. | 3 h | Co:Ru = 1:0.049 |

As a non-limiting embodiment, the synthetic procedure of entry (5) in Table 2 is described in detail. Under air, 220 mg of MFU-1 and 20 mg of Ru(nbd)Cl$_2$ were placed in a pyrex reaction vessel and 100 mL of DMF was added. The reaction mixture was left to stir for 3 hours at 80° C. and filtered over a medium frit to isolate Ru@MFU-1. Residual Ru(nbd)Cl$_2$ was removed by washing three times with 100 mL of DMF and three times with 100 mL of ethanol. After drying under air at room temperature, 217 mg of a dark blue solid was collected. The ruthenium content of the sample was measured by ICP-MS and the structural integrity of the MOF was verified by PXRD. Cobalt was not detected by ICP-MS analysis neither in the filtrate of the reaction mixture nor in the solvent used to wash Ru@MFU-1.

Example 4

Ru@Ni-tet compositions were synthesized with various reaction components and conditions, as shown in Table 4.

TABLE 4

Various reaction components and conditions for the synthesis of Ru@Ni-tet.

| | Ruthenium source | solvent | Reaction time | Ru loading |
|---|---|---|---|---|
| (1) | [Ru(norbornene)Cl$_2$]$_n$ (0.16 equiv per Ni) | MeCN | 4 days | Ni:Ru = 1:0.033 |
| (2) | [Ru(norbornene)Cl$_2$]$_n$ (0.13 equiv per Ni) | DMF | 1.5 days | Ni:Ru = 1:0.079 |
| (3) | [Ru(norbornene)Cl$_2$]$_n$ (0.053 equiv per Ni) | Co-synthesis | | Ni:Ru = 1:0.028 |
| (4) | [Ru(norbornene)Cl$_2$]$_n$ (0.025 equiv per Ni) | Co-synthesis | | Ni:Ru = 1:0.016 |
| (5) | [Ru(norbornene)Cl$_2$]$_n$ (0.10 equiv per Ni) | Co-synthesis | | Ni:Ru = 1:0.052 |
| (6) | [Ru(norbornene)Cl$_2$]$_n$ (0.025 equiv per Ni) | Co-synthesis | | Ni:Ru = 1:0.022 |
| (7) | [Ru(COD)Cl$_2$]$_n$ (0.025 equiv per Ni) | Co-synthesis | | Ni:Ru = 1:0.014 |

As a non-limiting embodiment, the synthetic procedure of entry (4) in Table 4 is described in detail. To a suspension of 73 mg of Ni(OAc)$_2$·4H$_2$O and 2 mg of Ru(nbd)Cl$_2$ in 7 ml NMP, 105 mg of the H$_2$tet ligand was added at room temperature under stirring. The reaction mixture was then heated to 150° C. and left to stir for 7 hours. The solid was filtered off and washed with DMF (twice), ethanol (3 times) and acetone (3 times) to yield 110 mg brown solid. The ruthenium content of the sample was measured by ICP-MS and the structural integrity of the MOF was verified by PXRD.

Example 5

Figure 12A:
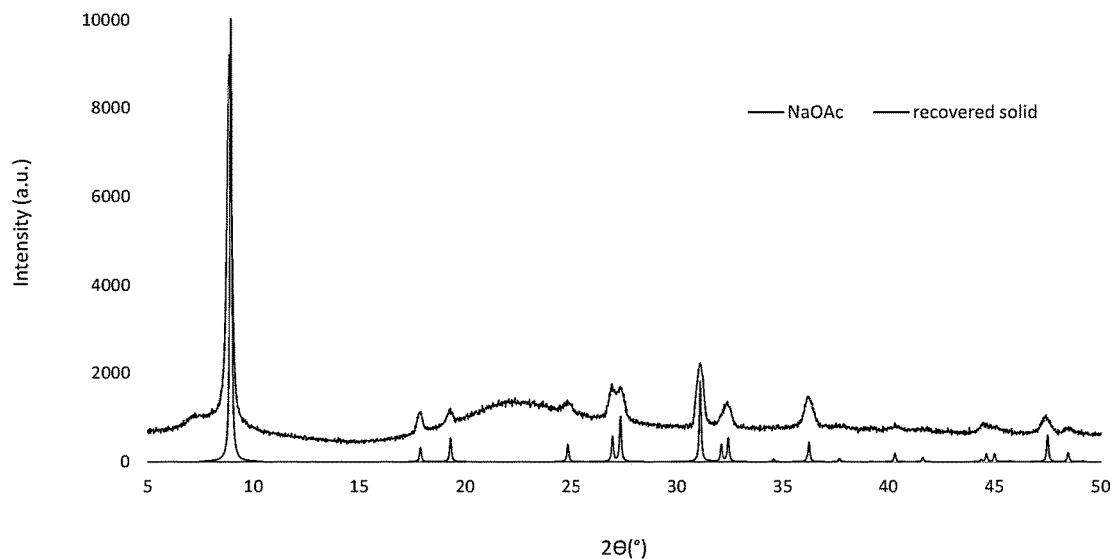
FIG. 12A shows, according to certain embodiments, PXRD analysis of recovered solid from the reaction mixture.

At the end of a typical catalytic reaction using a MOF composition, the Paar reactor contained a liquid phase which was mainly composed of ethanol and butanol (and was analyzed by GC-MS after addition of the internal standard m-xylene and filtration), as well as the solid MOF composition and varying amounts of a white solid. The solid was separated by filtration and analyzed by PXRD and ICP-MS. Comparison of the PXRD data to authentic samples showed that the white solid observed is NaOAc or NaOAc·3H$_2$O, depending on the reaction conditions of ethanol upgrading, as shown in FIG. 12A.

Figure 12B:
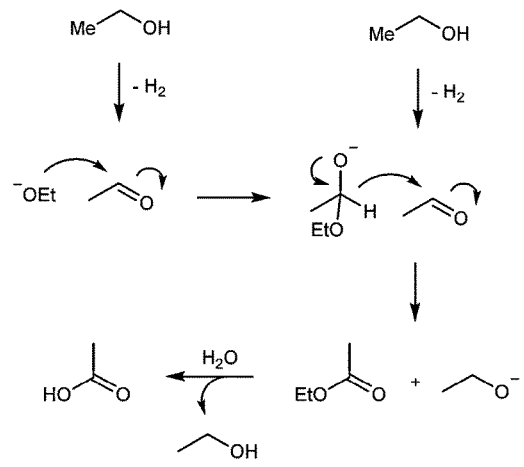
FIG. 12B shows, according to certain embodiments, reaction schemes for the Tishchenko reaction and the Cannizzaro reaction.
Figure 12B:
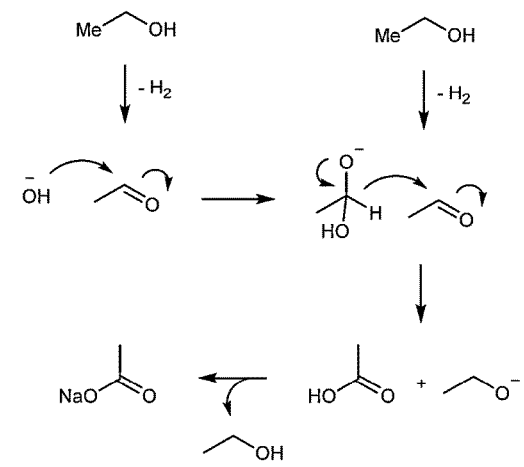

Sodium acetate is a commonly observed side product of ethanol upgrading via a Guerbet reaction. A Cannizzaro or a Tishchenko mechanism, as shown in FIG. 12B, could be responsible for the formation of sodium acetate under the reaction conditions. Given that no ethyl acetate was detected by GC-MS, a Cannizzaro mechanism was favored to account for the formation of sodium acetate with the MOF composition.

Example 6

Under the reaction conditions of ethanol upgrading, MOF precursor compositions, which contain a Ru$^{2+}$ salt trapped within the pores of the MOF, is converted into the active catalyst. Because the spent catalyst can be reused without a noticeable decrease in activity, catalyst batches recovered from the reaction mixture were washed with water, dried under air, and analyzed to gain insight into the active catalytic species.

Reduction of the encapsulated ruthenium salt led to the formation of RuNi-containing nanoparticles in the case of nickel-based MOF compounds and RuCo-containing nanoparticles in the case of cobalt-based MOF compounds. The size of the nanoparticles was inferred from the full width at half maximum of the diffraction peak at 2Θ=44° using the Scherrer equation.

Figure 13A:
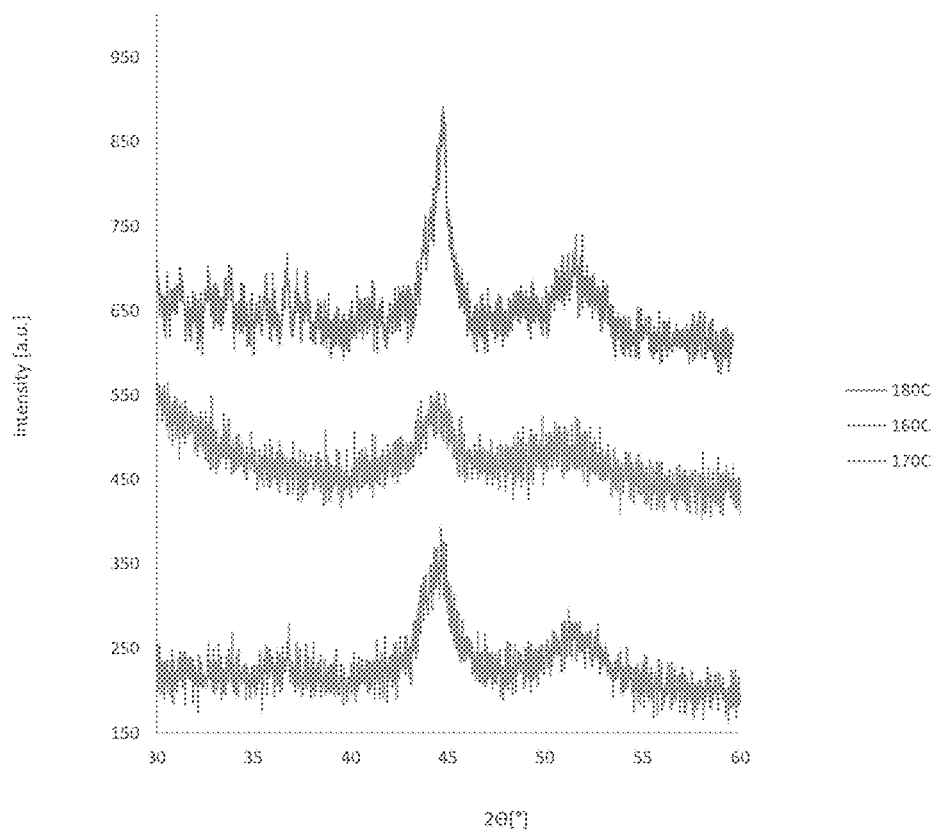
FIG. 13A shows, according to certain embodiments, the PXRD analysis of exemplary recovered MOF compositions used for alcohol upgrading reactions conducted at various temperatures.

It was found that there was a dependence of the size of the nanoparticle on the temperature of the upgrading reaction, as shown in FIG. 13A and Table 5.

TABLE 5

Sizes of RuNi-containing nanoparticles recovered from ethanol upgrading reactions conducted at different temperatures.

| Temperature (° C.) | Size of RuNi-containing nanoparticles (nm) |
| --- | --- |
| 160 reaction | 4.7; 4.5; 3.8 |
| 170 reaction | 11.4; 10.5; 8.2; 7.1; 6.6; 4.8; 3.8 |
| 180 reaction | 7.1 |

Figure 13B:
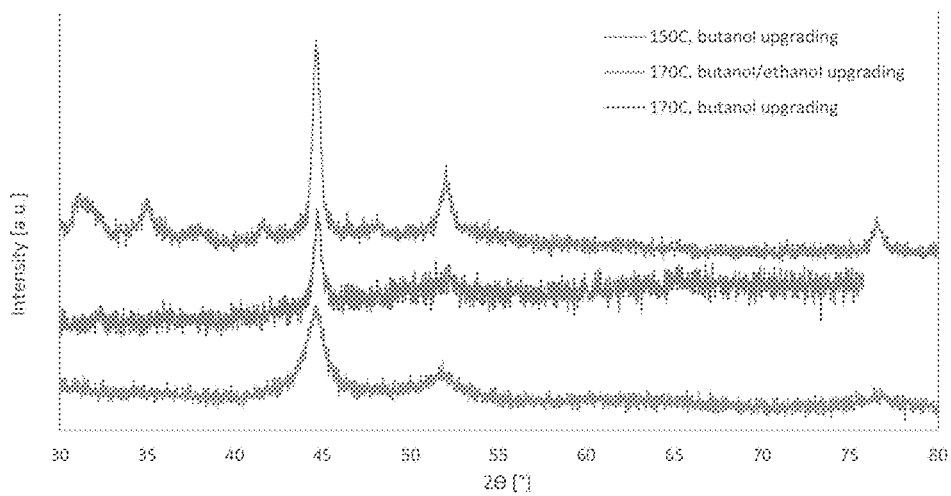
FIG. 13B shows, according to certain embodiments, the PXRD analysis of exemplary recovered MOF compositions used for alcohol upgrading reactions conducted with various alcohols and/or at various temperatures.

Ru@Ni-tet recovered from butanol upgrading reactions conducted at 150° C. and 170° C., respectively, show that larger particles are formed than for ethanol upgrading reactions. Particles formed in upgrading of mixtures of ethanol and butanol are comparable in size to particles formed in ethanol upgrading reactions, as shown in FIG. 13B and Table 6.

TABLE 6

Sizes of RuNi-containing nanoparticles recovered from upgrading reactions conducted with different alcohols and/or at different temperatures.

| Substrate | Temperature (° C.) | Size of RuNi-containing nanoparticles (nm) |
| --- | --- | --- |
| 1-butanol | 150 | 14.9 |
| 1-butanol | 170 | 16.3 |
| ethanol:1-butanol 1:1 (v/v) | 170 | 4.8 |

The lower activity of MOF composition catalysts towards butanol renders likely that the larger particles formed in butanol upgrading reaction are a result of the lower concentration of hydrogen gas present leading to slower reduction of Ru$^{2+}$ to Ru$^0$. Without wishing to be bound by theory, a higher barrier for butanol compared to ethanol dehydrogenation would account both for the lower rate of the Guerbet reaction with butanol as the substrate as well as to slower ruthenium reduction leading to the formation of larger nanoparticles. The nanoparticles in the upgrading of a mixture of ethanol and butanol are of a similar size to those observed for ethanol upgrading reactions since the more facile ethanol dehydrogenation reaction leads to a sufficient partial pressure of hydrogen to efficiently reduce ruthenium. No increase in the activity of the MOF composition towards butanol upgrading was observed in the presence of ethanol. The larger nanoparticles observed for butanol upgrading reactions are therefore more likely to be a consequence of the lower activity of the catalyst towards butanol than ethanol, at least in part due to the reduced surface area of the active catalytst. The unusually low amount of higher aldol products observed for ethanol upgrading reactions further supports the hypothesis that the higher activity of the catalyst towards ethanol may be inherent to the system and does not result from less efficient in situ catalyst activation in the absence of ethanol.

Figure 13C:
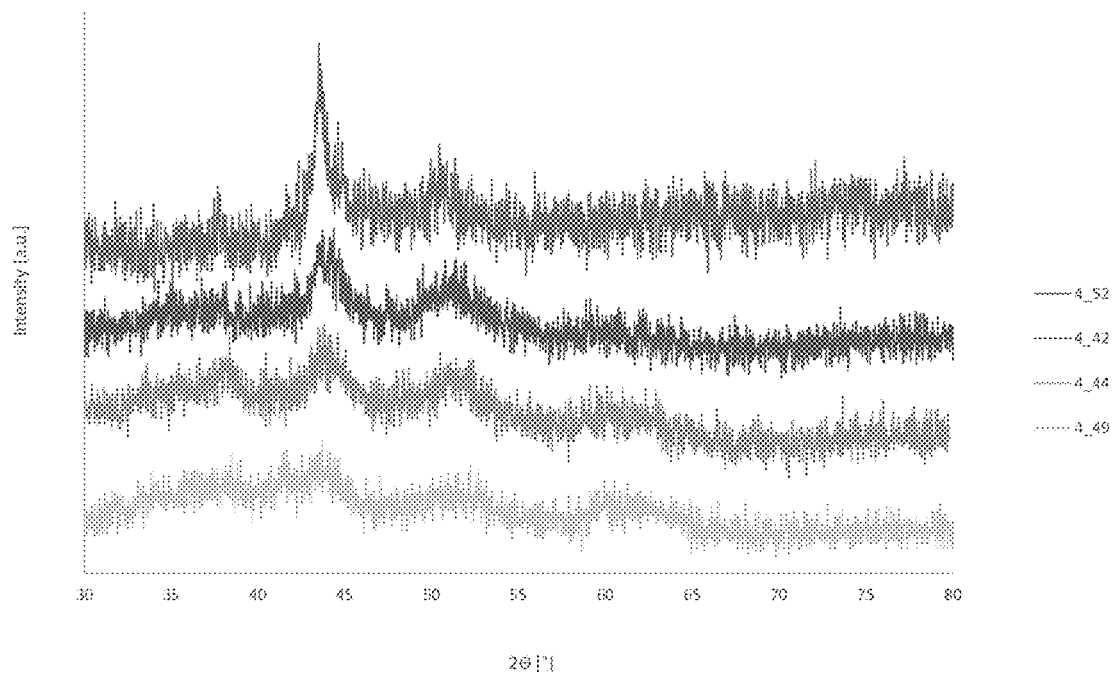
FIG. 13C shows, according to certain embodiments, the PXRD analysis of exemplary recovered MOF compositions used for upgrading reactions with various concentrations of sodium ethoxide base.

The size of nanoparticles formed as well as the presence of nickel hydroxide in the recovered catalytic mixture is influenced by the concentration of sodium ethoxide used in the ethanol upgrading reaction, as shown in FIG. 13C. Sample 4_49 (21% NaOEt solution) shows the smallest RuNi-containing particle, as well as the highest ratio of nickel hydroxide to RuNi, followed by sample 4_44 (15.75% NaOEt solution), sample 4_42 (10.5% NaOEt solution) and sample 4_52 (5.25% NaOEt solution). The formation of larger RuNi-containing particles seen in sample 4_52 was likely caused by the low concentration of base reducing the dehydrogenation rate of ethanol, the resulting low hydrogen pressure in turn causing slow reduction of ruthenium and the formation of large particles.

Figure 13D:
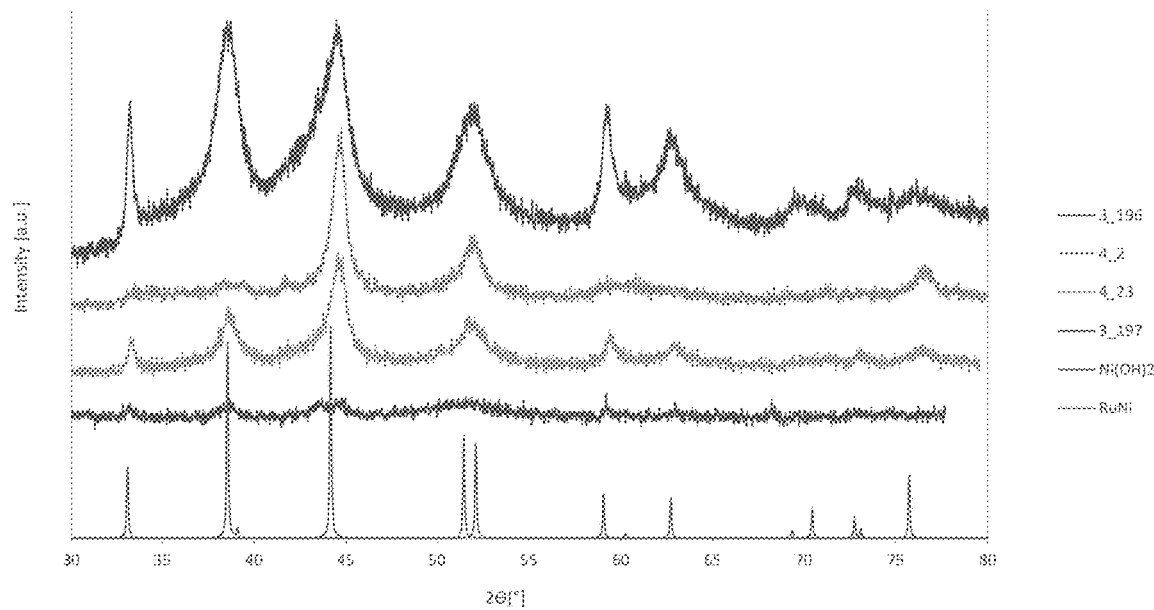
FIG. 13D shows, according to certain embodiments, the PXRD analysis of exemplary recovered MOF compositions used for upgrading reactions displaying the formation of nickel hydroxide.
Figure 13E:
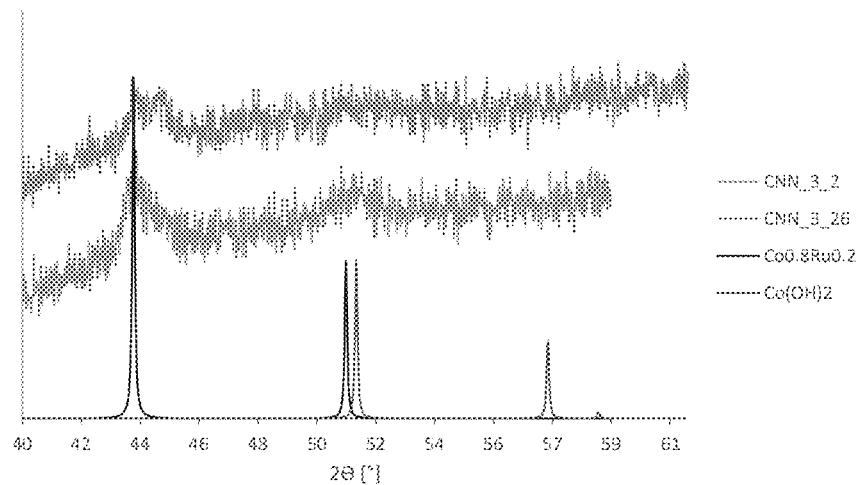
FIG. 13E shows, according to certain embodiments, the PXRD analysis of exemplary recovered MOF compositions used for upgrading reactions displaying evidence for the formation of cobalt hydroxide.

PXRD patterns of recovered MOF compositions comprising Ni reveal the presence of nickel hydroxide in addition to RuNi-containing nanoparticles, as shown in FIG. 13D. Neither the reaction time, temperature, conversion, nor the amount of catalyst used in reactions appears to correlate with the amount of nickel hydroxide formed during ethanol upgrading. Larger amounts of nickel hydroxide are observed, however, for MOF-compositions with higher ruthenium loadings. Given that lower ruthenium loadings also lead to higher turnover numbers per ruthenium center, the formation of nickel hydroxide may inhibit the catalytic reaction. Sample 3_197 (Ni:Ru=1:0.079) showed the highest ratio of nickel hydroxide to RuNi-containing nanoparticles, followed by sample 3_196 (Ni:Ru=1:0.028) and sample 4_23 (Ni:Ru=1:0.022), with sample 4_2 (Ni:Ru=1:0.016) showing the highest RuNi-containing nanoparticles to nickel hydroxide ratio. Cobalt hydroxide was also observed in recovered MOF compositions comprising Co, as shown in FIG. 13E.

Figure 14:
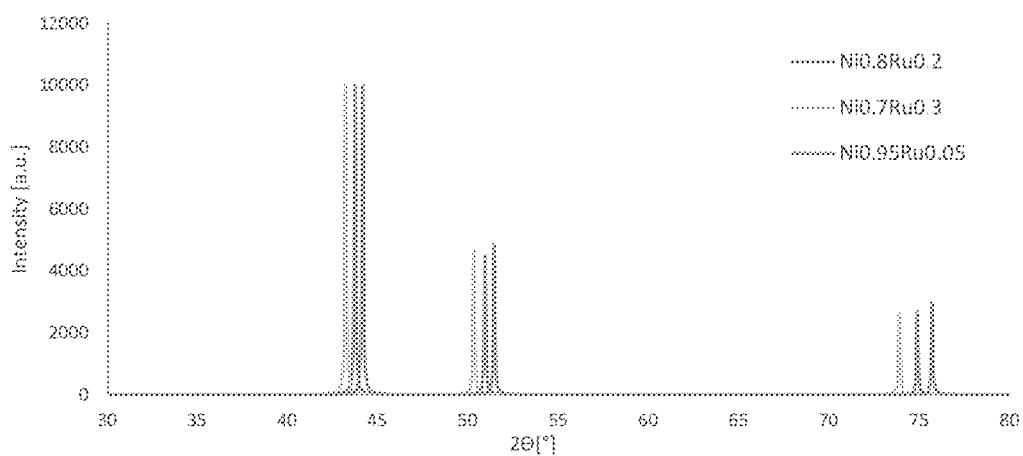
FIG. 14 shows, according to certain embodiments, the predicted PXRD analysis of various RuNi-containing alloys.
Figure 15A:
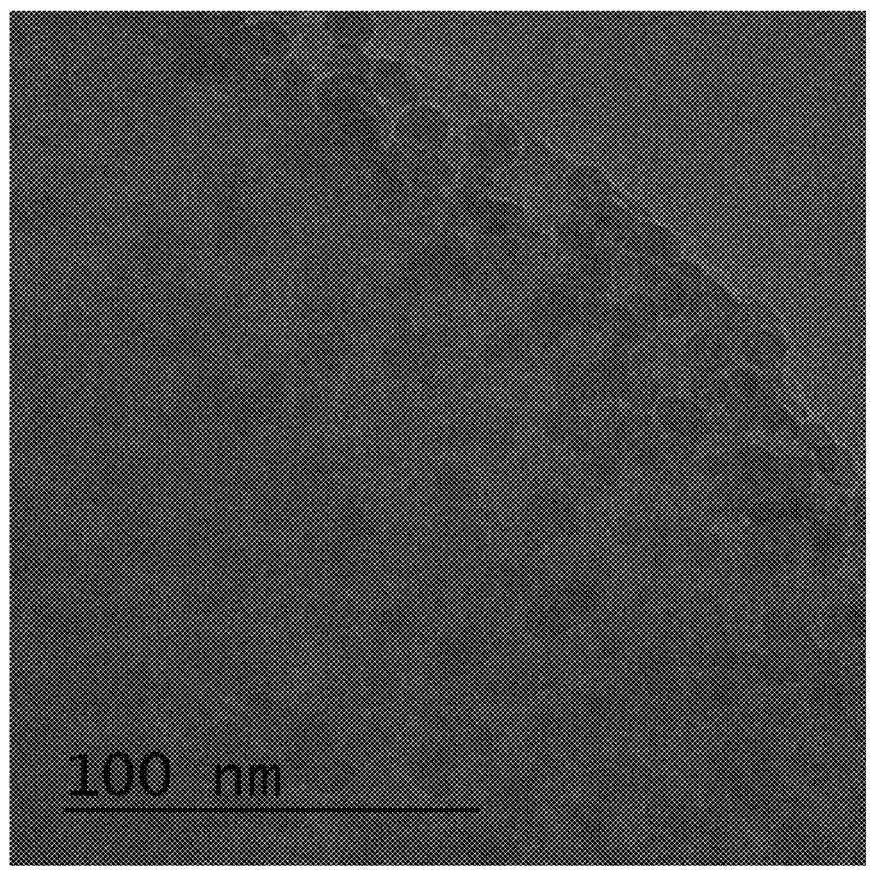
FIG. 15A shows, according to certain embodiments, a TEM image of an exemplary MOF composition recovered from ethanol upgrading.
Figure 15B:
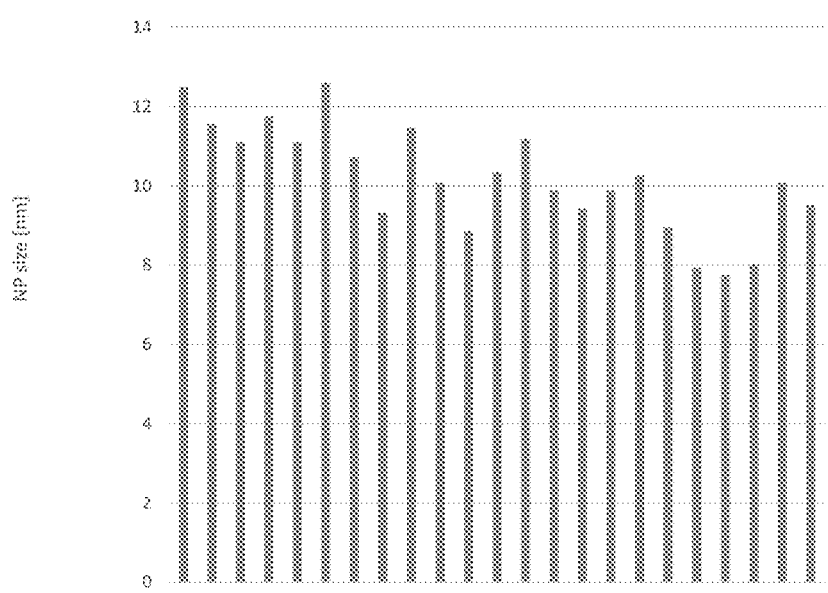
FIG. 15B shows, according to certain embodiments, the diameter of nanoparticles of the MOF composition shown in FIG. 15A.
Figure 15C:
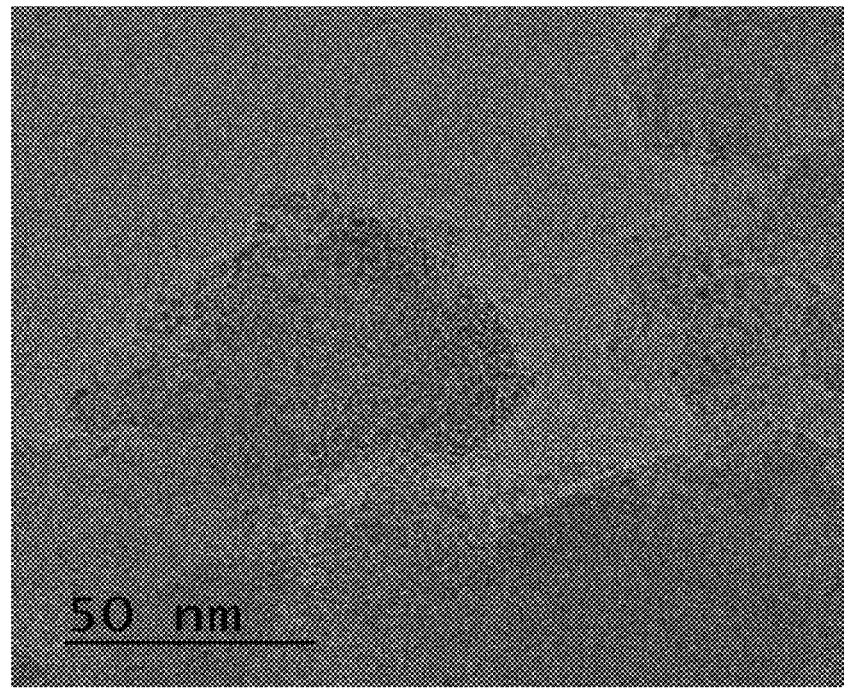
FIG. 15C shows, according to certain embodiments, a TEM image of an exemplary MOF composition recovered from ethanol upgrading that is different than the exemplary MOF composition in FIG. 15A.
Figure 15D:
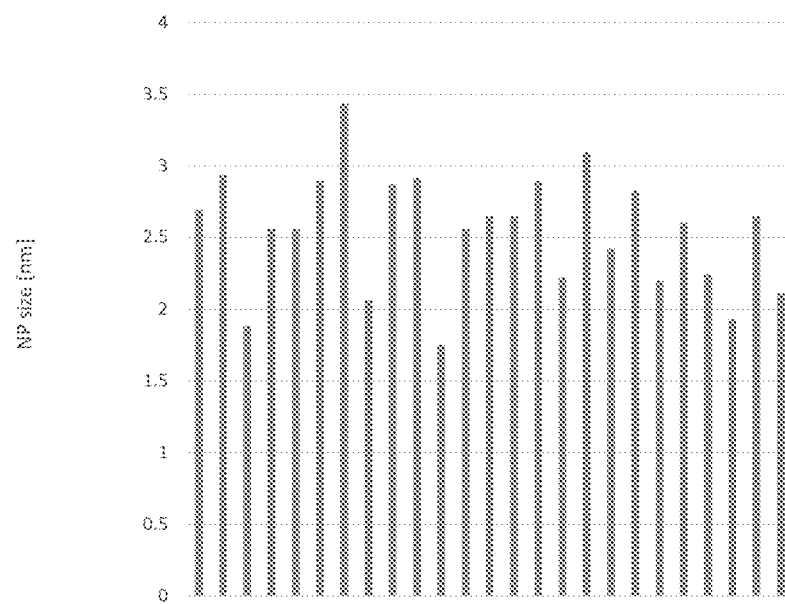
FIG. 15D shows, according to certain embodiments, the diameter of nanoparticles of the MOF composition shown in FIG. 15C.
Figure 16A:
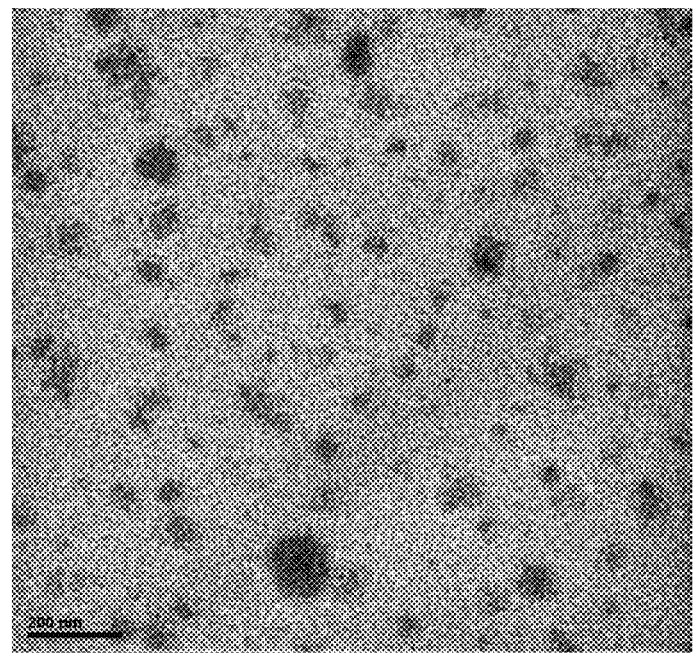
FIG. 16A shows, according to certain embodiments, a TEM image of filtered reaction mixture of an exemplary MOF composition synthesized with [RuCl$_2$(COD)]$_2$ recovered from ethanol upgrading with sodium hydroxide and one week reaction time at 120° C.
Figure 16B:
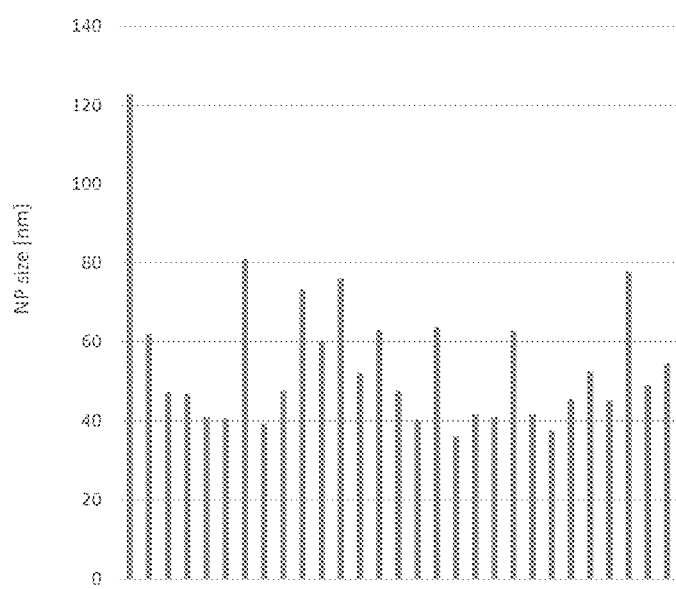
FIG. 16B shows, according to certain embodiments, the diameter of nanoparticles of the MOF composition shown in FIG. 16A.
Figure 16C:
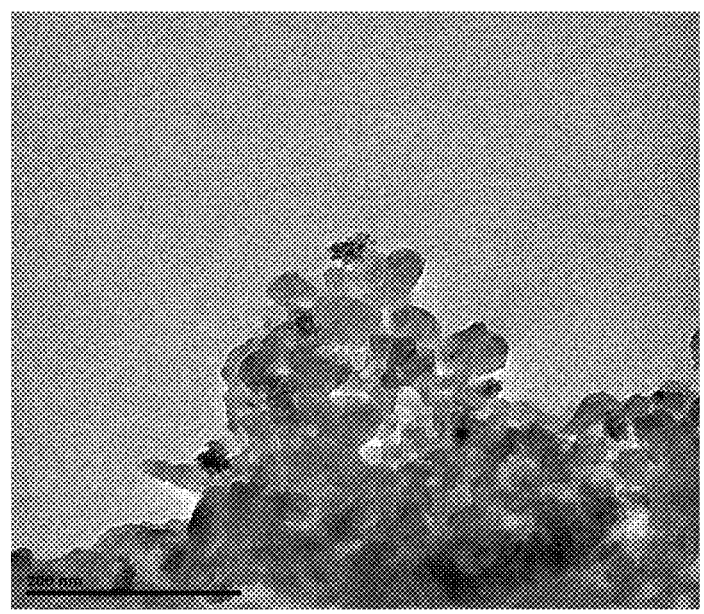
FIG. 16C shows, according to certain embodiments, a TEM image of filtered reaction mixture of an exemplary MOF composition synthesized with [RuCl$_2$(nbd)]$_2$ recovered from ethanol upgrading with sodium hydroxide and one week reaction time at 120° C.
Figure 16D:
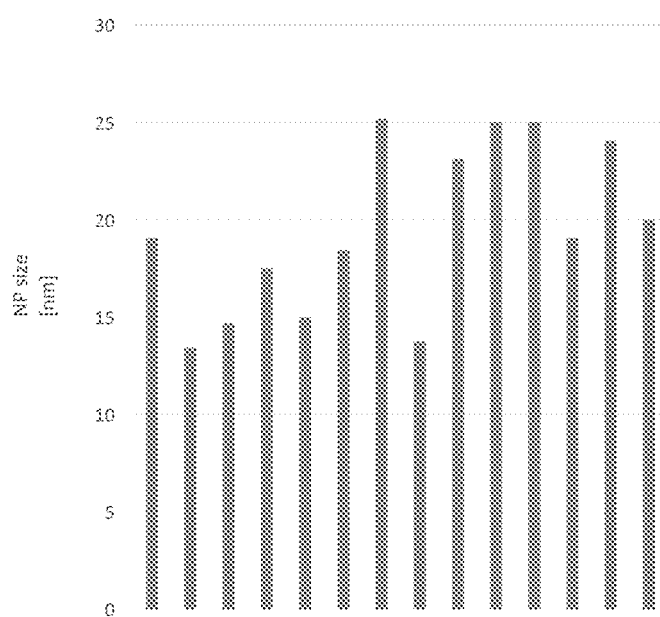
FIG. 16D shows, according to certain embodiments, the diameter of nanoparticles of the MOF composition shown in FIG. 16C.

The predicted diffraction peaks of ruthenium-nickel alloys shift to higher 2Θ values as the amount of nickel in the alloy increases, as shown in FIG. 14. As the diffraction peaks of the RuNi nanoparticles formed in the ethanol upgrading reaction appear at higher 2Θ values than those predicted for Ru$_{0.05}$Ni$_{0.95}$, it appears likely that the nanoparticles formed under the reaction conditions are largely composed of nickel.

Upon prolonged reaction, nanoparticles can be released from the MOF support. Leaching of the catalytically active nanoparticles was particularly apparent when NaOH was used as a base instead of sodium ethoxide. When an ethanol upgrading reaction mixture was filtered after one week of heating and the filtrate was subjected to TEM analysis, the presence of nanoparticles in solution was established. Released nanoparticles were larger in size than those found for recovered MOF compositions. The increased size may be due either to the lack of MOF compound or the prolonged reaction time which could have cause particle sintering. FIG. 15A to FIG. 15D show TEM images and the diameter of nanoparticles of recovered MOF compositions.

Particles other than the RuCo-containing nanoparticles formed under the reaction conditions are visible in the TEM image of the filtered reaction mixture, as shown in FIG. 16A to FIG. 16D. When NaOH is used as the base instead of sodium ethoxide, the MFU-1 MOF not only loses crystallinity, but decomposes with the formation of small particles that can pass through the filter.

Example 7

XPS analysis of Ru@MFU-1 synthesized by soaking the MOF MFU-1 in a suspension of Ru(nbd)Cl$_2$ in DMF at 80° C. or of Ru(COD)Cl2 in acetonitrile at room temperature showed that the oxidation state of ruthenium incorporated into the MOF is +2. Reduction of Ru@MFU-1 with H$_2$ led to a mixture of Ru$^{2+}$ and Ru$^0$. Likewise, a mixture of Ru$^{2+}$ and Ru$^0$ was detected for Ru@MFU-1 recovered from the ethanol upgrading reaction mixture. Partial reduction of Ru$^{2+}$ to Ru$^0$ incorporated into the MOF therefore occurs under the reaction conditions.

XPS analysis of Ru@Ni-tet prepared by synthesis of the MOF compound compiring nickel in the presence of Ru(nbd)Cl$_2$ showed Ni$^{2+}$ species were present. After use of the catalyst for ethanol upgrading, however, Ni$^0$ was present, which is in line with the proposed formation of RuNi-containing nanoparticles when Ru@Ni-tet is used for alcohol upgrading.

Example 8

For the MOF compositions used for alcohol upgrading reactions, the amount of higher aldol products formed is usually too low to be visible in the GC-MS mass trace and hard to see in the FID trace. The reaction shows poor conversion and higher degrees of side product formation, however, if ethanol upgrading is conducted with more headspace. Ethanol upgrading was optimized with a Paar reactor that is ~70% filled with the reagent solution. When the reagent volume was reduced to ~20% of the reactor, increased side product formation rendered side products clearly visible in the GC-MS FID trace, as shown in FIG. 17A to FIG. 17D.

Figure 17A:
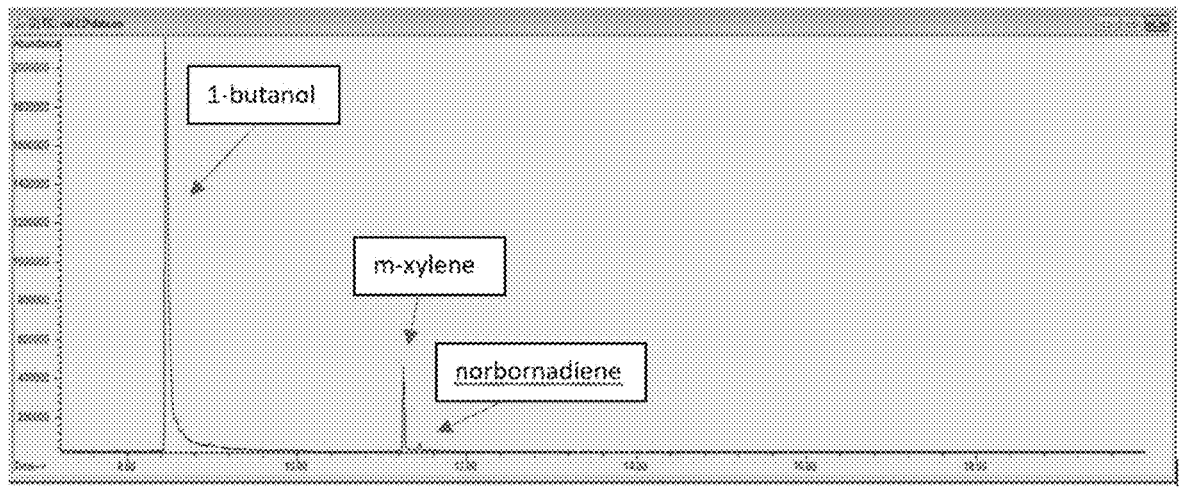
FIG. 17A shows, according to certain embodiments, a mass chromatogram for ethanol upgrading with an exemplary MOF composition at 170° C. for 89 hours.

FIG. 17A shows the mass chromatogram for ethanol upgrading with Ru@Ni-tet at 170° C. for 89 hours. The mass chromatogram shows the 1-butanol product, the m-xylene internal standard, and norbornadiene released from the Ru(nbd)Cl$_2$ precursor incorporated into the MOF composition. Table 7 shows the quantification of products.

TABLE 7

Quantification of products shown in the mass chromatogram of FIG. 17A.

| | Retention time: | Amount (microliters) | Amount (mmol) | TON (Ru$^{-1}$) | TOF (Ru$^{-1}$h$^{-1}$) |
|---|---|---|---|---|---|
| 1-butanol | 8.3 min | 2187 | 23.9 | 251,502 | 2826 |
| m-xylene (standard) | 11.2 min | | | | |

Figure 17B:
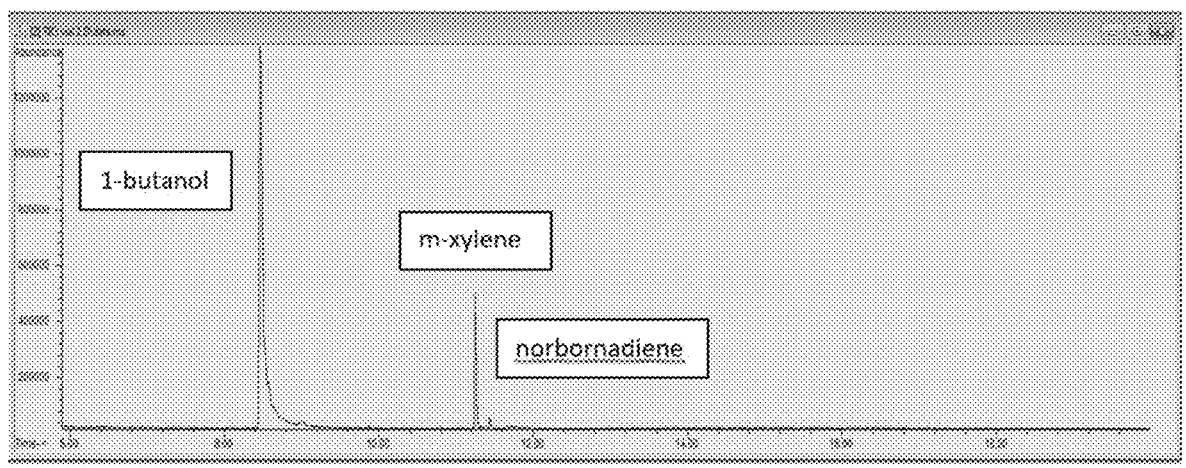
FIG. 17B shows, according to certain embodiments, a mass chromatogram for ethanol upgrading with an exemplary MOF composition at 170° C. for 14.5 hours

FIG. 17B shows the mass chromatogram for ethanol upgrading with Ru@Ni-tet at 170° C. for 14.5 hours. The mass chromatogram shows the 1-butanol product, the m-xylene internal standard, and norbornadiene released from the Ru(nbd)Cl$_2$ precursor incorporated into the MOF composition. Table 8 shows the quantification of products.

TABLE 8

Quantification of products shown in the mass chromatogram of FIG. 17B.

| | Retention time: | Amount (microliter) | Amount (mmol) | TON (Ru$^{-1}$) | TOF (Ru$^{-1}$h$^{-1}$) |
|---|---|---|---|---|---|
| 1-butanol | 8.3 min | 1332 | 14.56 | 60,692 | 4185 |
| m-xylene (standard) | 11.2 min | | | | |

Figure 17C:
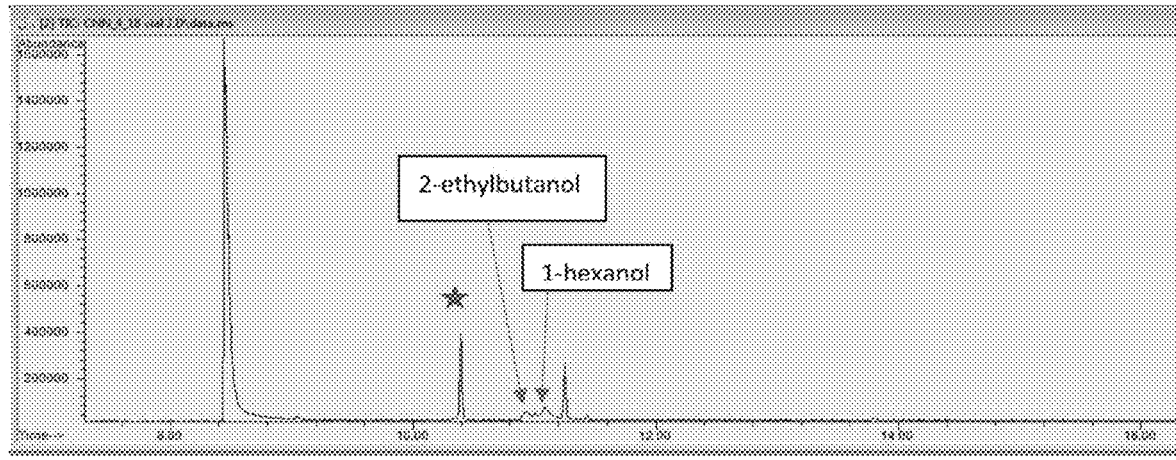
FIG. 17C shows, according to certain embodiments, a mass chromatogram for ethanol upgrading with [RuCl$_2$(COD)]$_2$ at 170° C. for 6 hours.

FIG. 17C shows the mass chromatogram for ethanol upgrading with Ru(COD)Cl$_2$ at 170° C. for 6 hours. The peak marked with the blue star is dimerized acetone formed during the reaction work-up. Acetone dimerizes under basic conditions, and acetone was used to filter the reaction mixture to remove the MOF composition. Unlike the MOF compositions used for upgrading reactions, higher aldol products are formed in the ruthenium-catalyzed ethanol upgrading reaction in the absence of the MOF compound. Table 9 shows the quantification of products.

TABLE 9

Quantification of products shown in the mass chromatogram of FIG. 17C.

| | Retention time: | Amount (microliter) | Amount (mmol) | TON (Ru$^{-1}$) | TOF (Ru$^{-1}$h$^{-1}$) |
|---|---|---|---|---|---|
| 1-butanol | 8.3 min | 11139 | 12.45 | 948 | 158 |
| m-xylene (standard) | 11.2 min | | | | |

Figure 17D:
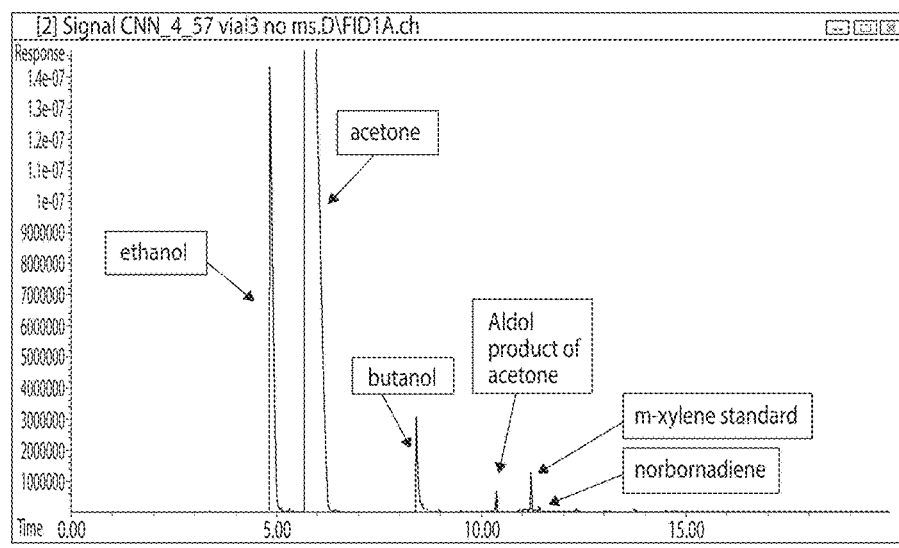
FIG. 17D shows, according to certain embodiments, a flame ionization detector (FID) chromatogram for ethanol upgrading with an exemplary MOF composition at 170° C. for 51.25 hours.

FIG. 17D shows the FID chromatogram for ethanol upgrading with Ru@Ni-tet at 170° C. for 51.25 hours. The FIG chromatogram shows the presence of 2-ethylbutanol and 1-hexanol in addition to ethanol and 1-butanol. The aldol product of acetone was formed during the reaction work-up. While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A composition, comprising:
(a) a metal-organic framework (MOF) compound comprising: (i) a plurality of divalent cobalt ions; and/or (ii) a plurality of divalent nickel ions, wherein the MOF compound further comprises a plurality of ligands, wherein each ligand of the plurality of ligands comprises at least one N-substituted aromatic group, and wherein the plurality of divalent cobalt ions and/or the plurality of divalent nickel ions are coordinated with at least one ligand of the plurality of ligands;
(b) a plurality of metal catalytic compounds, wherein the plurality of metal catalytic compounds comprise ruthenium; and
(c) an alloy comprising: (i) ruthenium metal atoms resulting from reduction of at least a portion of the ruthenium of the plurality of metal catalytic compounds; and (ii) cobalt metal atoms resulting from reduction of at least a portion of the plurality of divalent cobalt ions of the MOF compound; and/or nickel metal atoms resulting from reduction of at least a portion of the plurality of divalent nickel ions of the MOF compound.

2. The composition of claim 1, wherein the alloy comprises ruthenium metal atoms resulting from reduction of at least the portion of the ruthenium of the plurality of metal catalytic compounds and cobalt metal atoms resulting from reduction of at least the portion of the plurality of divalent cobalt ions of the MOF compound.

3. The composition of claim 1, wherein the alloy comprises ruthenium metal atoms resulting from reduction of at least the portion of the ruthenium of the plurality of metal catalytic compounds and nickel metal atoms resulting from reduction of at least the portion of the plurality of divalent nickel ions of the MOF compound.

4. The composition of claim 1, wherein the alloy comprises: (i) Ru- and Co-containing nanoparticles; and/or (ii) Ru- and Ni-containing nanoparticles.

5. The composition of claim 1, wherein each ligand comprises at least one pyrazole group.

6. The composition of claim 1, wherein each ligand comprises at least two pyrazole groups.

7. The composition of claim 1, wherein each ligand has the structure:

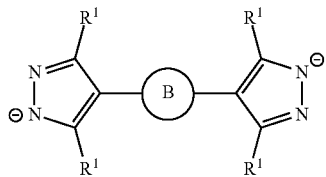

wherein:
B is an optionally substituted aromatic or heterocyclic core;
each $R^1$ is the same or different and is selected from the group consisting of hydrogen, optionally substituted alkyl, optionally substituted aryl, —$NO_2$, —F, —Cl, —Br, —I, —CN, —NC, —$SO_3R'$, —$SO_3H$, —OR', —OH, —SR', —SH, —$PO_3R'$, —$PO_3H$, —$CF_3$, —$NR'_2$, —NHR', and —$NH_2$; and
each R' is the same or different and is optionally substituted alkyl or optionally substituted aryl.

8. The composition of claim 7, wherein each ligand has the structure:

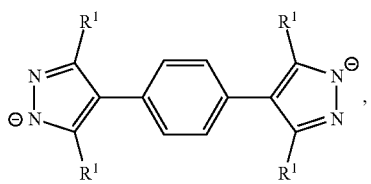

wherein:
each $R^1$ is the same or different and is selected from the group consisting of hydrogen, optionally substituted alkyl, optionally substituted aryl, —$NO_2$, —F, —Cl, —Br, —I, —CN, —NC, —$SO_3R'$, —$SO_3H$, —OR', —OH, —SR', —SH, —$PO_3R'$, —$PO_3H$, —$CF_3$, —$NR'_2$, —NHR', and —$NH_2$, and
each R' is the same or different and is optionally substituted alkyl or optionally substituted aryl.

9. The composition of claim 7, wherein each $R^1$ is the same and is optionally substituted alkyl.

10. The composition of claim 7, wherein each $R^1$ is the same and is unsubstituted alkyl.

11. The composition of claim 7, wherein each $R^1$ is the same and is methyl.

12. The composition of claim 7, wherein Ring B is optionally substituted arylene.

13. The composition of claim 7, wherein each ligand has the structure:

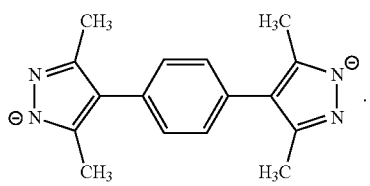

14. The composition of claim 1, wherein the plurality of metal catalytic compounds comprise Ru- and Co-containing nanoparticles.

15. The composition of claim 1, wherein the plurality of metal catalytic compounds comprise Ru- and Ni-containing nanoparticles.

16. The composition of claim 1, where the composition is a catalytic composition.

17. The composition of claim 1, wherein the MOF compound comprises a plurality of pores.

18. The composition of claim 17, wherein at least portion of the plurality of metal catalytic compounds are contained in the plurality of pores.

19. A method, comprising:
exposing the composition of claim 1 to ethanol; and converting ethanol to 1-butanol.

* * * * *

UNITED STATES PATENT AND TRADEMARK OFFICE
CERTIFICATE OF CORRECTION

PATENT NO. : 12,030,839 B2
APPLICATION NO. : 17/106345
DATED : July 9, 2024
INVENTOR(S) : Mircea Dinca et al.

It is certified that error appears in the above-identified patent and that said Letters Patent is hereby corrected as shown below:

In the Claims

At Column 56, Line 30, Claim 16:
"The composition of claim 1, where the composition is a catalytic composition."
Should read:
--The composition of claim 1, wherein the composition is a catalytic composition.--

Signed and Sealed this
Fifteenth Day of October, 2024

Katherine Kelly Vidal
*Director of the United States Patent and Trademark Office*